US012661452B2

(12) United States Patent
Michael

(10) Patent No.: US 12,661,452 B2
(45) Date of Patent: Jun. 23, 2026

(54) CALIBRATION OF INSULIN PENS BY AN ADJUNCT DEVICE

(71) Applicant: G. E. Ehrlich (1995) Ltd., Tel-Aviv (IL)

(72) Inventor: Menash Michael, Hofit (IL)

(73) Assignee: G. E. Ehrlich (1995) Ltd., Tel-Aviv (IL)

( * ) Notice: Subject to any disclaimer, the term of this patent is extended or adjusted under 35 U.S.C. 154(b) by 448 days.

(21) Appl. No.: 18/518,505

(22) Filed: Nov. 23, 2023

(65) Prior Publication Data

US 2024/0148978 A1       May 9, 2024

Related U.S. Application Data

(63) Continuation of application No. 17/013,931, filed on Sep. 8, 2020, now Pat. No. 12,029,884, which is a
(Continued)

(51) Int. Cl.
*A61M 5/315*        (2006.01)
*A61M 5/31*        (2006.01)
(Continued)

(52) U.S. Cl.
CPC .... *A61M 5/31568* (2013.01); *A61M 5/31548* (2013.01); *G16H 20/17* (2018.01);
(Continued)

(58) Field of Classification Search
CPC .......... A61B 17/22; A61B 2017/00292; A61B 2017/00867; A61B 2017/22065;
(Continued)

(56) References Cited

U.S. PATENT DOCUMENTS 3,878,318 A       4/1975   Ziegler, Jr. et al.
5,728,074 A *    3/1998   Castellano ........ A61M 5/31553
                                                          604/209
(Continued)

FOREIGN PATENT DOCUMENTS

EP          2692378         2/2014
EP          3188061         7/2017
(Continued)

OTHER PUBLICATIONS

Applicant-Initiated Interview summary Dated Apr. 24, 2019 From the US Patent and Trademark Office Re. U.S. Appl. No. 15/220,615. (3 Pages).
(Continued)

*Primary Examiner* — Dung T Ulsh

(57)         ABSTRACT

In some embodiments, an adjunct device for tracks time and/or dosage of a medicine. The device may include a connector for mounting the device to a deposable pen injector. The device may be configured to allow use of the native controls and injectors of the injector. For example the device may include a view port for viewing a dose indicator of the injector. The device may include one or more vibration sensors. A processor may be configured to differentiate increasing a dose, decreasing a dose and/or discharging the medicine based on the output of the sensors. Optionally a display of the device may be positioned for simultaneous viewing with the dosage indicator of the injector. For example a user may verify the accuracy of the adjunct device before performing a discharge.

16 Claims, 27 Drawing Sheets

Related U.S. Application Data continuation of application No. 15/220,615, filed on Jul. 27, 2016, now abandoned.

(60) Provisional application No. 62/272,275, filed on Dec. 29, 2015.

(51) Int. Cl.
 *G16H 20/17* (2018.01)
 *G16H 40/63* (2018.01)
 *G16H 50/70* (2018.01)

(52) U.S. Cl.
 CPC . *A61M 2005/3126* (2013.01); *A61M 2205/33* (2013.01); *A61M 2205/3553* (2013.01); *A61M 2205/3569* (2013.01); *A61M 2205/3576* (2013.01); *A61M 2205/50* (2013.01); *A61M 2205/502* (2013.01); *A61M 2205/52* (2013.01); *A61M 2205/8206* (2013.01); *A61M 2209/00* (2013.01); *A61M 2209/04* (2013.01); *G16H 40/63* (2018.01); *G16H 50/70* (2018.01)

(58) Field of Classification Search
 CPC ............ A61B 2017/22079; A61F 2/95; A61M 25/005; A61M 25/1002
 See application file for complete search history.

(56) References Cited

U.S. PATENT DOCUMENTS

| | | | |
|---|---|---|---|
| 6,270,455 | B1 | 8/2001 | Brown |
| 8,556,865 | B2 | 10/2013 | Krulevitch et al. |
| 8,556,866 | B2 | 10/2013 | Krulevitch et al. |
| 8,743,662 | B2 | 6/2014 | Sjolund et al. |
| 2006/0224123 | A1 | 10/2006 | Friedli et al. |
| 2008/0243552 | A1 | 10/2008 | Asakawa |
| 2011/0313350 | A1 | 12/2011 | Krulevitch et al. |
| 2012/0072236 | A1 | 3/2012 | Atkin |
| 2013/0236872 | A1 | 9/2013 | Laurusonis et al. |
| 2013/0310756 | A1 | 11/2013 | Whalley et al. |
| 2014/0003626 | A1 | 1/2014 | Holman et al. |
| 2014/0020010 | A1 | 1/2014 | Fan et al. |
| 2015/0018775 | A1 | 1/2015 | Groeschke et al. |
| 2015/0061867 | A1 | 3/2015 | Engelhard et al. |
| 2015/0290396 | A1 | 10/2015 | Nagar et al. |
| 2016/0213853 | A1 | 7/2016 | Despa et al. |
| 2016/0265698 | A1 | 9/2016 | Cai |
| 2017/0182256 | A1 | 6/2017 | Andersen et al. |
| 2017/0182258 | A1 | 6/2017 | Michael |
| 2017/0216524 | A1 | 8/2017 | Haider |
| 2018/0280624 | A1 | 10/2018 | Bitton et al. |
| 2020/0360614 | A1 | 11/2020 | Schabbach et al. |
| 2020/0397998 | A1 | 12/2020 | Michael |

FOREIGN PATENT DOCUMENTS

| | | | | |
|---|---|---|---|---|
| EP | | 3572107 | 11/2019 | |
| WO | WO | 99/43283 | 9/1999 | |
| WO | WO | 2012/046199 | 4/2012 | |
| WO | WO | 2013/156510 | 10/2013 | |
| WO | WO | 2014/020010 | 2/2014 | |
| WO | WO | 2014/064691 | 5/2014 | |
| WO | WO-2014064691 A2 | * | 5/2014 | ............ G16H 20/13 |
| WO | WO | 2015/136513 | 9/2015 | |
| WO | WO-2015136513 A1 | * | 9/2015 | ........ A61M 5/31568 |
| WO | WO | 2015/185687 | 12/2015 | |
| WO | WO | 2018/015401 | 1/2018 | |
| WO | WO | 2020/110124 | 6/2020 | |

OTHER PUBLICATIONS

Communication Pursuant to Article 94(3) EPC Dated Feb. 1, 2019 From the European Patent Office Re. Application No. 16207111.2. (15 pages).

Communication Pursuaunt to Rules 70(2) and 70a(2) EPC and Reference to Rule 39(1) EPC Dated Nov. 6, 2017 From the European Patent Office Re. Application No. 16207111.2. (2 Pages).

European Search Report and the European Search Opinion Dated Sep. 29, 2017 From the European Patent Office Re. Application No. 16207111.2. (12 Pages).

International Preliminary Report on Patentability Dated Jun. 10, 2021 From the International Bureau of WIPO Re. Application No. PCT/IL2019/051309. (6 Pages).

International Search Report and the Written Opinion Dated Feb. 27, 2020 From the International Searching Authority Re. Application No. PCT/IL2019/051309. (10 Pages).

Notice of Allowance Dated Nov. 7, 2023 from the US Patent and Trademark Office Re. U.S. Appl. No. 17/013,931. (7 pages).

Official Action Dated May 1, 2023 Together with Interview Summary from the US Patent and Trademark Office Re. U.S. Appl. No. 17/013,931. (28 pages).

Official Action Dated Aug. 6, 2019 From the US Patent and Trademark Office Re. U.S. Appl. No. 15/220,615. (41 pages).

Official Action Dated Feb. 26, 2019 From the US Patent and Trademark Office Re. U.S. Appl. No. 15/220,615. (39 Pages).

Restriction Official Action Dated Oct. 12, 2018 From the US Patent and Trademark Office Re. U.S. Appl. No. 15/220,615. (7 pages).

Asakura et al. "Comparative Study on Click Sounds Produced by Three Types of Prefilled Insulin Pen Devices (FlexPen®, SoloSTAR®, MirioPen®) on Dose Setting", Japanese Journal of Pharmaceutical Health Care and Sciences, 34(11): 1023-1027, 2008.

Hickey "How This Little Gadget Could Be A Real Lifesaver for People With Diabetes", The Irish Independent, Lifestyle Health, 8 P., Jun. 5, 2012.

Meas "LDT With Crimps Vibration Sensor/Switch", Measurement Specialities, MEAS, LDT0-028K, Piezo Vibration Rev. 1, 4 P., 1998.

Merriam-Webster "Horseshoe", Merriam-Webster Dictionary Definition, merriam-webster.com, pp. 1-5, Retrieved on Feb. 14, 2019.

One Technology Way "Analog Devices: Small, Low Power, 3-Axis ±2 g Accelerometer ADXL327", One Technology Way, Analog Devices, Inc., Specification Sheet, p. 1-16, 2009.

Advisory Action Dated Feb. 7, 2025 From the US Patent and Trademark Office Re. U.S. Appl. No. 17/298,579. (3 Pages).

Official Action Dated Oct. 23, 2024 From the US Patent and Trademark Office Re. U.S. Appl. No. 17/298,579. (14 Pages).

Official Action Dated Jul. 25, 2025 from the US Patent and Trademark Office Re. U.S. Appl. No. 17/298,579. (9 Pages).

Official Action Dated Mar. 21, 2024 from the US Patent and Trademark Office Re. U.S. Appl. No. 17/298,579. (25 pages).

* cited by examiner

Figure 9A:
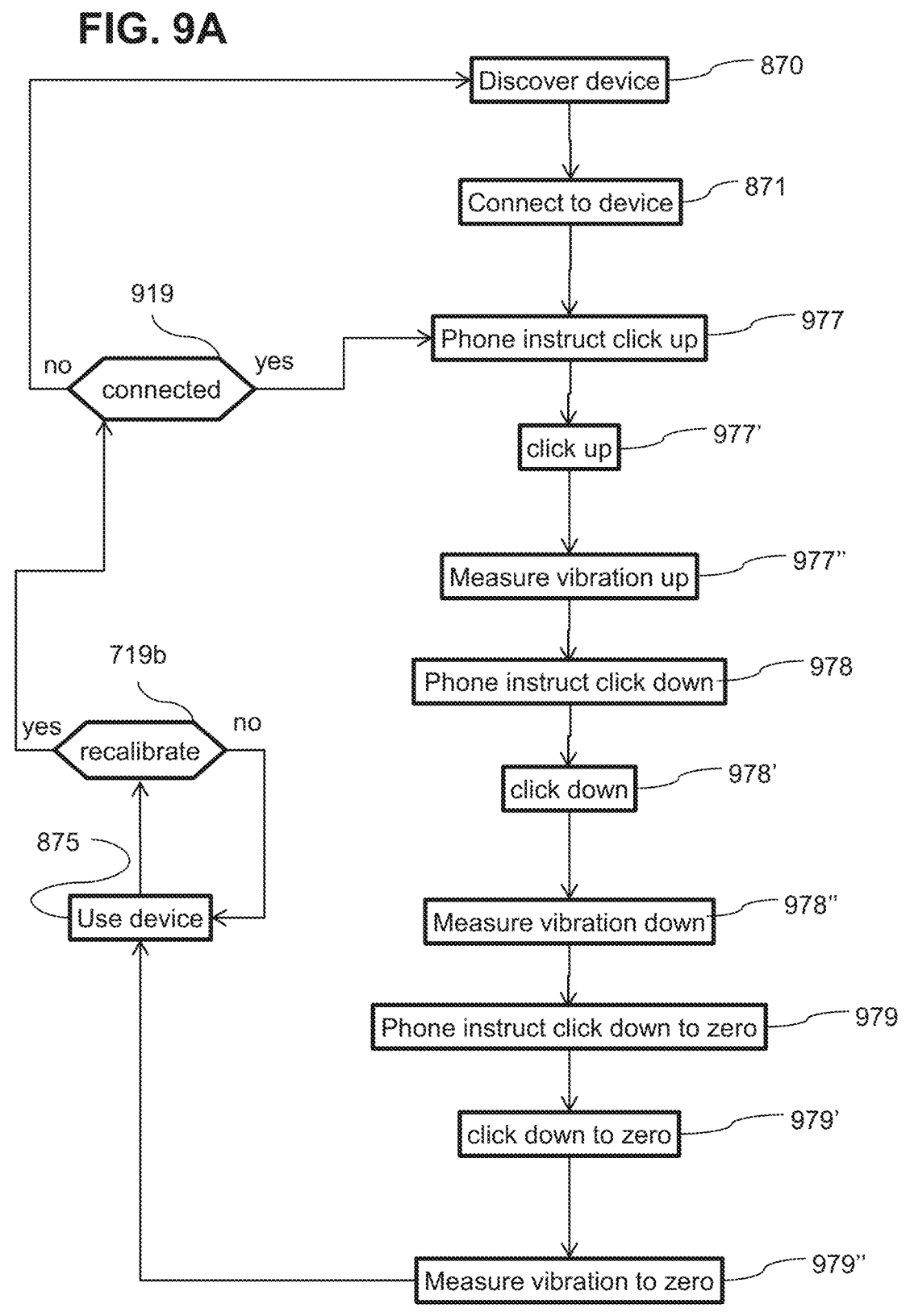

Discover device —— 870

Connect to device —— 871

919
connected
no / yes

Phone instruct click up —— 977 click up —— 977'

Measure vibration up —— 977"

Phone instruct click down —— 978 click down —— 978'

Measure vibration down —— 978"

Phone instruct click down to zero —— 979 click down to zero —— 979'

Measure vibration to zero —— 979"

719b
recalibrate
yes / no

875
Use device

CALIBRATION OF INSULIN PENS BY AN ADJUNCT DEVICE

RELATED APPLICATION

This application is a continuation of U.S. patent application Ser. No. 17/013,931, filed on Sep. 8, 2020, which is a continuation of U.S. patent application Ser. No. 15/220,615 filed on Jul. 27, 2016, which claims the benefit of priority under 35 USC 119(e) of U.S. Provisional Patent Application No. 62/272,275 filed on Dec. 29, 2015. The contents of the above applications are all incorporated by reference as if fully set forth herein in their entirety.

FIELD AND BACKGROUND OF THE INVENTION

The present invention, in some embodiments thereof, relates to an adjunct device and system for an injector, and, more particularly, but not exclusively, to a device to detect and/or indicate times and/or dosages of insulin injections.

U.S. Patent Publication No. 2014/020010 discloses, "A supplemental device for attachment to an injection device. A supplemental device for attachment to an injection device, the supplemental device comprising: a housing; an electro-mechanical switch arrangement having an open state and a closed state, the electromechanical switch arrangement comprising a protrusion configured to contact a surface of the injection device while the supplemental device is attached to the injection device; a dose dialed detector operable to detect a dose of medicament dialed into the attached injection device; and a processor arrangement configured to: monitor the detected dose of medicament dialed into the attached injection device; detect a change in the state of the electro-mechanical switch arrangement; and change a display output of the supplemental device when a change in the state of the electromechanical switch arrangement is detected while a zero dose is dialed into the attached injection device".

European Patent Application Publication No. 2692378 discloses a "pen-type drug injection device (1) and attach-able electronic add-on monitoring module (2) for monitoring and logging dose setting and administration, the module comprising a rotatably supported cylindrical member (101), wherein an outer surface of the cylindrical member is provided with at least one track, each track comprising conductive segments and non-conductive segments; at least one pair of contacts, each pair of contacts configured to engage a respective one of the at least one tracks; and an engaging part (110) configured to couple the cylindrical member to a rotatable part (19) of an attached injection device such that rotation of the rotatable part causes rotation of the cylindrical member".

U.S. Published Patent Application No. 20130310756 discloses "devices, systems and methods for measuring the dose remaining in a drug delivery device that is used for delivering a dose to a patient. In some embodiments, a dose measurement system for measuring the liquid volume in a container includes a plurality of light sources which are disposed and configured to emit electromagnetic radiation toward the container. A plurality of sensors are located in the apparatus that are optically coupleable to the plurality of light sources and are disposed and configured to detect the electromagnetic radiation emitted by at least a portion of the light sources. The apparatus also includes a processing unit configured to receive data representing the portion of the detected electromagnetic radiation from each of the plurality of sensors. The processing unit is further operable to convert the received data into a signature representative of the electromagnetic radiation detected by the plurality of sensors".

U.S. Published Patent Application No. 20060224123 discloses "A device for administering a substance including a measuring mechanism for measuring, without contact, a position, the measuring involving at least two elements of the device, at least one of the elements moveable with respect to the other, the measuring mechanism including at least two optical sensors for sensing a relative movement between the elements, the relative movement providing a profile trajectory. The present invention encompasses a method for measuring, without contact, a relative position between elements or structures which can be moved relative to each other, wherein sensors sense and/or record a profile trajectory associated with the elements or structures when one element is moved relative to another element, the trajectory processed to determine the position".

U.S. Pat. No. 6,270,455 discloses "a networked system for communicating information to a patient and for remotely monitoring the patient. The system includes a server and a remote interface for entering in the server a set of queries to be answered by the patient. The server may be a web server and the remote interface may be a personal computer or remote terminal connected to the server via the Internet. The system also includes a measurement apparatus for providing measurement data related to a patient's condition and treat-ment, and a remotely programmable apparatus connected to the server via a communication network, such as the Inter-net. The remotely programmable apparatus interacts with the patient in accordance with a script program received from the server. The server includes a script generator for generating the script program from the set of queries entered through the remote interface. The script program is received and executed by the remotely programmable apparatus to communicate the queries to the patient, to receive responses to the queries, and to transmit the responses from the apparatus to the server. The measurement data provided by the measurement apparatus may include physiological con-dition data and drug delivery measurement data for paper-less recordation at a remote location".

LDT with Crimps Vibration Sensor/Switch, by TE Con-nectivity Ltd. family of companies, 1000 Lucas Way Hamp-ton, VA 23666 USA discloses that "The LDT0-028K is a flexible component comprising a 28 μm thick piezoelectric PVDF polymer film with screen-printed Ag-ink electrodes, laminated to a 0.125 mm polyester substrate, and fitted with two crimped contacts. As the piezo film is displaced from the mechanical neutral axis, bending creates very high strain within the piezopolymer and therefore high voltages are generated. When the assembly is deflected by direct contact, the device acts as a flexible "switch", and the generated output is sufficient to trigger MOSFET or CMOS stages directly. If the assembly is supported by its contacts and left to vibrate "in free space" (with the inertia of the clamped/ free beam creating bending stress), the device will behave as an accelerometer or vibration sensor. Adding mass, or alter-ing the free length of the element by clamping, can change the resonant frequency and sensitivity of the sensor to suit specific applications. Multi-axis response can be achieved by positioning the mass off center. The LDTM-028K is a vibration sensor where the sensing element comprises a cantilever beam loaded by an additional mass to offer high sensitivity at low frequencies".

Additional background art includes Toshinari Asakura, Hiroaki Seino, Miho Kageyama and Noriaki Yohkoh; "Comparative Study on Click Sounds Produced by Three

US 12,661,452 B2

3

Types of Prefilled Insulin Pen Devices (FlexPen®, SoloS-
TAR®, MirioPen®) on Dose Setting, Jpn. J. Pharm. Health
Care Sci., 34(11) 1023-1027 (2008).

SUMMARY OF THE INVENTION

According to an aspect of some embodiments of the
invention, there is provided a dosage tracking device for a
pen injector the injector including a housing, a dial for
designating a dosage by a user, a dosage indicator for
displaying the dosage to the user and a discharge mechanism
for discharging the dosage; the tracking device comprising:
a viewport in the dosage tracking device sized to display the
dosage indicator of the pen to the user; a connector config-
ured to reversibly hold the tracking device to the housing
with the dosage indicator visible through the viewport; one
or more vibration sensors held to the pen by the connector,
the one or more vibration sensors producing a first output in
response to rotating the dial to add a unit to a dosage of the
pen, a second output in response to rotating the dial to
subtract a unit from a dosage of the pen and a third output
in response to discharge of the dosage by the pen; a
processor programmed to adjust a dosage counter in one
manner in response to the first output and adjust a the dosage
counter in a second manner different from the first manner
in response to the second output and to store a timing of the
discharge based of a time of the third output.

According to some embodiments of the invention, the first
manner includes incrementing the dosage and the second
manner includes decrementing the dosage.

According to some embodiments of the invention, each of
the one or more sensors measure vibrations on at least two
separate axes and wherein the processor is programmed to
differentiate between the first output and the second output
based on a difference between vibration on the at least two
axes.

According to some embodiments of the invention, the one
or more vibration sensors include a first vibration sensors
and a second vibration sensor and wherein the processor is
programmed recognizing a difference between an output of
each of the first vibration sensor and an output of the second
vibration sensor and to differentiate between the first output
and the second output based on the difference.

According to some embodiments of the invention, each of
the one or more vibration sensors is held by the connector in
a different fixed respective position with respect to the pen
injector.

According to some embodiments of the invention, the
device further comprises: a digital display configured to
display a value of the counter.

According to some embodiments of the invention, the
digital display is further configured to display a timing of the
discharging.

According to some embodiments of the invention, con-
nector is configured to retain the display adjacent to the
viewport such that a user views the display and the viewport
simultaneously from a single view point.

According to some embodiments of the invention, when
the device is connected to the injector, an exposed area of the
dial is at least 98% of the exposed area of the dial without
the device.

According to some embodiments of the invention, at least
one of the one or more vibration sensors has a sample rate
of greater than 2000 per second.

According to some embodiments of the invention, at least
one of the one or more vibration sensors measures motion in
circumferential to an axis of the pen injector.

According to some embodiments of the invention, the
processor is further programmed to detect a direction of the
motion circumferential to the axis and to increment the
dosage counter upward for the motion in a first direction.

According to an aspect of some embodiments of the
invention, there is provided a method of tracking a dosage
from a pen injector comprising: reversibly retaining one or
more vibration sensor on the pen injector; producing a first
output from the one or more vibration sensors when a unit
is added to an injection dosage; producing a second output
from the one or more vibration sensors when a unit is
subtracted from the injection dosage; producing a third
output from the one or more vibration sensors when the
injection dosage is discharged; analyzing an output of the
vibration sensor to distinguish the first output, the second
output and the third output; adjusting a dosage counter in a
first manner in response to the first output; adjusting the
dosage counter in a second manner different from the first
manner in response to the second output; and storing a
timing of the discharge in response to the third output.

According to some embodiments of the invention, the first
manner includes incrementing the dosage counter and the
second manner includes decrementing the dosage counter.

According to some embodiments of the invention, the
method further comprises: retaining a window in a position
to allow a user to view a dosage indicator of the injector
through the window.

According to some embodiments of the invention, the
method further comprises: displaying a value of the dosage
counter.

According to some embodiments of the invention, the
displaying is in a position that the value is viewed simulta-
neously from a single vantage point with a dosage indicator
of the pen injector.

According to some embodiments of the invention, the
method further comprises: checking that the value of the
dosage counter is in agreement with the dosage indicator of
the injector.

According to some embodiments of the invention, first
sensor output includes a measure of vibration on at least two
axes and wherein the analyzing includes comparing a vibra-
tion on a first of the two axes to a vibration on a second of
the two axes.

According to some embodiments of the invention, the first
sensor output includes a measure of vibration on at least
locations and wherein the analyzing includes comparing a
vibration on a first of the two locations to a vibration on a
second of the two locations.

According to some embodiments of the invention, the
analyzing includes at least one calculation selected form the
group consisting of comparing a pulse width of the output to
a known value, computing a ratio of pulse widths in the
output, comparing a slope of the output to a known value,
determining a direction of movement based on the output
and computing a ratio of slopes in the output.

According to an aspect of some embodiments of the
invention, there is provided a dosage tracking system for a
drug delivery device the delivery device including a hous-
ing, a and a dosage indicator for displaying the dosage to the
user; the tracking device comprising: one or more sensors
sensing an injection dosage; a processor connected by a data
transfer channel to the sensors for receiving an output of the
sensors and configured for computing an estimated dosage
based on an output of the one or more sensors; a display for
viewing the estimated dosage; a viewport sized to display
the dosage indicator of the delivery device; a connector
configured to reversibly hold the tracking device to the housing with the dosage indicator visible through the viewport and the display simultaneously visible along with the viewport from a single vantage point.

According to some embodiments of the invention, the connector is configured for holding the display and the viewport to be simultaneously views by a user of the device while adjusting the dosage of the delivery device.

According to some embodiments of the invention, the dosage tracking system further comprises: a user interface for adjusting the estimated dosage.

According to some embodiments of the invention, the user interface includes at least one hand activated switch mounted to the housing.

According to some embodiments of the invention, the dosage tracking system further comprises: a user interface for storing the estimated dose and a time of dosage application.

According to some embodiments of the invention, the connector also retains the sensor in functional connection with the delivery device.

According to some embodiments of the invention, the connector is shaped and sized to grasp a cylindrical object having a width between 5 mm and 3 cm.

According to some embodiments of the invention, the connector includes an elastic surface for contact with the delivery device with a hardness between 15 to 70 shore.

According to an aspect of some embodiments of the invention, there is provided a dosage tracking device for a pen injector, the injector including a housing, a dial for designating a dosage by a user, a dosage indicator for displaying the dosage to the user and a discharge mechanism for discharging the dosage; the tracking device comprising: a viewport in the dosage tracking device sized to display the dosage indicator of the pen to the user; a connector configured to reversibly hold the tracking device to the housing with the dosage indicator visible through said viewport; and one or more vibration sensors held to said pen by said connector, said one or more vibration sensors producing: a first output in response to rotating the dial to add a unit to a dosage of the pen; a second output in response to rotating the dial to subtract a unit from a dosage of the pen; and a third output in response to discharge of the dosage by the pen; a processor programmed to increment a dosage counter in response to said first output and decrement said dosage counter in response to said second output and to record a timing of the discharge based of a time of said third output.

According to some embodiments of the invention, the connector is configured to retain said display adjacent to the viewport such that a user views said display and said viewport simultaneously from a single view point.

According to some embodiments of the invention, each of said one or more sensors measure vibrations on at least two separate axes and wherein said processor is programmed to differentiate between said first output and said second output based on a difference between vibration on said at least two axes.

According to some embodiments of the invention, at least one of the sensors includes an accelerometer and at least one other senor includes a gyro.

According to some embodiments of the invention, the device further comprising a digital display configured to display a value of said counter and said timing of said discharging.

According to some embodiments of the invention, the device further comprising a user verification button for manually approving storage of at least one of said display value and said timing in a computational device.

According to some embodiments of the invention, at least one of said one or more vibration sensors has a sample rate of greater than 2000 per second.

According to some embodiments of the invention, at least one of said one or more vibration sensors measures motion in circumferential to an axis of said pen injector.

According to some embodiments of the invention, one direction of said motion circumferential to said axis corresponds to said first output and a second direction of said motion circumferential to said axis corresponds to said second output.

According to an aspect of some embodiments of the invention, there is provided a method of tracking a dosage from a pen injector comprising: reversibly retaining one or more vibration sensors on said pen injector; producing a first output from said one or more vibration sensors when a unit is added to an injection dosage; producing a second output from said one or more vibration sensors when a unit is subtracted from said injection dosage; producing a third output from said one or more vibration sensors when said injection dosage is discharged; analyzing an output of said vibration sensor to distinguish said first output, said second output and said third output; incrementing the dosage counter in response to said first output; decrementing said dosage counter in response to said second output; and recording a timing of the discharge in response to said third output.

According to some embodiments of the invention, the method further comprises retaining a window in a position to allow a user to view a dosage indicator of the injector through said window and displaying a value of said dosage counter in a position that said value is viewed simultaneously from a single vantage point with said dosage indicator of said pen injector.

According to some embodiments of the invention, the method further comprises checking that said value of said dosage counter is in agreement with said dosage indicator of said injector and approving storage of said value in a computational device.

According to some embodiments of the invention, first sensor output includes a measure of vibration on at least two axes and wherein said analyzing includes comparing a vibration on a first of said two axes to a vibration on a second of said two axes.

According to some embodiments of the invention, said analyzing includes at least one calculation selected form the group consisting of comparing a pulse width of the output to a known value, computing a ratio of pulse widths in said output, comparing a slope of said output to a known value, determining a direction of movement based on said output and computing a ratio of slopes in said output.

According to an aspect of some embodiments of the invention, there is provided a dosage tracking system for a pen injector, the injector including a housing, and a dosage indicator for displaying the dosage to the user; the system comprising a tracking device comprising: one or more sensors sensing an adjustment of a dosage of said injector; a processor connected by a data transfer channel to said sensors for receiving an output of said sensors and configured for computing an estimated dosage based on an output of said one or more sensors; a display for viewing said estimated dosage; a viewport sized to display the dosage indicator of the delivery device; and a connector configured to reversibly hold the tracking device to the housing with the dosage indicator visible through said viewport and said display simultaneously visible along with said viewport from a single vantage point.

According to some embodiments of the invention, the dosage tracking system further comprises a user interface for adjusting said estimated dosage.

According to some embodiments of the invention, said user interface includes at least one hand activated switch mounted to said housing, wherein activation of said switch results in storing said estimated dose.

According to some embodiments of the invention, said connector is shaped as a horseshoe and sized to grasp a cylindrical object having a width between 5 mm and 3 cm, said grasp is around at least 180° of a circumference of said object.

According to some embodiments of the invention, said connector has inner portion having a diameter smaller than a diameter of said injector and said connector is made of a material configured to elastically permit retention of said injector in the inner portion.

According to some embodiments of the invention, said connector comprises Acrylonitrile Butadiene Styrene (ABS).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
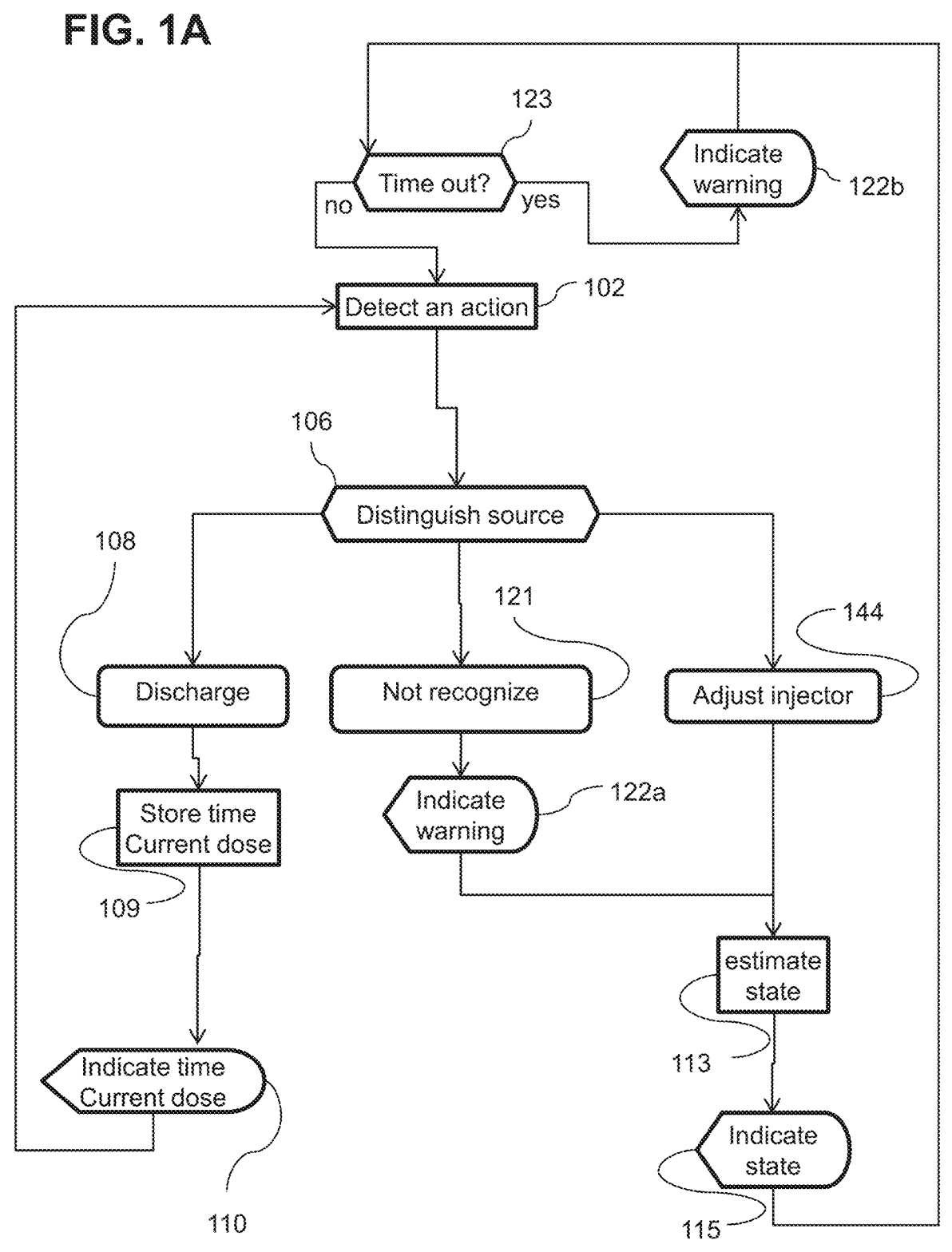

FIGS. 1A and 1B are flow chart illustrations of methods for reporting a state of an injector in accordance with embodiments of the current invention;

FIGS. 9A and 9B are flow chart illustrations of a method of calibrating a device for monitoring drug administration in accordance with some embodiments of the current invention;

FIGS. 19A, 19B and 19C illustrate perspective views of an adjunct device for use in a drug delivery device, in accordance with some embodiments of the present invention, in which FIG. 19A illustrates an exemplary embodiment of an adjunct device, FIG. 19B illustrates an exemplary embodiment of an adjunct device as used with an injector, and FIG. 19C shows another view of an exemplary embodiment of a device as used with an injector;

FIGS. 20A, 20B and 20C illustrate a side view of an adjunct device for use in a drug delivery device in accordance with some embodiments of the present invention, in which FIG. 20A illustrates a first side view of an embodiment of an adjunct device, FIG. 20B illustrates a second, opposite to the first side view illustrated in FIG. 20A, side view of an embodiment of an adjunct device and FIG. 20C illustrates the first side view illustrated in FIG. 20A after being mounted over an injector device;

DESCRIPTION OF SPECIFIC EMBODIMENTS OF THE INVENTION

Figure 1B:
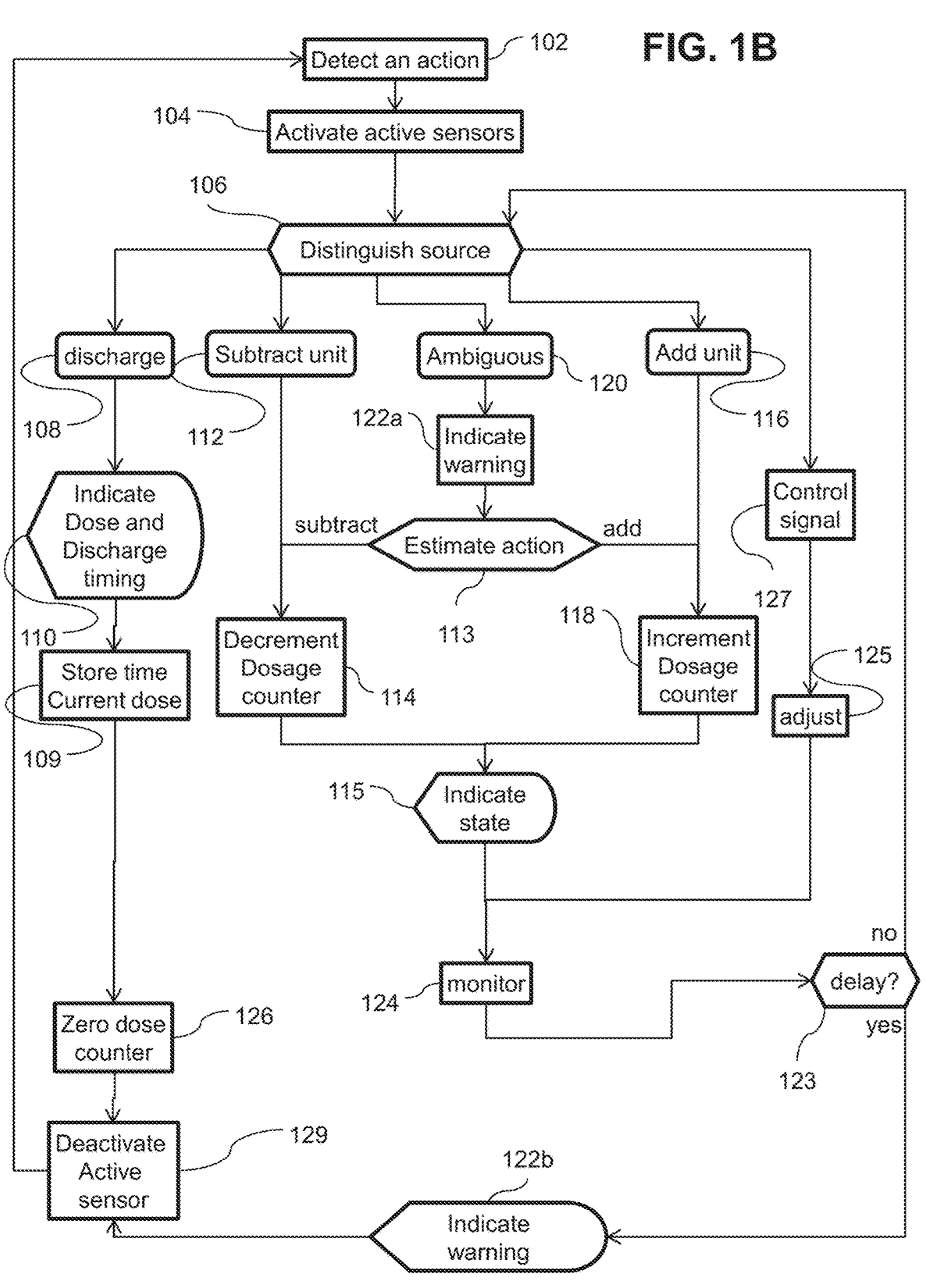

The present invention, in some embodiments thereof, relates to an adjunct device and system for an injector, and, more particularly, but not exclusively, to a device to detect and/or indicate times and/or dosages of insulin injections.
Overview An aspect of some embodiments of the current invention relates to an adjunct device for a disposable injector pen, the device including a vibration sensor and a processor for detecting the quantity and timing of an injection. Optionally, the processor may be programmed to distinguish actions of the device based on their characteristic vibrations.

In some embodiments, the processor may be programmed to differentiate between the vibrations due to increasing a dosage and/or vibrations due to decreasing a dosage and/or vibrations due to discharge. For example, the pen injector may include a selector for setting the dosage. In some embodiments, the selector may make one characteristic vibration when the dosage is increased and/or a second characteristic vibration when the dosage is decreased. For example the selector may include a dial at the proximal end of the injector. The dial optionally makes a clicking sound when the dose is changed. The vibration sensor is optionally attached to the injector at a location chosen to enhance detection of vibrations due to the selector and/or at a location chosen to enhance detection of vibrations due to discharge of the drug. Optionally a vibration sensor may have a sample rate of between 100 to 1000 samples per second and/or between 1000 and 10000 samples per second and/or 10000 to 100000 samples per second.

In some embodiments, differentiation between different sources of vibration may be according to characteristics of the vibrations (for example the characteristics may include frequency of vibrations, the timing of vibrations and/or the order of vibrations and/or amplitude of vibrations). Differentiation between sources of the vibrations may be based on differences of characteristics of the vibrations measured at different locations and/or on different axes. For example vibrations due to discharge may be localized towards the center of an injector and/or vibrations due to changing a dosage may be localized more towards the proximal end of the injector.

For example, the different location of the vibrations may affect the relative amplitude of the vibrations at the location of each sensor. For example, a vibration sensor may sense movement in a direction circumferential to an injector pen. Optionally, raising and lowering a dosage may be detected based on the direction of movement, for example the direction movement circumferential to the injector axis. For example, actions may be differentiated by the relative magnitude of signals on different axes. For example discharging a dose may be recognized by a high ratio of magnitude of circumferential to radial amplitude and/or discharging a dose may be recognized by a lower circumferential to radial amplitude ratio.

In some embodiments, the device may include multiple sensors. For example the multiple sensors may include similar sensors in different locations and/or with different orientations. For example an accelerometer may be placed on the device measuring vibration in two different orientations, for example longitudinally and/or laterally (for example three perpendicular axes may include longitudinal (along the length of the device, lateral (tangent to the device surface at the location) and transverse (passing through the sensor and the axis of the device, perpendicular to the surface of the device). For example a first piezo vibration sensor may be placed towards the proximal end of the device (for the sake of the current disclosure, the proximal end of a device will be defined as the end opposite the needle insertion point) and a second piezo sensor on the distal end (for the sake of the current disclosure, the distal end of a device will be defined as the end from which the needle protrudes) and/or one piezo sensor may be placed on the front face of the injector (the same side as the dosage window) while the other is placed on the dorsal side of the injector (opposite the dosage window).

In some embodiments, multiple sensors may include different types of sensors. For example an adjunct device may include different sensors of a similar type, for example one sensor may include a piezo vibration sensor while the other may include an accelerometer and/or two piezo sensors tuned for different frequencies and/or different orientations. Alternatively or additionally, a device may include two different kinds of sensors, for example a vibration sensor and an optical sensor and/or a tactile sensor. For example, a device may include an accelerometer and a gyro sensor. For example, the gyro may be used to discern the orientation of the device. Orientation data from the gyro is optionally used to reduce noise in the accelerometer signal (for example by differentiating between acceleration due to movement and acceleration due to gravity).

Alternatively or additionally, data from a gyro sensor may be used to discern user actions. For example, holding the injector steady with changes of less than 5 degrees and/or less than 15 degrees for between 0.25 seconds to 1 second and/or 1 second to 5 seconds and/or 5 seconds to 1 minute may be a associated with adjusting a dosage. Additionally or alternatively orienting the longitudinal axis of the injector within 1 degree of horizontal and/or between 1 to 5 degrees of horizontal and/or between 5 to 25 degrees from horizontal for between 0.25 seconds to 1 second and/or 1 second to 5 seconds and/or 5 seconds to 1 minute may be a associated with adjusting a dosage. For example, a reorienting of the injector over an angle of greater than 45 degrees and/or greater than 90 degrees after setting a dosage may be a sign of beginning injection. For example, holding the device steady between 0.25 seconds to 1 second and/or 1 second to 5 seconds and/or 5 seconds to 1 minute at an angle greater the 5 degrees to horizontal and/or greater than 15 degrees and/or greater than 25 degrees and/or greater than 60 degrees to horizontal and/or holding the device steady at a new angle (differing from the angle during dosage adjustment for example by at least 5 degrees and/or at least 15 degrees and/or at least 25 degrees and/or at least 60 degrees) for between 0.25 seconds to 1 second and/or 1 second to 5 seconds and/or 5 seconds to 1 minute and/or between 1 to 10 minutes after setting the dosage may be a sign of discharge of the drug.

In some embodiments, a combination of various factors may be used to identify an action and/or eliminate an action from consideration when interpreting sensor data. For example, an adjustment of a dosage may be identified by a combination of device orientation, vibration pulse width and/or vibration slope ratio.

In some embodiments, stimulation of a passive sensor (for example a piezo and/or a mechanical sensor) may activate an active sensor (for example an optical sensor and/or a light source). In some embodiments, the combination of sensors may increase sensitive and/or specificity in distinguishing actions of the injector. For example, a piezo sensor may be sensitive to a vibration from a dosage selector to activate an optical sensor that detects the direction of movement of a dosage adjusting dial. Optionally, while the optical sensor is on standby, when a first sound is recognized by a processor as a vibration of the dosage sensor, the optical sensor is activated. Alternatively or additionally, the processor may run a distinguishing algorithm to differentiate between sounds of increasing and/or decreasing the dosage. When the differentiation is successful the dosage is set accordingly. When the differentiation fails, the dosage may be estimated based on other factors (for example in the absence of indicators otherwise, it may be assumed that the first vibration is increasing dosage from 0 to 1).

An aspect of some embodiments of the current invention relates to an adjunct device for a disposable injector pen. The device is optionally reversibly connected to the injector, for example the device may be configured for attachment and removal and reattachment to the same injector and/or another injector. Optionally the device does not affect or minimally affects operation of the injector. For example, some or all of the controls of the injector may be accessible to a user and/or perform their regular function while the device is connected to the injector. For example, some or all of the indicators of the injector may be visible to a user and/or perform their regular functions while the device is connected to the injector. For example, the injector may continue to function according to its specifications when used according to normal operating procedures while the device is connected to the injector. Optionally the adjunct device does not cover over and/or does not contact and/or does not impede movement of a dosage selector of the injector. For example the exposed area of the dosage selector with the adjunct device installed may range between 98 to 100% and/or 95 to 98% and/or 80 to 95% and/or 60 to 80% and/or 30 to 60% of the exposed area of the dosage selector of the injector without the adjunct device.

In some embodiments, a dosage indicator of the injector may be visible to a user when the adjunct device is functioning and/or connected to the injector. For example, the adjunct device may have a viewport including for example a window and/or a periscope for viewing the dosage indicator of the injector. For example when the adjunct device is functioning and/or connected to the injector, a dosage selector of the injector may be accessible to a user and/or may function according to the specifications of the injector without the adjunct device.

In some embodiments, an indicator of the adjunct device and the injector may be situated for simultaneous viewing and/or for checking agreement. For example when the adjunct device is connected to the injector, the display of the adjunct device may be situated adjacent to the dosage indicator of the injector and/or a viewport for the dosage indicator of the injector. Optionally, before injecting, the user may check the agreement of the dosage indicated by the injector and the dosage indicated by the adjunct device. Optionally the display may include for example a digital display including for example a segment display (optionally including a light emitting diode LED and/or a liquid crystal diode LCD) and/or a full area two dimensional display (optionally an LCD including a High performance addressing display HPA and/or a Thin Film Transistor display TFT and/or an in phase switching display), and/or a touchscreen.

In some embodiments, an adjunct device may include a user interface. For example, the user interface may include a control for adjusting the dosage counter of the adjunct device, for example to bring the estimated dosage in agreement with the current dosage setting of the delivery device. Additionally or alternatively, the user interface may include a control for the user to verify saving of the dosage and/or time of delivery. For example, the user interface may be in the housing of the adjunct device and/or mounted on the drug delivery device. For example, the user interface may include hand activated switch. For example a hand activated switch may include a pressure switch and/or a proximity switch and/or a touch screen. For example a pressure switch may include a button and/or a direction stick and/or a rocker switch.

Detailed Embodiments

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Method for Reporting the State of an Injector

FIG. 1A is a flow chart illustrating a method for reporting a state of an injector in accordance with an embodiment of the current invention. Optionally actions of an injector may be detected using one or more passive sensors. For example, vibration may be detected by one or more piezo sensors. Based on the sensor output, a processor may track a state of the injector and/or report the injector state (for example the current dosage, the last injected dosage, and/or the last injected time) to the user. Data is optionally stored and/or sent to an external device, for example a smart phone.

In some embodiments, detecting 102 an activity of the injector will start a distinguishing 106 process. For example, detecting 102 an activity of an injector may include detecting a vibration of the injector. For example, a processor may distinguish 106 between vibrations made by adjusting 144 the injector, vibrations made by discharging 108 a drug and/or other 121 vibrations.

In some embodiments, when a vibration associated with adjusting 144 is distinguished 106, the processor will be configured (for example by programming) to estimate 113 a current state. For example, estimating 113 a state may include estimating 113 a current dosage setting of the injector. Optionally, estimating 113 a current dosage setting may include remembering a previous dosage setting, differentiating between vibrations associated with increasing a dosage and/or vibrations associated with decreasing a dosage, deductions based on timing (for example a first adjustment 144 after a previous discharge 108 may be estimated 113 to be an increase in dosage and/or two immediate clicks followed by a pause and a further click may be estimated 113 to be two steps forward and one step back). Optionally the estimated state (for example the set dosage and/or the time) may be indicated 115 to a user. For example, the dosage setting may be indicated 115 to the user on a display of the adjunction device, via a voice message and/or via a separate device (for example a message and/or a voice messages are optionally disseminated by the separate device (for example a text message and/or an audio message relayed to a cell phone of the user).

In some embodiments, when the adjunct device distinguishes 106 a vibration associated with discharging 108 of the drug, the adjunct device may store 109 the current time and dosage. For example the current time and dosage may be stored 109 in an internal buffer and/or sent to an external storage (for example to a mobile phone and/or computing device of a caretaker and/or the user). In some embodiments time and/or dosage may be stored 109 in a volatile memory for example a volatile memory may have speed, power consumption and/or cost advantages of non-volatile memory. Alternatively or additionally, time and/or dose information may be stored 109 in a non-volatile memory. For example, storing 109 data in non-volatile memory may prevent loss of important information in case of a failure of the adjunct device (for example battery failure). Optionally, after discharging 108 is distinguished 106, the adjunct device may display 110 the time and/or dose of the most recent discharging. For example, the user may access the previous dosage and/or time information when he decides when and how much medicine to inject in the next dosage. Additionally and/or alternatively, after detecting injection of a current dosage, the adjunct device may zero 126 its dosage counter and wait until the user adds 116 a unit to the new dose.

In some embodiments, a sensor may distinguish a vibration that is not clearly recognized 121. Optionally the adjunct device with then estimate 113 the state of the injector. Optionally, the adjunct device may display a warning 122a that there was a problem with distinguishing 106 the source of a vibration. In some embodiments, the adjunct device may display 115 the estimated 113 state of the injector and continue to function normally. Alternatively or additionally, the adjunct device may wait for user intervention (for example to validate and/or deny the estimated 113 state). Alternatively or additionally, the adjunct device may continue functioning normally based on the estimated 113 state without showing any warning to the user.

In some embodiments, an adjunct device may have an error state. For example, as described above, an error state may occur when the adjunct device fails to distinguish 106 a source of a vibration. Alternatively or additionally, an error state may be stipulated when a discharge medicine is not detected within a fixed time threshold after adjusting 144 the device (for example adjusting 144 a device may include selecting a dosage). When a time out 123 period has past after distinguishing 106 adjusting 144 of a device without distinguishing 106 a discharge 108, an error state may occur. For example, on an error state a warning may be display 122b and/or the user may be notified and/or a caretaker may be notified. Alternatively or additionally the adjunct device may wait for a user intervention. Displaying 122a, 122b a warning may optionally include displaying a warning symbol and/or message on a display of the adjunct device. Alternatively or additionally, displaying 122a, 122b a warning may include displaying a warning symbol and/or message on a display of another device. Alternatively or additionally, displaying 122a, 122b a warning may include playing a sound and/or an audio message on the adjunct device and/or a different device.

FIG. 1B is a flow chart illustrating a method for reporting a state of an injector using passive and/or optional active sensors in accordance with an embodiment of the current invention. In some embodiments, one or more passive sensors may be used to detect 102 activity of an injector. When activity is detected 102, the source of the activity may be distinguished 106 based on output of the passive sensors. Alternatively or additionally an active sensor may be activated 104. The output of the active sensor may serve to improve distinguishing 106 of the activity that was detected 102 by the passive sensor. Alternatively or additionally, the output of the active sensor may be used to improve distinguishing 106 of future activity of the injector.

In some embodiments an active sensor may be activated 104 when activity of an injector is detected 102. For example, an active sensor may be activated 104 when an adjustment of the injector (for example subtracting 112 a unit from a dosage and/or adding 116 a unit to a dosage) is distinguished 106 from output of a passive sensor. For example, when a short click signal of a dosage adjustor is distinguished 106 (for example a signal whose amplitude decays more than 90% over 100 ms and/or a signal which is repeated while the device is held in approximately the same position and/or a signal whose source is from the region of the dosage adjustor [e.g. the proximal end of a pen injector] may be identified as a click from a dosage adjustor) then the sensor output is optionally differentiated between incrementing and/or decrementing a dosage. For example, an increase in dosage may be identified by a circumferentially oriented vibration in a first direction and/or a decrease in dosage may be identified by a circumferentially oriented vibration in a direction substantially opposite said first direction. For example a pulse width and/or an amplitude and/or a ratio of slopes (for example the ratio of the slope of a one portion of a wave to a later portion) may be used to differentiate an increase in dosage from a decrease. For example, upon detecting a pulse lasting more than a threshold time pulse width the dosage estimate may be adjusted in a first manner (for example incremented) and/or upon detecting a pulse lasting less than the threshold time pulse width the dosage estimate may be adjusted in a second manner (for example decremented).

In some embodiments, when a sensor detects that a unit was added 116 and/or subtracted 112 from the dosage, a counter may be incremented 118 and/or decremented 114 from a counter. Alternatively or additionally, an active sensor may be activated 104 when an ambiguous 120 output of the passive sensor is detected. While active, the active sensor optionally monitors 124 activity of the injector. For example, an optical sensor and/or a light source may be focused on a dosage adjustor, for example a dosage setting dial. For example, the active sensor may be able to distinguish movements of the dial associated with increasing a dosage and/or movements of the dial associated with decreasing a dosage.

In some embodiments, an active sensor may be deactivated 129. For example, deactivation 129 of an active sensor may occur when there has been a long delay 123 without detecting 102 activity (for example between 0.5 to 2 seconds and/or between 2 to 10 seconds and/or between 10 seconds to 1 minute and/or between 1 minute to 10 minutes and/or between 10 minutes to an hour). Optionally, a warning may be indicated 122*b* when there has been a long delay 123 after detecting adjusting of the injector without detecting 102 discharge 108. Alternatively or additionally, the active sensor may be deactivated 129 when a discharge 108 is distinguished 106. For example, after discharge 108 an injector, dosage data may be stored 109 and/or a current dosage counter may be zeroed 236 and/or an active sensor may be deactivated 129 until a further action is detected 102. Optionally the active sensor may remain active for a short time after discharge and then be deactivated 129 if there is no activity.

In some embodiments, an adjunct device may indicate when it distinguishes 106 an adjustment of the injector. For example, when an addition 116 of a unit is distinguished 106 from sensor output, the adjunct device may indicate 115 that dosage is increased for example by means of a sound and/or by displaying a symbol on the display of the adjunct device and/or on a display of an external device. For example, when a subtraction 112 of a unit is distinguished 106 from sensor output, the adjunct device may indicate 115 that dosage is decreased for example by means of a sound and/or by displaying a new dosage and/or symbol the display of the adjunct device and/or on a display of an external device.

In some embodiments, a control signal may be communicated 127 to the adjunct device. For example, a control signal may include instructions to modify 125 a display contents and/or a light and/or to adjust a sensitivity of a sensor and/or to calibrate a dosage (for example reducing an estimated dosage and/or increasing an estimated dosage for example to agree with the known dosage and/or the dosage indicator of the injector) and/or to set a time and/or to reset the device and/or to reset a dosage counter. For example control signals may be sent to modify 125 the device using an external device (for example a wireless communication from an external computing device and/or a wireless input device and/or a wired communication). Alternatively or additionally, the sensors of the adjunct device may be used to communicate control signals. For example clicking a dial of the injector in a predetermined pattern may cause the dosage to be calibrated up or down. Alternatively or additionally, the adjunct device may include a user interface.

Method for Monitoring Drug Administration

Figure 2A:
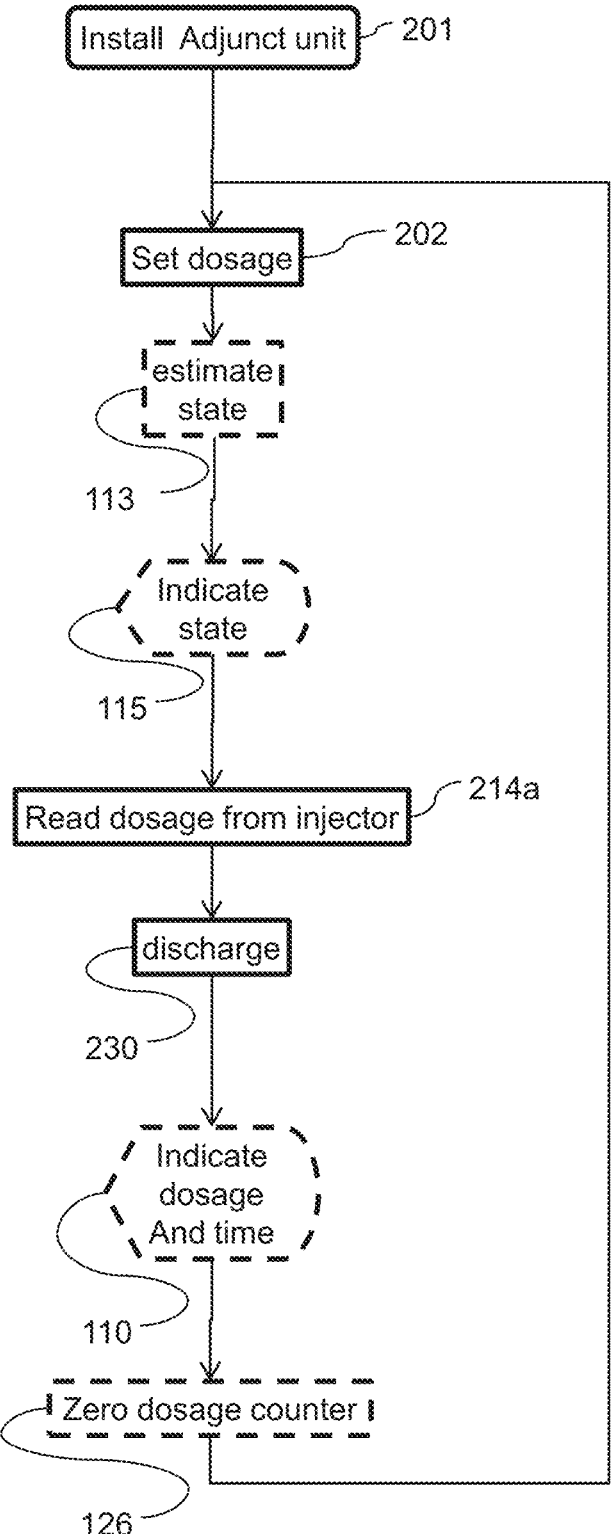
FIGS. 2A and 2B are flow chart illustrations of methods of monitoring drug administration in accordance with some embodiments of the current invention.
Figure 2B:
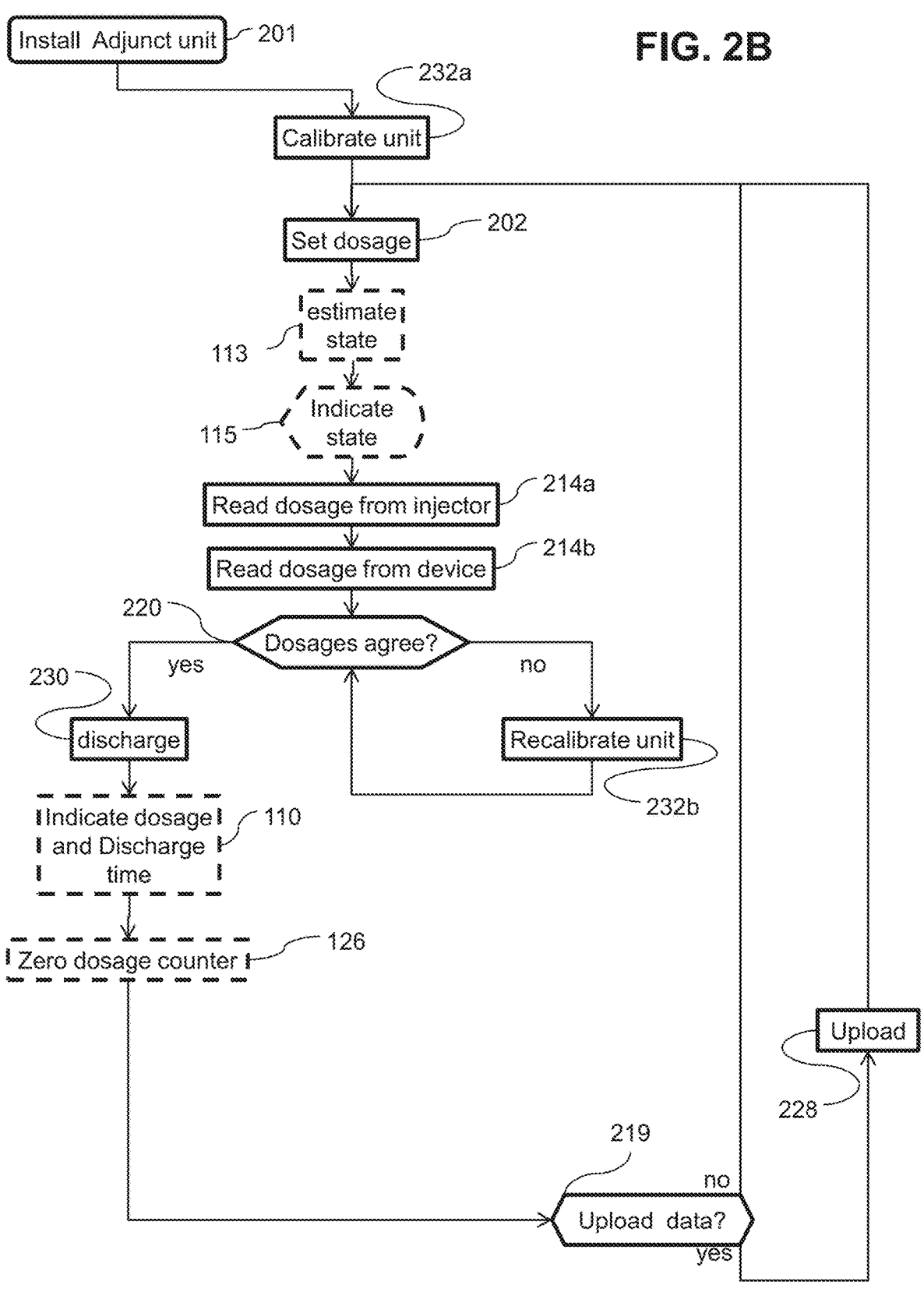

FIGS. 2A and 2B are flow chart illustrations of methods of monitoring drug administration in accordance with some embodiments of the current invention. In some embodiments, a user installs 201 the adjunct unit onto an injector and uses the injector exactly according to the manufacturer instructions while the adjunct device tracks dosage and injection times. Alternatively or additionally, various optional user steps are available for further functionality. In FIGS. 2A and 2B, actions that are in the exemplary embodiment automatically performed by the adjunct device are marked with dashed lines.

FIG. 2A is a flow chart illustration of a method of monitoring drug administration while operating a standard disposable injector according to manufacturer operating instructions in accordance with an embodiment of the present invention. Optionally, the adjunct device is installed 201 in a way that allows the user access to some or all of indicators and/or controls of the injector. In some embodiments, the dosage of the injector may be set 202 using the injector's native controls. For example, the injector may include a dosage dial that is rotated to set 202 a dosage. Optionally, the adjunct device detects setting 202 of the dosage and tracks changes in dosage without requiring direct user input. After setting 202 the dosage of the injector, the user optionally checks 214*a* the dosage on the indicator of the injector. When the user is satisfied that the dosage is proper he may discharge 230 the drug, for example by depressing an activation button of the injector. Optionally, the adjunct device detects discharge 230 and displays 110 the discharge time and dosage.

FIG. 2B is a flow chart illustration of a method of monitoring drug administration while operating a standard disposable injector according to manufacturer operating instructions and including optional additional user steps in accordance with an embodiment of the present invention. For example, the device is optionally calibrated 232*a*, 232*b*. For example, before injection, the user optionally checks 220 if the dosage displayed by the injector agrees with the dosage displayed by the adjunct device. Optionally, the user periodically uploads 228 data from the adjunct device to a personal computing device and/or to a shared database (for example a database of a doctor and/or a hospital and/or of a research institution.

In some embodiments, a user may calibrate 232*a* an adjunct device. For example, the device may be calibrated 232*a* when it is moved from one injector to another injector. Optionally the device detects when it is moved between injectors and/or notifies the user that he should calibrate 232*a* the device (for example the device may detect when the entire payload of an injector has been injecting based on the cumulative dose since the last calibration and/or there may be a sensor that recognizes when the adjacent device is clamped and/or declamped to or from an injector). Alternatively or additionally, the device may be calibrated every so often (dependent for example on a time interval and/or an amount of usage). Alternatively or additionally, the device may be calibrated at discretion and/or request of the user. Notification of the need to calibrated the device may be by an audible warning and/or a warning displayed on the screen of the adjunct device and/or via a secondary device (for example a notification displayed in a cell phone of the user for example when the user is uploading data from the adjunct device to the cell phone). An embodiment of a method of calibrating a device is illustrated in FIG. 9A.

Figure 10:
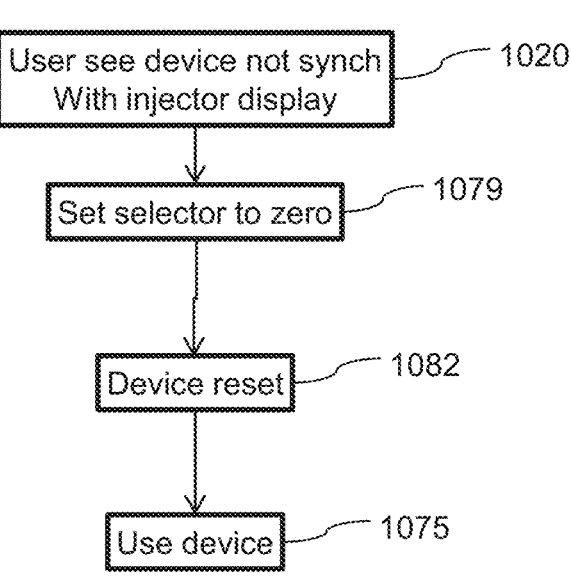
FIG. 10 is a flow chart illustration of a method of resetting a dose counter of a device for monitoring drug administration in accordance with some embodiments of the current invention.

In some embodiments, a user may check the proper operation of the adjunct device. For example, after setting 202 a dosage on the injector, the user may read 214*a* the dosage displayed by injector and read 214*b* the dosage indicated by the adjunct device. The user then checks 220 that the dosage displayed by the injector agrees with the dosage displayed by the adjunct device. Optionally, if the displayed dosages do not agree, the user may recalibrate 232*b* the adjunct device. For example the user may reset the dosage and/or correct the dosage counter of the adjunct device to agree with the injector. For example the device may include a user interface such as buttons and/or a rocker switch for adjusting the dosage counter. Alternatively or additionally the user may just write a reminder that the dose recording on the adjunct device is not accurate. An embodiment of recalibrating an adjunct device is illustrated in FIG. 10.

In some embodiments data may be uploaded 228 from an adjunct device to a database and/or a personal computing device. For example, the decision 219 to upload data may be automatic (for instance periodically) and/or a user may periodically give a command to upload 228 dosage and/or timing data to a cell phone and/or a personal computing device. For example, the data may be used to keep track of drug usage and/or effect. For example, the data may be used to adjust future usage. The drug usage data may be compared to diagnostic data (for example insulin usage data may be compared to measured blood glucose concentrations etc.). Optionally, the drug usage data may be made available to a medical supervisor (for example the user's personal doctor). Uploading 228 is optionally via a wireless connection, for example over blue tooth and/or another local connection and/or over a local area network (LAN) and/or over a cellular network and/or over a wired connection for example a USB cable and/or cradle. For example, the adjunct device may be charged and/or data may be uploaded 228 simultaneously. Optionally uploading 228 may be automatic when the unit is connected to a cradle and/or charged and/or connected via a wired connection to a computing device. Alternatively or additionally, uploading may be executed automatically periodically, for example once a day or more and/or between once a day and once a week and/or between once a week and once a month. Alternatively or additionally, uploading 228 may be performed when the device is calibrated and/or at a user command.

Dosage Monitoring System

Figure 3A:
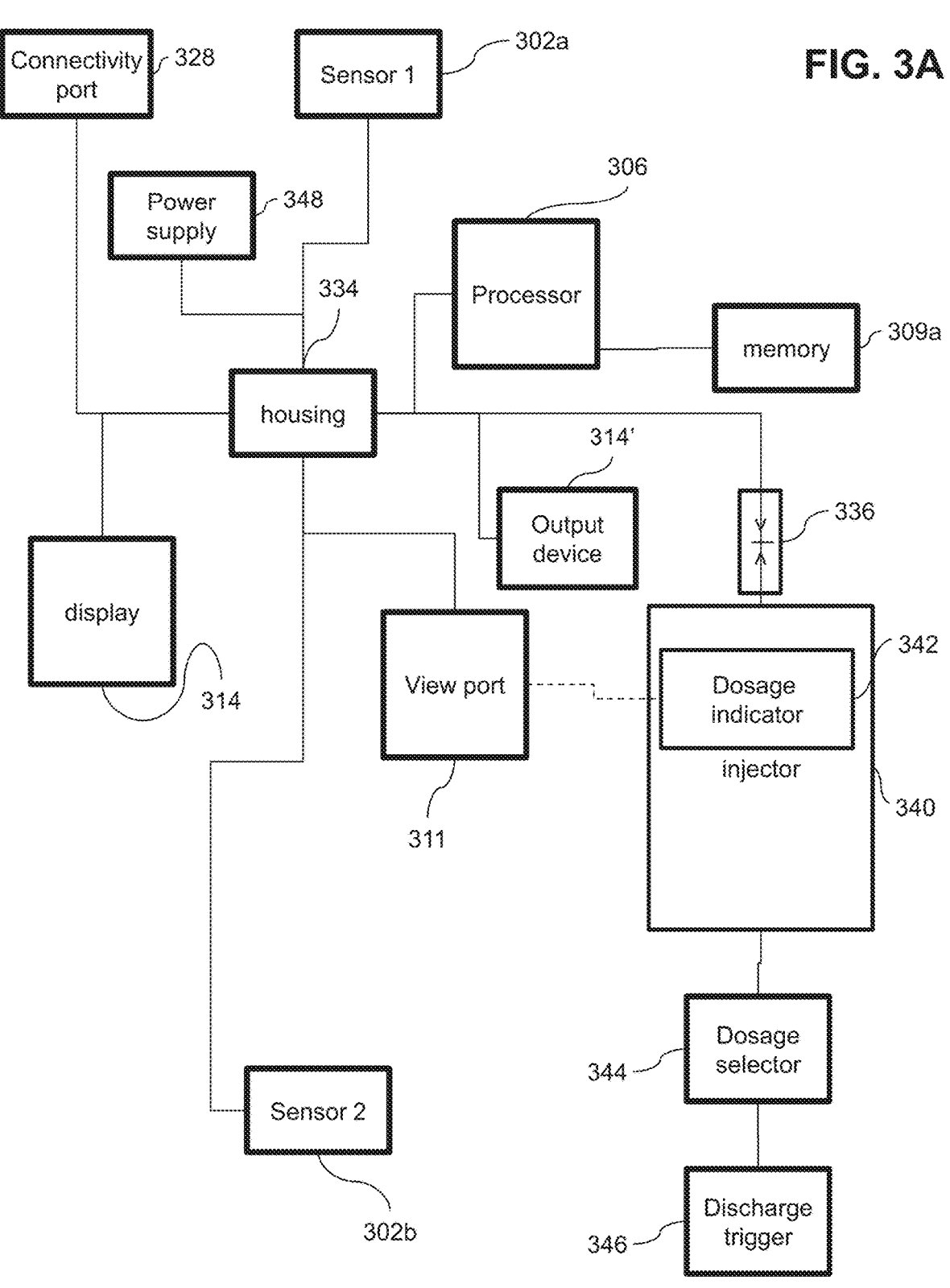
FIGS. 3A and 3B are block diagram illustrations of a device for monitoring drug administration in accordance with some embodiments of the current invention.
Figure 3B:
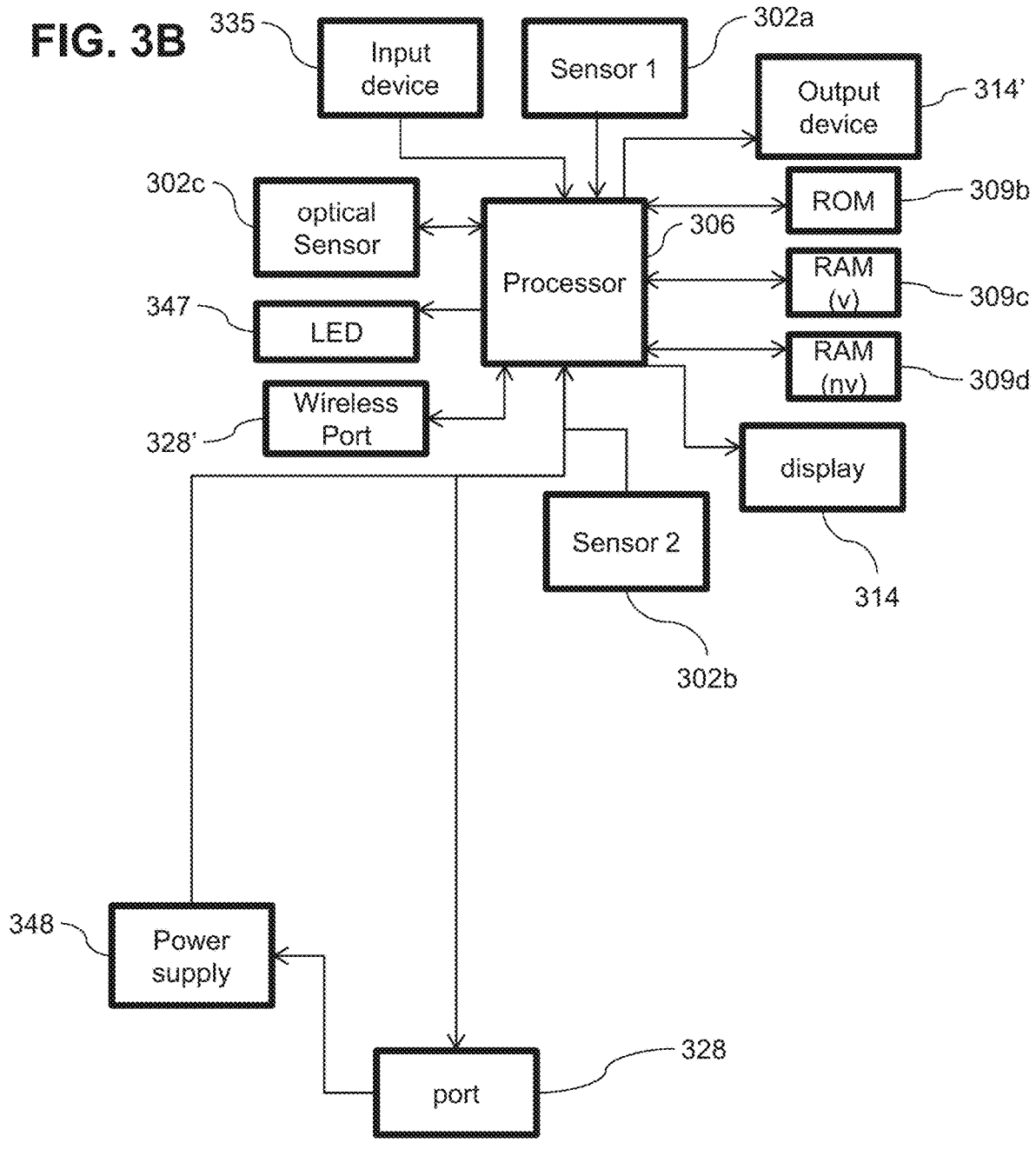

FIGS. 3A and 3B are block diagrams illustrating a system for monitoring injection dosage and/or timing in accordance with some embodiments of the current invention. In some embodiments, a system may include an injector and/or an adjunct device. In some embodiments, the adjunct device may include one or more passive sensors. The adjunct device optionally includes a processor operationally connected to the sensors for receiving sensor output and/or determining injector status and/or activity from sensor output. Optionally the adjunct device is mounted onto the injector in a manner that allows normal use of the injector. For example the adjunct device may allow user access to some and/or all controls and/or indicators of the injector.

In some embodiments, an adjunct device may include one or more sensors and/or sensor arrays, for example sensors 302a and 302b. Optionally for example, sensors 302a, 302b may include passive sensors (for example a piezoelectric vibration sensor) and/or low power sensors (for example an accelerometer and/or a microphone) requiring for example between 1 mW to 20 mW and/or 20 mW to 50 mW and/or 50 to 200 mW and/or 200 mW to 1 W. Alternatively and/or additionally the device may include an active sensor, for example an optical sensor and/or a light source.

In some embodiments, multiple sensors of a similar kind may be placed in different locations and/or different orientations. For example, one or more piezoelectric vibrations sensors and/or one or more accelerometers may be placed at different locations and/or different orientations. The signals of the different sensors may be compared for example in order to differentiate between different sources of vibration (for example to differentiate between random vibrations [for example due to dropping an injector 340 and/or tapping it on a table] and vibrations due to changing a dosage and/or vibrations due to injecting a dosage). For example different sources of vibration may be recognized based on characteristics of the vibration including the amplitude, frequency, rate of ramp up, rate of die off, damping. Alternatively or additionally different sources of vibration may be recognized based on comparison of characteristics of the signal between different locations and/or different axes (for example comparison of the above characteristics and/or comparing the phase between two locations and or between vibrations along two axes at one or more locations).

In some embodiments, multiple sensors of the same kind and/or measuring similar parameters may be located at different locations. For example, a vibration sensor (for example a piezoelectric sensor and/or an accelerometer and/or a microphone) may be placed on the distal end of the device (for example the distal end of the sensor may project distally beyond the distal end of the device and/or be located on the distal most 5% of the device and/or in a zone between 5 to 10% and/or between 10 to 40% of the length from the distal end to the proximal end of the device). Alternatively or additionally a second vibration sensor may be placed on the proximal end of the device (for example the proximal end of the sensor may projected proximally beyond the proximal end of the device and/or be on the proximal most 5% of the device and/or in a zone between 5 to 10% and/or between 10 to 40% of the length from the proximal end to the distal end of the device). Alternatively or additionally multiple sensors may be placed in the a similar circumferential position and/or may be offset circumferentially (for example the sensors may be offset between 0 to 10 degrees and/or between 10 to 80 degrees and/or between 80 to 100 degrees and/or between 100 to 170 degrees and/or between 170 to 180 degrees. Alternatively or additionally signals of different orientation may be compared at the same location and/or at different locations. For example, signals of different orientation may be measured at the same locations (for example by a multi-axes accelerometer) and/or at different locations (for example by a first vibration sensor at a first location in a first orientation and/or at a second location in a second orientation).

In some embodiments there may be different types of sensors. For example sensor 302a may include a vibration sensor and sensor 302b may include an optical sensor. Optionally, the device may use multiple sensors to save power. For example, a low power demand or passive sensor may be used to detect activity while a higher power demand sensor (for example an optical sensor with a light source) may be left un-powered until activity is detected. Alternatively or additionally, a low power and/or passive sensor may be used to detect activity and/or a high power demand sensor may be active when necessary to reduce doubt ambiguity (for example when a output of a vibration is not sufficient to differentiate between an increase and/or decrease of the dosage, an imaging sensor may be activated to read the dosage indicator 342 of injector 340. Other types of sensors that may be used may include a tactile sensor (for example a hairs that responds to movements of a dosage selector 344) and/or an electric switch (for example a switch to turns on when a discharge trigger 346 is depressed and/or turns off when the trigger 346 is released). Optionally a microphone may be used to detect sounds of operations, for example when discharge of the drug occurs.

In some embodiments, an adjunct device may include a view port 311. For example viewport 311 may include an open window through the device to a see a feature of the injector (for example dosage indicator 342 and/or the drug and/or the presence of bubbles etc.). Alternatively or additionally the device may be placed on injector 340 such that it doesn't block the feature. For example, the adjunct device may be placed on injector 340 entirely distal to dosage indicator 342. Optionally, view port 311 may include an opening through which a feature of injector 340 is visible.

Alternatively or additionally, view port 311 may include a pane and/or a reflector and/or a refractor (for example a lens may magnify dosage indicator 342 for example to make is easier to read and/or a prism and/or a minor may be used to change the view angle and/or location for viewing dosage indicator 342) and/or the view port may include an element that offsets the viewing location of a feature of the injector. For example a prism may make it possible to view dosage indicator 342 at a different angle and/or location than without the adjunct device.

In some embodiments an adjunct device may include a display 314. For example display 314 may include a Liquid Crystal Display (LCD). For example display 314 may display a time (for example a current time, an elapsed time since a previous injection and/or a time of a previous injection). For example display 314 may display a dosage (for example the current dosage setting of the injector and/or a last dosage and/or a historical dosage and/or a fixed dosage value and/or a difference between a current dosage setting and a fixed dosage value and/or a difference between a current dosage setting and a fixed dosage value [for example a fixed dosage value may be a recommended dosage and/or a average dosage and/or typical dosage]). Optionally display 314 may display a status (for example a battery status and/or connection status and/or an error status). In some embodiments, display 314 is positioned so that it can be viewed simultaneously with dose indicator 342 and/or view port 311. For example dose indicator 342 and/or view port 311 may be located side by side (for example the distance between the closest edges may be between 0 and 5 mm and/or between 5 mm and 2 cm and/or between 2 cm and 5 cm and/or they may be viewable from the same viewing angle (for example the optimal viewing angle and/or a surface tangent at the center of display 314 and/or viewport 410a may be at angles different between 0 to 5 degrees and/or between 5 to 20 degrees and/or between 20 and 45 degrees). Alternatively or additionally view port 311 and display 314 may be offset from each other in angle and/or position (for example the optimal viewing angle and/or a surface tangent at the center of display 314 and/or viewport 410a may be at angles different between 45 to 90 degrees and/or between 90 to 180).

Optionally, the adjunct device may include a further output device 314'. For example, further output device 314' may include a vibrating component. Optionally, the vibrating component may include a vibrator and/or a sound generator for example buzzer (for example a piezoelectric buzzer), a piezoelectric sounder, a speaker and/or and electro-acoustic transducer. Optionally the vibrating component may be used for a silent vibrating notification and/or an audible alarm. Alternatively or additionally the vibrating component may be used for communicating audible indicators for example real and/or synthesized voice and/or recognizable tones such as an activation tone and/or a deactivation tone and/or an error tone. Alternatively or additionally, the adjunct device may include one or more light emitting diodes (LED's 347) for example for use as status indicators. Alternatively or additionally LED's 347 may serve as a light source for an optical detector 302c.

In some embodiments an adjunct device may include one or more ports. Optionally the device may include a hard-wired port 328. Optionally hardwired port 328 may be used for supplying power (e.g. recharging a battery) and/or communication. For example, hardwired port 328 may include a plug for a power cord and/or a communication cord to connect to a computational device and/or a network adaptor and/or a cradle connector and/or a cylindrical connector and/or a multi-pin connector and/or a phone connector and/or a USB connector and/or a micro USB connector and/or a SCSI connector and/or FireWire connector etc. Alternatively or additionally, an adjunct device may include a wireless port 328', for example a blue tooth port, an ultra wide band UWB port, a Wi-Fi port, and/or an infrared port etc.

In some embodiments an adjunct device will include a connector 336. For example a connector may connect the adjunct device (for example a housing 334 and/or base of the device) to injector 340. Optionally, the connector may be configured to hold the adjunct device in a fixed relation to the injector 340. For example, the connector 336 may include a quick release mechanism and/or an orientation mechanism (connected to a particular part of injector 340) that fixes the orientation of the adjunct device with respect to the injector. The connector is optionally configured to facilitate conveying vibration from the injector to the adjunct device. For example, the connector may hold a vibration sensor (for example the first sensor 302a and/or the second sensor 302b) tightly to the injector 340 so that vibrations of the injector 340 are felt by the sensor. For example, a connector may include a channel fit around delivery device and/or a padding that conforms to the delivery device and/or a flexible housing that conforms to the delivery device and/or a flexible housing that grasps the delivery device and/or a tightening mechanism and/or a threaded mechanism and/or a clamp and/or adhesive and/or a high friction surface.

In some embodiments, a connector 336 may be releasably connected to the device. For example, a clamp and/or an adhesive element may have a releasable connector to the device. For example, a disposable element may be permanently stuck to the injector and/or releasably attached to the adjunct device. Optionally the disposable element may include a vibration sensor.

In some embodiments, attachment between the injector and/or device may include a clamp and/or track and/or pin and/or a stud and/or an adhesive and/or a tie and/or a clip and/or a bushing and/or a rail and/or a foot and/or a threaded element and/or a rivet etc.

In some embodiments an adjunct device may include one or more input systems. For example, input to the device may be supplied via a linked computational device (for example over a hard wired or wireless port connection from a user device such as a personal computer, a smart phone, a tablet computer, a keyboard and/or a mouse). Alternatively or additionally input may be supplied via a dedicated input device (for example one of the sensors 302a, 302b) may be a dedicated input device. For example a dedicated input device may include a switch (e.g. a push-switch and/or a micro switch) and/or a light dependent resistor (LDR) and/or a thermistor and/or a photodiode and/or a phototransistor and/or an opto-isolator and/or a proximity switch and/or a reed switch. Optionally the adjunct device may have an input interface 335, for example including a touch screen and/or a button. For example, an adjunct device may include a power button, which may be used for example to turn the device on and/or off. For example, the adjunct device may include a pair of buttons for adjusting a dosage counter up or down (for example to synchronize the dosage counter with the dosage of the injector). Alternatively or additionally the adjunct device may include a rocker switch and/or other types of input devices. For example, input device 335 may be dedicated to adjusting up or down a dosage counter of the adjunct device. Alternatively or additionally, input device 335 may be used for different inputs at different times (for example depending on the state of the injector). Optionally display 314 and/or output device 314' may indicate to the user the current function of input device 335.

In some embodiments, the input system may include a dual use part of the adjunct device and/or injector. For example, the vibration sensor (for example sensor 302a and/or 302b) may be used for user input. For example, a user may convey a command to a vibration sensor by tapping the device and/or the injector (for example by tapping it on a surface e.g. a table and/or tapping it with another object e.g. a pencil). For example tapping the distal end of the injector on a table may turn on the device and/or tapping the proximal end of the injector on a table may turn off the device. Alternatively or additionally, a user may communicate with the vibration sensor of the device by manipulating a dosage selector 344 of the injector in a particular pattern. For example quickly twisting the dial of the injector back and forth may zero a dosage counter of the adjunct device. For example an accelerometer (e.g. sensor 302a, 302b) may be used as a dual purpose device. For example the accelerometer may be used to detect states of the injector (for example by sensing vibrations) and/or as an input device (for example the user may reset and/or activate and/or deactivate the device by turning it over and/or shaking it (for example shaking it longitudinally may have one meaning and/or shaking it laterally may have another meaning) and/or leaving it still for a certain period of time.

In some embodiments an adjunct device may include a processor 306 and/or a memory 309. For example, memory 309 may include read only memory ROM 309b and/or non-volatile random access memory RAM 309d and/or volatile random access memory RAM 309d. Optionally the device may include removable memory (for example a memory card) and/or fixed memory (for example on an internal chip). For example, basic programs of the device and/or data on one or more types of injectors may be stored on ROM 309b. For example, information one or more types of injector and/or calibration information (for example for a particular drug) and/or dosage and/or user information and/or an injection regime may be stored on RAM 309d. Transient information (for example about the current state of the device and/or the injector) may be stored in RAM 309c and/or RAM 309d.

In some embodiments, an adjunct device may include a power supply 348, for example including a rechargeable battery and/or a single use battery and/or a replaceable battery. Optionally the power supply may include an external power connection for example a solar cell and/or a charging port (for example a wired 328 and/or a wireless 328' charging port (for example an induction port)).

In some embodiments an injector 340 may include a disposable insulin injector (for example a Novo® Nordisk® FlexPen® and/or a Sanofi® SoloStar® and/or a Lilly® KwikPen®). Alternatively or additionally injector 340 may include a disposable injector of a drug other than insulin. Alternatively or additionally injector 340 may be single use, multi-use and/or refillable and/or may be any kind of drug delivery device for example a patch and/or an inhaler and/or an applicator and/or a testing device for example a sampler. In some embodiments, injector 340 may include a dosage selector 344 (for example a rotating dial). Optionally dosage selector 344 may make a characteristic vibration for certain actions (for example increase a dosage, decreasing a dosage and/or zeroing a dosage). In some embodiments, the injector may include a discharge trigger 346, for example a button. In some embodiments, the injector will include a dosage indicator 342, for example a number element visible through a window in the side of the injector. Dosage indicator 342 optionally displays the currently selected dosage of the injector.

Exemplary System

Figure 4A:
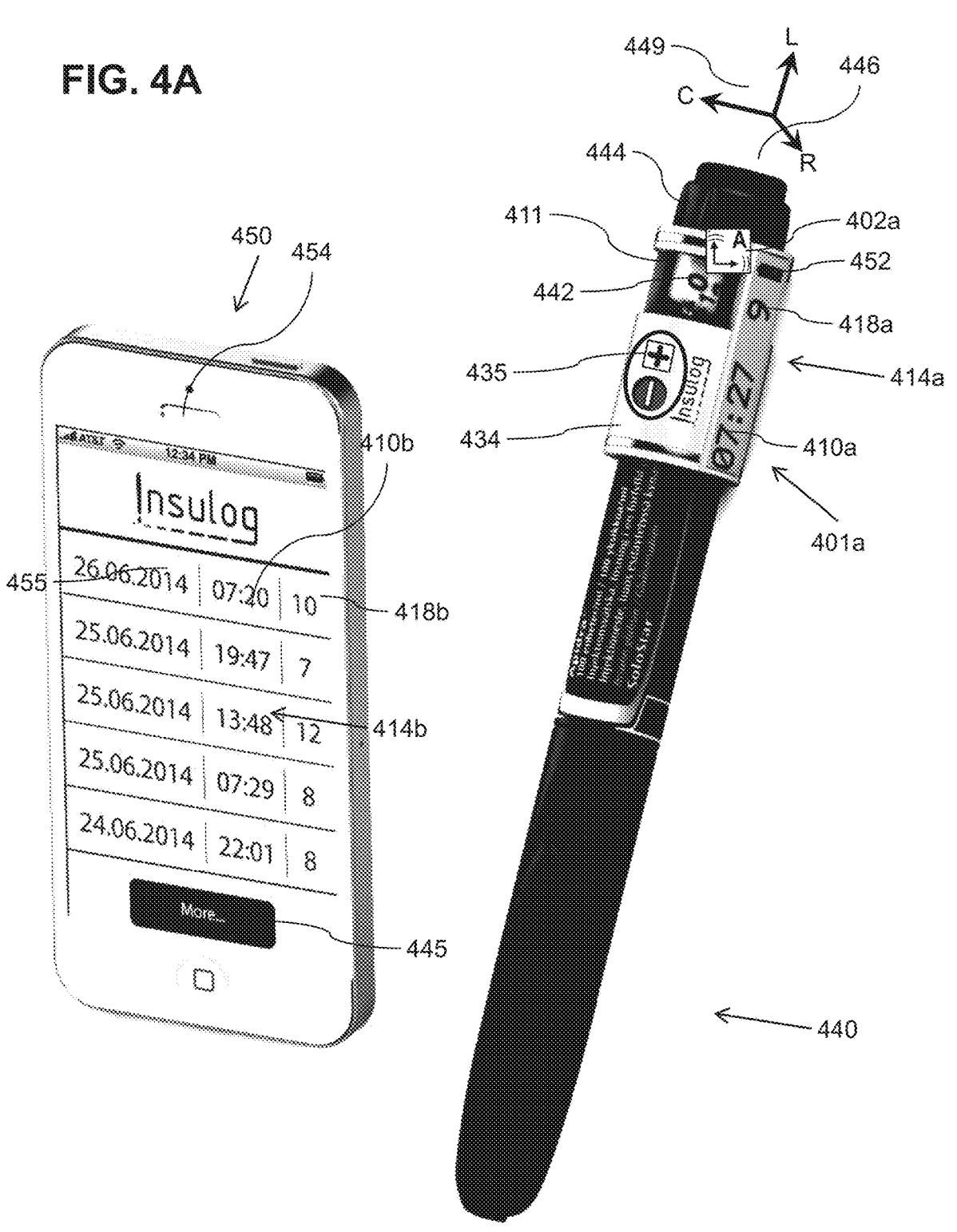
FIGS. 4A and 4B are perspective views of a system and device for monitoring drug administration in accordance with an embodiment of the current invention.
Figure 4B:
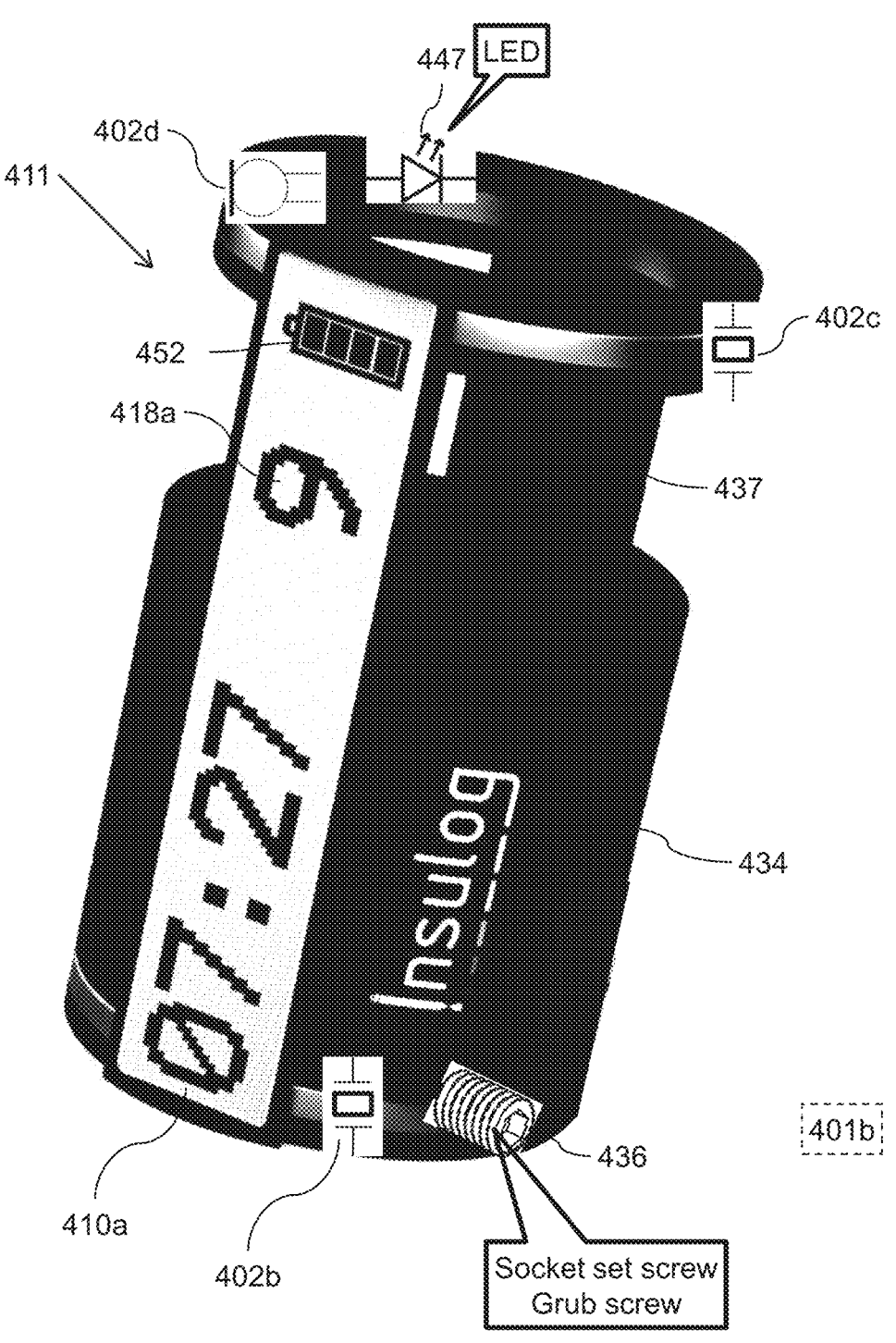

FIGS. 4A and 4B illustrate a system for tracking insulin injection in accordance with some embodiments of the current invention. Optionally the system includes an adjunct device 401a, 401b and/or a personal computing device 450 and/or an insulin injector pen 440 (in the exemplary embodiment of FIG. 4A, the injector pen 440 includes a Sanofi® SoloStar® injection pen). Optionally the controls and/or indicators of pen 440 remain visible and/or functional. Optionally adjunct devices 401a, 401b include a display 414a which is visible simultaneously with a dosage indicator 442 of pen 440. In some embodiments, device 401a may sense actions of injector 440 via a vibration sensor for example an accelerometer such as sensor 402a. Alternatively or additionally an adjunct device such as device 401b (e.g. see FIG. 4B) may include multiple vibrations sensors 402b and 402c and/or one or more optical sensors 402d.

In some embodiments, for example devices 401a and 401b, an adjunct device will not affect the functioning of an injector, for example injector 440. Optionally all of the indicators (for example a dosage indicator 442) and/or controls (for example dosage selector 444 (optionally including an adjustment dial) and/or discharge button 446) are accessible and function while device 401a or 401b is installed exactly as they functioned before installing adjunct device 401a or 401b.

In some embodiments, the adjunct device is configured to mount to a drug delivery device. For example adjunct devices 401a and 401b have the form of a ring and/or annulus. Optionally a drug delivery device, for example injector 440 fits into a channel 437 of the annulus. Optionally, for example as illustrated in FIG. 4A, device 401a includes a view port 411 through which a dosage indicator 442 of injector 440 can be seen. For example, in the exemplary embodiment, view port 411 includes an opening in the body 434 of device 401a. View port 411 is optionally positioned over indicator 442 when device 401a is attached to injector 440.

In some embodiments device 401a includes a display 414a. Optionally, display 414a is positioned adjacent to view port 411. Particularly, in the exemplary embodiment, the dosage counter 418a of display 414a is adjacent to the view port 411 of dosage indicator 442 of injector 440. Optionally, view port 411 and/or display 414a are angled to be visible at the same time from a single viewpoint. For example, when the adjunct device is attached to the delivery device a person may be able to see display 414a of the adjunct device and dosage indicator 442 of the delivery device simultaneously and/or without moving his head from a single vantage point. Optionally the vantage point may be distanced between 5 cm to 10 cm and/or between 10 cm to 25 cm and/or between 25 cm to 2 m from view port 411.

In some embodiments, an adjunct device may include an input interface. For example, device 401a includes a rocker switch 435. For example, rocker switch 435 may be used to adjust a dosage counter in the adjunct device. For example, when a user sees that dosage counter 418a is in error, he adjusts the dosage counter and/or counter 418a to the correct dosage using rocker switch 435. For example, in the dosage setting mode when dosage counter 418a of the adjunct device disagrees with dosage indicator 442 of the injector, the user optionally adjusts the dosage counter and/or dosage counter 418a to the value of dosage indicator 442. Alternatively or additionally, during the in between injection mode, when the user sees that dosage counter 418a lists a dosage that differs from the actual dosage of the last injection, he adjusts dosage counter 418a and/or the stored dosage of the last injection in adjunct device 401a and/or personal computer 450 using rocker switch 435. Alternatively or additionally a further button may be included. For example, an OK button may be supplied. For example, the user may push the OK button to store a time and dosage.

In FIG. 4A device 401a is illustrated in a between injection state. For example, device 401a may enter the between injection state after a first injection and remain in the between injection state until the user sets a dose for the next injection (for example in FIGS. 4A and 4B, dosage indicator 442 is in a zero state). Optionally, in the between injection state, display 414a includes a time section 410a wherein the time of the last injection is displayed (7:27) and a dosage section wherein a dose of the last injection (9 units) is displayed and a battery indicator 452.

In some embodiments, device 401a includes a single sensor, for example a two axes accelerometer 402a located near a dose selector 444 (for example near the proximal end of device 401 and/or injector 440). Optionally accelerometer 402a may include a gyro sensor. For example, the gyro sensor may be used to correct vibration measurements for example by removing acceleration measured due to changes of orientation to gravity. Vibration data from the two axes of sensor 402a are used by device 401a to distinguish raising a dosage, reducing a dosage and discharging insulin. Alternatively or additionally accelerometer 402a may include a three axis accelerometer. Axes 449 illustrate the directions with respect to device 440 at the position of accelerometer 402a. Particularly, the longitudinal L, radial R, and circumferential C axes are shown.

In some embodiments adjunct device 401a and/or 401b may communicate dosages and/or timing and/or other information to a personal computer 450 (for example a cell phone) of a user. For example computer 450 may include a touch screen display 414b and/or a virtual buttons 445. For example, devices 401a and 401b optionally communicate with computer 450 may be used to store and/or display historical dosage data and/or warnings and/or alarms and/or other messages. For example, in FIG. 4A, computer 450 displays a table of injection data for three days. For example, the table includes the date 455 time 410b and dosage 418b of each of a number of previous injections. Display 414b may also be used to display more complex written messages. Computer 450 includes an audio output device such as a speaker 454. Speaker 454 may be used to communicate for example an alarms and/or a voice message.

In some embodiments, for example as illustrated in FIG. 4B, an adjunct device may include multiple sensors. For example, device 401b includes two vibration sensors 402b and 402c and an optical sensor 402d. Optionally, sensors 402b and 402c may include piezoelectric vibration sensors. Sensors 402b and 402c may optionally include passive sensors and/or low power sensors, using little or no power. Generally the combined output of the two sensors 402b, 402c may be evaluated to distinguish increasing of a dose, decreasing of a dose and/or drug discharge. Optical sensor 402d is optionally used to reduce uncertainty when sensors 402b, 402c give ambiguous readings (for example when it is difficult to distinguish between an increase in dosage and a decrease in dosage). For example sensor may distinguish the direction of movement of dosage selector 444. For example, optical sensor 402d may track movement of lines on the dial of selector 444. For example sensor 402d may work like an optical mouse. Optionally, device 401b includes in LED 447 which illuminates selector 444 facilitating optical recognition of movement by sensor 402d.

In some embodiments, a light source may be used in conjunction with an optical sensor. For example, LED 447 may be activated when sensors 402b and/or 402c distinguish an adjustment of the dosage. For example, the first movement of the selector 444 may be sensed only by sensors 402b and 402c. When sensors 402b and/or 402c sense activity, LED 447 may be activated. Further movements of selector 444 may be sensed by sensors 402b, 402c and 402d. For example, where there is some ambiguity it may be assumed that the first movement of selector 444 is from a zero dose to minimum dose (for example a 1 unit dose). Optionally, during prolonged periods on inactivity, LED 447 may be deactivated. For example, deactivating LED 447 may save power.

In some embodiments, device 401b may include a socket set screw 436 and/or a grub screw to tighten device 401b to injector 440. Alternatively or additionally other fasteners and/or attachment means may be used to tighten device 401b to an injector. Optionally other mixtures of sensors may also be used.

Connectors

Figure 5:
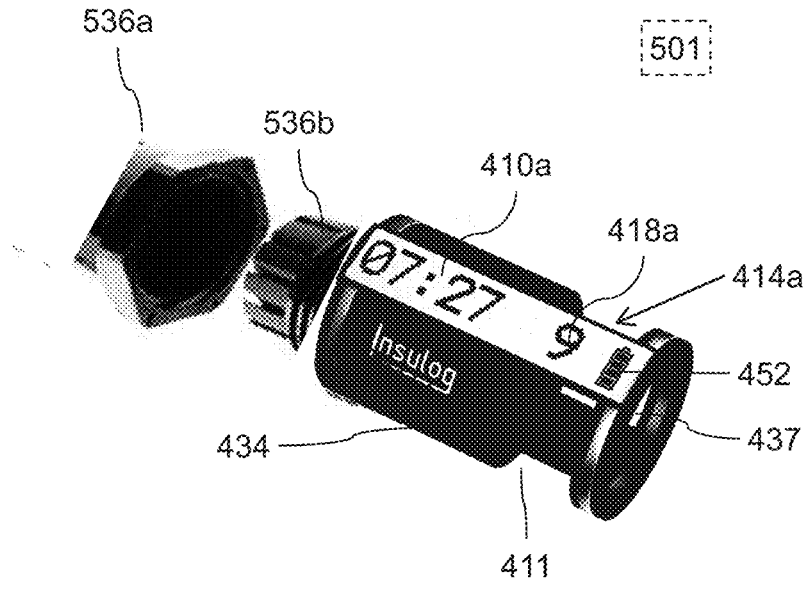
FIG. 5 is a perspective view of a device for monitoring drug administration including a threaded sleeve clamp in accordance with an embodiment of the current invention.
Figure 6:
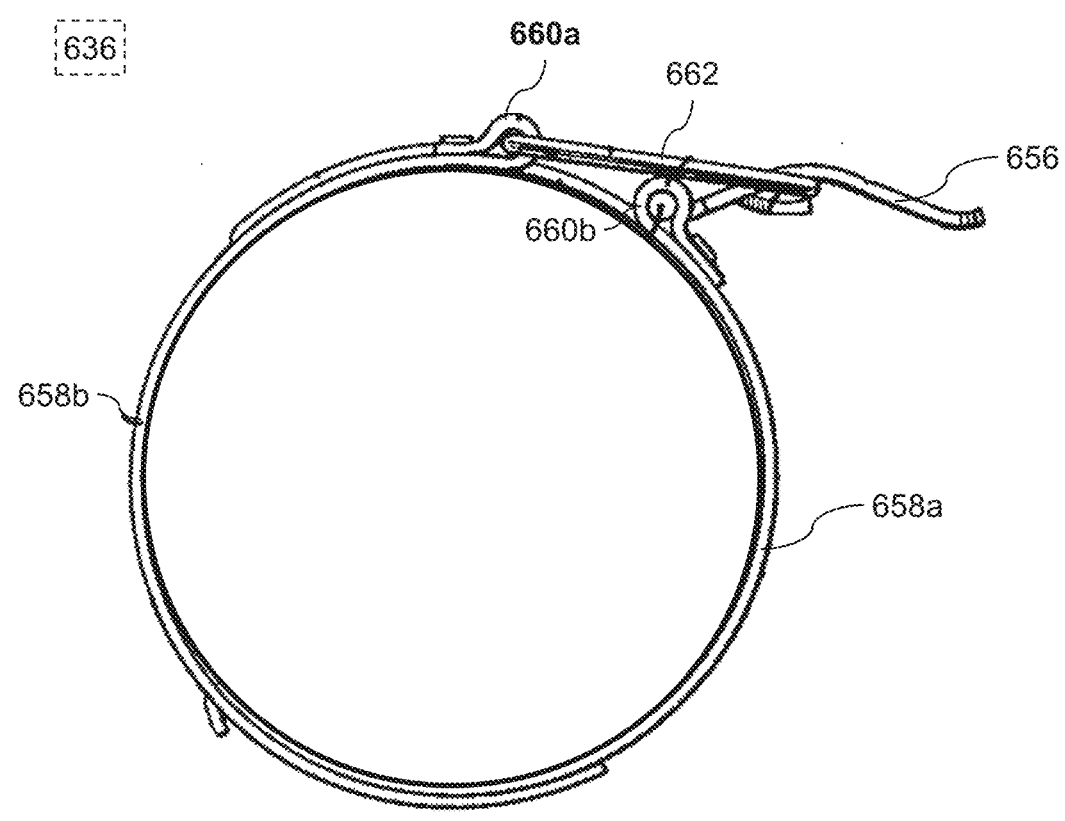
FIG. 6 is a perspective view of a quick release spring clamp in accordance with an embodiment of the current invention.

FIGS. 5 and 6 illustrate connectors for clamping an adjunct device to an injector pen in accordance with some embodiments of the current invention. In some embodiments a connector may keep an adjunct device fixed on an injector and/or position the adjunct device properly on the injector and/or facilitate transfer of vibrations between the injector and a vibration sensor of the adjunct device. For example, a connector may be configured to hold a vibration sensor tight to the injector and/or to determine a resonance frequency and/or a free length of a vibrating element.

FIG. 5 illustrates an adjunct device 501 with a sleeve clamp mount in accordance with an embodiment of the current invention. Optionally the sleeve mount slides over the body of the injector and is tightened to the injector using a threaded cap 536a wedged over a clamping claw 536b (for example like a cable gland). Optionally a vibration sensor is held to the injector by clamping claw 536b. For example a mounting portion of the vibration sensor may be positioned between clamping claw 536b and the outer wall of the injector.

FIG. 6 illustrates a quick release clamp connector 636 in accordance with an embodiment of the present invention. Optionally, connector 636 clamps an adjunct device to an injector. For example, a locking collar of connector 636 may be placed around the injector and/or a flexible portion of the adjunct device that is positioned around the body of the injector. For example the collar may be rounded and/or may include one or more pieces [for example collar pieces 658a and/or 658b]. A handle 656 may then be used to tighten the collar over the injector, holding the adjunct device and/or a vibration sensor to the injector. For example, handle 656 may include a lever rotating around a hinge 660b. For example handle 656 may pull an extension 662 connected to the collar by a second hinge 660a tightening the collar onto the injector and/or the device. Optionally a mounting portion of a vibration sensor may be positioned between the clamp and the injector. Optionally the collar may be tightened using a threaded element. A connector optionally may include a spring clamp, an elastic element, a cinch clamp, a retaining couple, a half coupler, a sleeve coupler, an ear clamp, a screw clamp, a wire clamp, a saddle clamp, a pinch clamp, a split wall clamp, a worm drive clamp and/or a clip.

In some embodiments, an adjunct device may include a detachable connector. For example, different connectors may be used to connect the adjunct device to different kinds of delivery devices. Optionally the connector may be disposable. Optionally the connector may include a permanent and/or irreversible coupling to the drug delivery device (for example an adhesive coupling). Optionally one or more sensors may be mounted on the connector. For example, the connector may include a communication port and/or plug, such that when the adjunct device is mounted to the delivery device by the connector the adjunct device receives data from the sensor of the connector.

States of a Device

Figure 7:
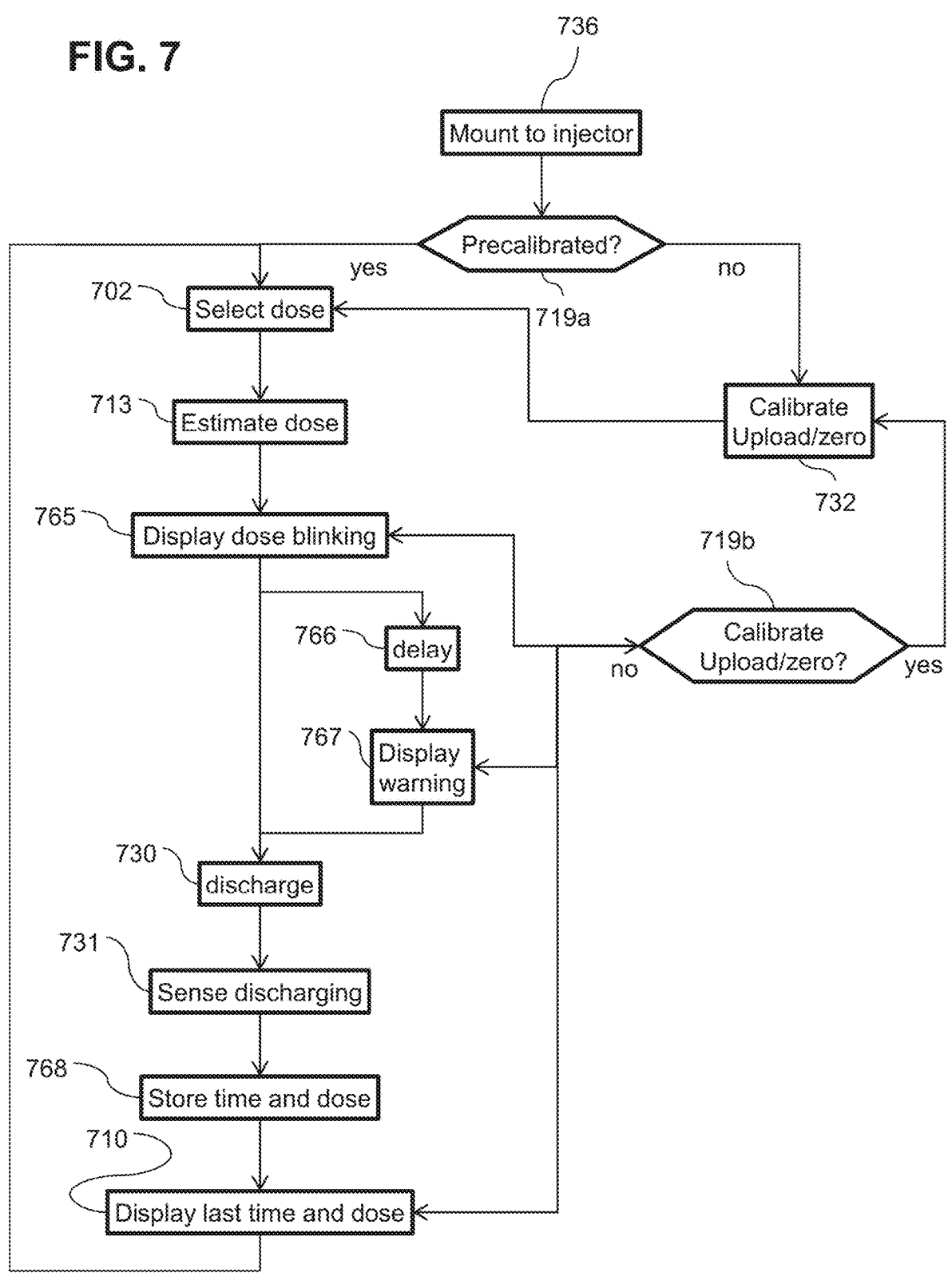
FIG. 7 is a flow chart illustration of states of monitoring drug administration in accordance with some embodiments of the current invention.

FIG. 7 is a flow chart illustration of state of an adjunct device for monitoring drug administration in accordance with some embodiments of the current invention. In some embodiments the device may be calibrated to a particular user and/or a particular injector and/or particular conditions. Alternatively or additionally the device may be precalibrated for a type of device and/or for all devices.

In some embodiments, an adjunct device may be supplied separate from an injector. For example the injector may include a disposable injection pen. Before use the adjunct device may be mounted 736 to the injection pen. For example mounting 736 may include sliding the adjunct device onto the pen and/or clamping the device to the pen.

In some embodiments, the device may be precalibrated 719a to distinguish various activities of the pen. For example, the device may include one or more vibration sensors and/or a processor configured to distinguish characteristic sounds of a certain kind of injection pen and/or one or more optical sensors to determine a state of the injector. Optionally, a precalibrated 719a device may be mounted 736 onto the pen and immediately used without user calibration.

In some embodiments, an adjunct device may not be fully precalibrated 719b. Optionally the device is calibrated 732 after mounting 736 to a pen and before use to distinguish characteristic vibrations made by a particular pen and/or by a pen under use by a particular user. For example, after mounting 736 the device to the injector, the device may be calibrated 719a.

In some embodiments, a user starts an injection by selecting 702 a dose. The injector senses selecting 702 of the dose and estimates 713 the dosage based on output of one or more sensors. Optionally, as the user selects the dosage, the device displays blinking 765 the estimated dosage on the device display. Optionally, the user simultaneously sees the dosage indicator of the injector. For example, in some embodiments, if the user sees that the dosage indicator of the injector is not in agreement with the dosage displayed by the adjunct device, he may choose 719b to calibrate 732 and/or to zero the device and/or the injector. Alternatively or additionally, the user may want to look at his injection history. For example, the user may choose 719b to upload 732 dosage data from the adjunct device to a personal computing device for viewing the data. Optionally, the adjunct device will signal that the dosage is in transition, for example, the dosage indicator may blink 765 while the dosage is being adjusted.

In some embodiments, after a dosage has been selected 702, a user may discharge 730 the contents of the injector (e.g. inject the drug). Upon discharge 730, the adjunct device optionally senses 731 the discharging and/or stores 768 the injected time and/or dose and/or enters the between injection mode. For example, in the between injection mode, the adjunct device may display 710 the time and/or dose of the last injection. In the between injection mode, the device may wait for selecting 702 of the next dose. For example, a passive and/or low power vibration sensor may continue to sense vibrations associated with selecting 702 of a new dose. For example, active sensors (for example an optical sensor and/or an associated light source) may be deactivated to save power.

Sometimes, there may be a delay 766 between selecting 702 the dose and discharging 730 the drug. Optionally in such a case, the adjunct device may display 767 a warning that the injector has been primed, but the injection has not been performed. Optionally the warning may be a visual warning (for example a blinking symbol on the display of the device and/or lighting a LED). Alternatively or additionally, the warning could be an audible warning (for example an alarm and/or a synthesized voice message).

In some embodiments, an adjunct device may optionally be recalibrated and/or data may be uploaded to a user's personal computing device and/or the adjunct device may be zeroed. For example, at various points (for example as illustrated in FIG. 7 during selection and/or in the between injection mode) the device may be recalibrated and/or zeroed and/or data may be uploaded. Optionally, actions may be at the discretion of the user. For example the user may initiate zeroing of the device by quickly turning the dosage selector of the injector up and down and/or the user may initiate calibration by tapping the device on a hard surface and/or the user may initiate data upload by shaking the device and/or the user may initiate any of the above functions by entering a command into a personal computer that will communicate the command to the device. In some embodiments, data uploading and/or calibration may be initiated automatically and/or remotely.

In some embodiments, communication may be suspended at times with the personal computer to save power. In such a case the user optionally gives a command to the device to initiate communication before beginning any communication or command sequence between the device and the personal computer. Optionally, calibration and/or upload may be automatically initiated periodically, for example between once a day and once a week and/or between once a week and once a month. Alternatively or additionally, data may be uploaded automatically when the free memory of the device is low. Alternatively or additionally a caretaker of the user may request and/or initiate an upload and/or update of dosage data remotely. In some embodiments, automatic uploading of data may require user approval of a user and/or a remote caretaker. Alternatively or additionally automatic uploading may proceed without requiring approval and/or invisibly.

Data Transfer

Figure 8:
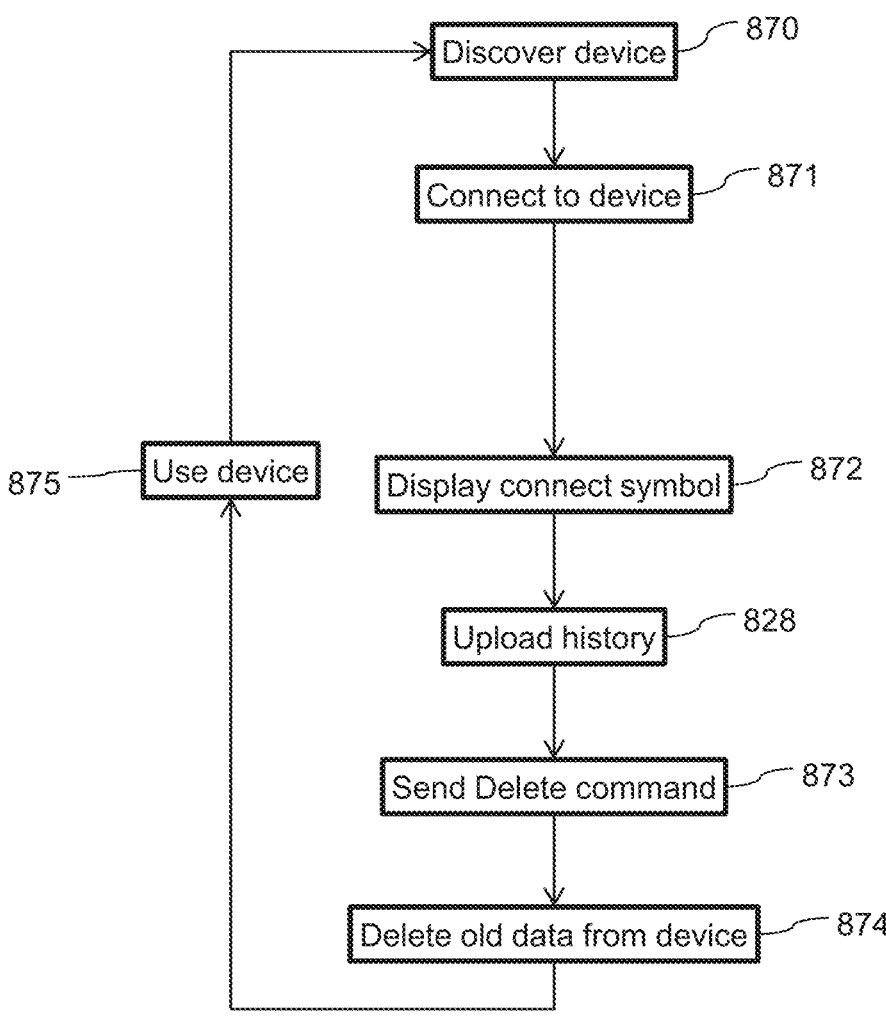
FIG. 8 is a flow chart illustration of a method of synchronizing a device for monitoring drug administration with a personal computing device in accordance with some embodiments of the current invention.

FIG. 8 is a flow chart illustration of transferring data in accordance with an embodiment of the current invention. For example, an adjunct device may connect to a personal computer of a user (for example a cell phone and/or a tablet and/or a laptop and/or desktop etc.). A connection may be over a data transfer channel directly to the personal computer of the user, for example via a hard wired connection (for example a cradle and/or a cable) and/or a wireless connection (for example Bluetooth). Alternatively or additionally, the device and/or data transfer channel may be connected to a hardwired network (for example a hard wired Local Area Network (LAN) port) and/or via a wireless network for example Wi-Fi. For example the device may be connected to the personal computer of the user via the network. Optionally the network and/or the personal computer of the user may supply a connection to another computer for example the computer of a caretaker.

In some embodiments a wireless connection between an adjunct device and a personal computer will remain constantly open. Alternatively or additionally, the wireless connection may be opened and/or closed according to need, for example to save power. When a connection is opened the network and/or host computer (for example the personal computer of the user) optionally discovers 870 the device and/or connects 871 to the device. Optionally, the device may have a connection status indicator. For example an LED indicator may indicate status and/or a network status symbol may be displayed 872 on the display of the device.

Optionally the status indicator may be displayed 872 in some or all states of the device. Optionally, there may be a network menu and/or set state of the device when network settings are displayed and/or adjusted. Additionally or alternatively, a connection status may be displayed 872 during the between injection state and/or the dose setting state. For example when the device is connected to a host computer and/or a network a connected symbol may be displayed 872. Alternatively or additionally, while the device is open to a connection a connection symbol may be displayed 872 (for example a Bluetooth symbol) even when the device is not actually connected to a remote and/or host computer.

In some embodiments, when uploading is initiated, the dosage history in the device may be uploaded 828 to the host computer. Optionally the host computer will send 873 delete command to clear the memory of the adjunct device. For example, upon receiving the delete command all or some of the stored dosage data in the device may be deleted 874. For example, data may be deleted back to a certain date and/or all data before a certain number of dosage events and/or all data before the last dosage event may be deleted 874. Optionally deletion 874 may be automatic every time data is uploaded 828. Alternatively or additionally deletion 874 may require user approval and/or a special command from the user. Alternatively or additionally deletion 874 may be dependent on a command and/or programmed instruction from the host computer. Optionally, before uploading 828, after uploading 828 and/or during uploading 828, the user may use 875 the device as described herein above and/or below. In some embodiments, while data is being uploading, the device may not be available for use.

Calibration of the Device

In some embodiments, an adjunct device for tracking dosage may be configured for user calibration and/or recalibration. For example a device may be calibrated to recognize vibrations associated with various functions of an injector. Alternatively or additionally a device may be precalibrated before reaching a user.

In some embodiments, a device may be recalibrated when it is moved from one type of injector to another type of injector (for example to adjust the device for differences between types, models and/or brands of injectors accordingly for example the device may be calibrated when it is first used). Alternatively or additionally, each device may be precalibrated for a particular injector type and/or each device may be used only with one type of injector. Alternatively or additionally a single device may be reprogrammed (e.g. by downloading software) and/or may be connected to a new hardware (for example a different connector) for use with different injector types. Alternatively or additionally, the device may be recalibrated when switching between one injector and another injector of the same type (for example when one injector is replaced by another injector of the same type for example when the medicine runs out) for example to adjust the device for differences between individual injectors of the same type and/or to adjust the device for differences in the connection (for example a slight difference in positioning and/or tightness of the connector).

Accordingly the device may be recalibrated for example automatically whenever the connection is changed and/or when the device is zeroed and/or after a certain number of injections and/or after a certain volume of injection etc. and/or on demand of the user. Alternatively or additionally the device may be calibrated to a particular user for example accounting for differences in the way the user holds and/or manipulates the device. Accordingly the device may be calibrated at the beginning of use and/or recalibrated on demand of the user. Alternatively or additionally, calibration of the device may account for changes in the performance of an injector between when it is fully filled and partially empty and/or environmental changes (for example temperature) and/or for other occurrences such as knocks (which for example may loosen a connector etc.). Accordingly the device may be calibrated for example after a fixed time period and/or number of injections and/or quantity of injection and/or on demand of the user and/or based on a parameter (for example a change of environment e.g. temperature) measured by a personal computer of the user. Alternatively or additionally calibration may be performed when it becomes apparent that the device is consistently erring in its estimation of actions, for example a user may demand a recalibration when he sees consistent errors and/or the device may automatically initiate recalibration when it detects too many resets of the device and/or the dosage selector.

FIG. 9A illustrates calibration of a vibration sensor of device in communication with a personal computer in accordance with an embodiment of the current invention. For example after discovering the device and or connecting to the personal computer and/or while the device is connected to the computer, the phone may instruct the user to perform various actions. The sensor output caused by these actions is optionally measured stored and/or analyzed for later use interpreting output of the sensor.

In some embodiments, during calibration, the personal computer instructs the user to increase 977 a dosage of the injector and/or a User then increases 977' the dosage. The sensor output resulting from increasing 977' the dosage is measured 977" stored and/or analyzed. Later when a sensor output is detected, the sensor response to increasing dosage is optionally detected, analyzed and/or used to interpret further sensor responses.

In some embodiments, during calibration, the personal computer instructs the user to decrease 978 a dosage of the injector and/or a User then decreases 978' the dosage. The sensor output resulting from decreasing 978' the dosage is measured 978" stored and/or analyzed. Later when a sensor output is detected, the sensor response to decreasing dosage is optionally detected, analyzed and/or used to interpret further sensor responses.

In some embodiments, during calibration, the personal computer instructs the user to decrease 979 a dosage of the injector to zero and/or a User then decreases 979' the dosage to zero. The sensor output resulting from decreasing 979' the dosage to zero is measured 979" stored and/or analyzed. Later when a sensor output is detected, the sensor response to decreasing dosage to zero is optionally detected, analyzed and/or used to interpret further sensor responses.

After calibration the device is optionally used 875 until it is decided 719*b* to recalibrate. If the device is still connected 919 to the personal computer, then calibration may proceed from the command to increase 977 dosage. If the computer is no longer connected 919 the device may be discovered 870, connected 871 and/or calibrated. Alternatively, the device may be calibrated without the connection to the personal computer, for example as illustrated in FIG. 9B.

For example the calibration data may be used to set a criterion for identifying actions based on sensor output. For example, criterion for distinguishing a click of a dosage adjuster may be modified based on calibration measurements of circumferential acceleration during increasing and/or decreasing a dosage. For example calibration measurements may be used to identify a pulse width. For example a range of measured calibration pulse widths may be used to adjust a range of pulse widths considered as dosage adjustment clicks. For example a range of measured calibration pulses widths for incrementing and decrementing may be used to adjust ranges of pulse widths considered as dosage incrementing and/or decrementing. For example a range of measured calibration pulses slopes and/or slope ratios for incrementing and decrementing may be used to adjust ranges of pulse slopes and/or slope ratios considered as dosage incrementing and/or decrementing.

Figure 9B:
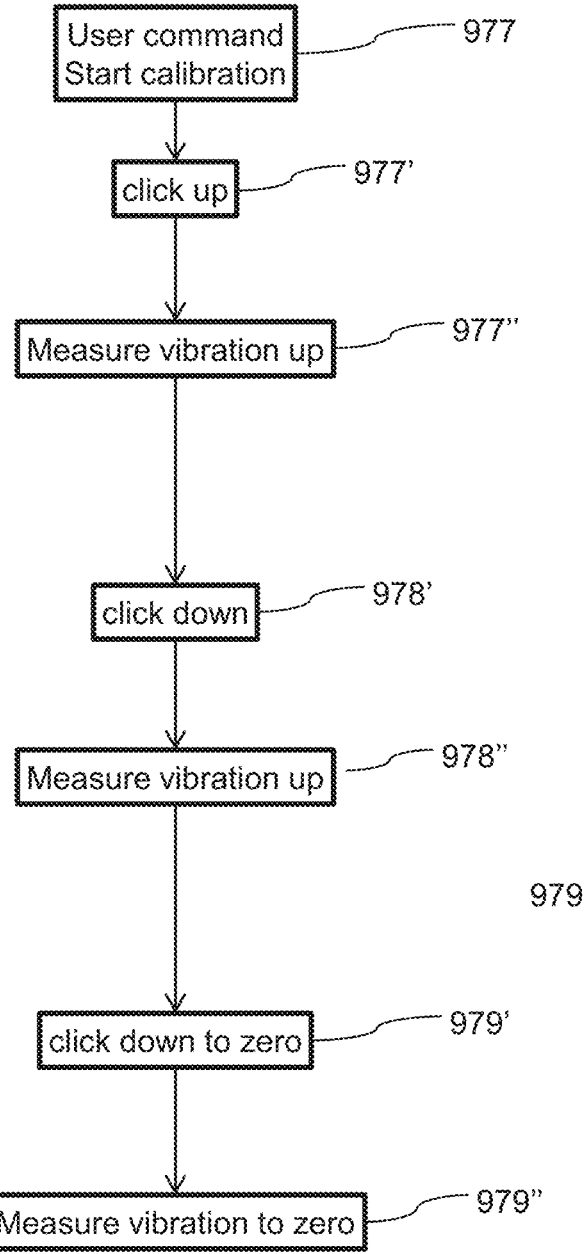

FIG. 9B illustrates calibration of a vibration sensor of device independently of a remote computer in accordance with an embodiment of the current invention. Optionally, calibration may be initiated by a user command 977 (for example the user may shake the device to start the calibration process) and/or the device may request that the user initiate calibration. Optionally, a message on the device display and/or a voice message and/or a coded message (for example via an LED) may prompt and/or instruct the user to perform a calibration and/or instruct him step by step what to do during calibration. Alternatively or additionally, calibration may have an ordered set of actions that the user carries out without prompting from the device.

FIG. 10 illustrates synchronizing a dose counter of an adjunct device to an injector in accordance with an embodiment of the current invention. At times a dose counter of an adjunct may become out of synch with a dosage of an injector. For example when a user notices 1020 that the dosage listed on the display of the adjunct device disagrees with the dosage listed on the dosage indicator of the injector he may initiate a synchronization process.

In some embodiments, synchronization may include zeroing the injector dosage and the dosage counter of the adjunct device. For example, the user may click and/or twist a dosage selection knob of the injector to set 1079 the dosage of the injector to zero. The user may then reset 1082 the adjunct device dosage counter to zero for example by turning off and on the device and/or by a pressing a reset button and/or by tapping the device on a hard surface in a predetermined pattern. Alternately or additionally the device may detect zeroing of the injector and/or automatically reset 1082. For example, to the zero the device, the user may quickly click down the selector of the injector over a large number of dosages. The fast clicking downward across multiple dosages may stimulate the device to reset 1082 automatically.

Figure 11:
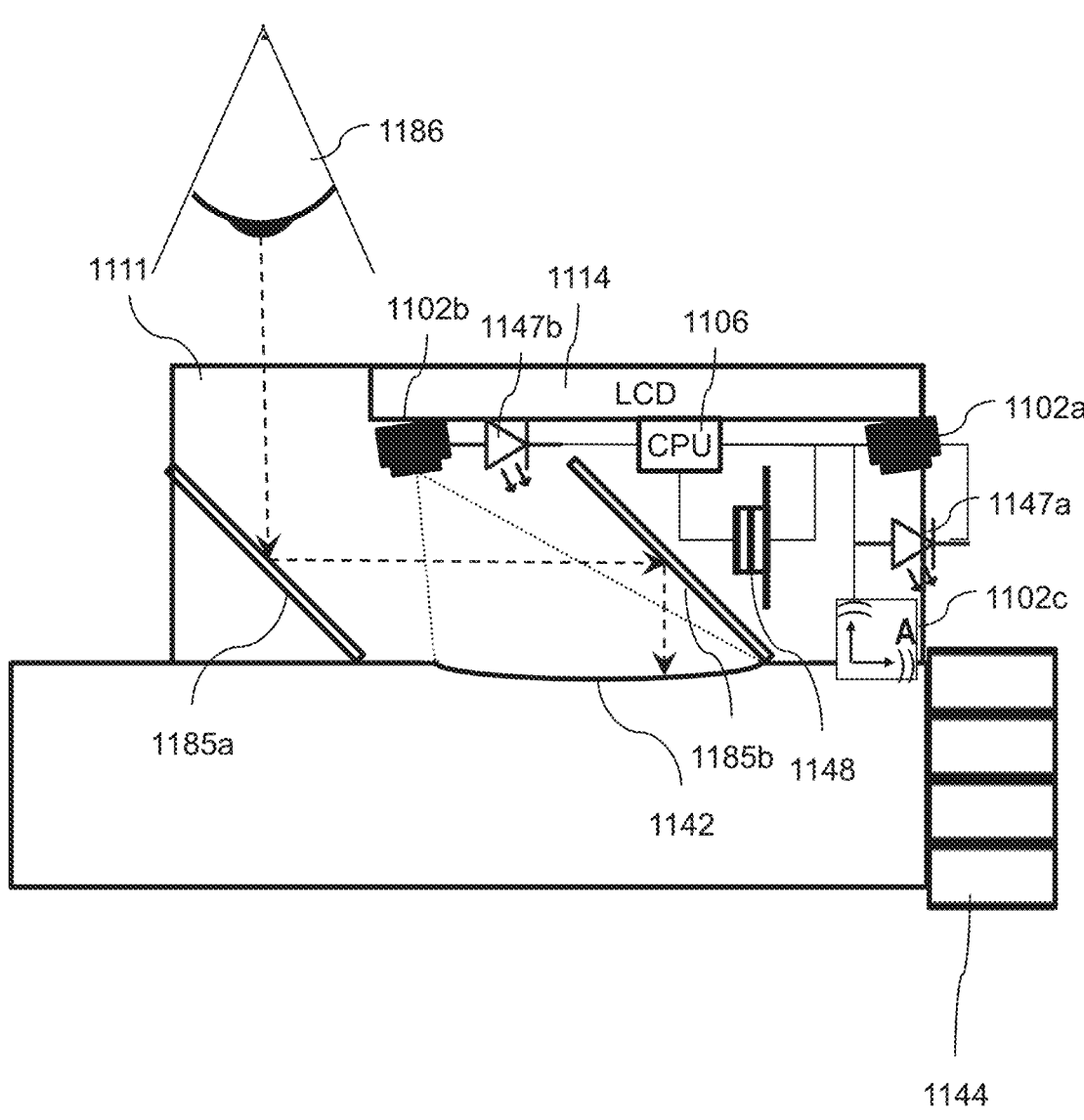
FIG. 11 is a schematic illustration of a drug administration monitoring device with an indicator displacing viewer in accordance with some embodiments of the current invention.

In some embodiments, there may be a coded signal to reset 1082 the adjunct device. For example, quickly clicking up a dosage a few units and immediately clicking back down may be a sign to the adjunct device to reset 1082. Optionally, the user may synchronize the injector and adjunct device at any time by quickly clicking up the does a few units and clicking it back to zero thereby simultaneously zeroing both the injector and the adjunct device. Once the injector and adjunct device are synchronized, the user may return to using 1075 the device normally. Optionally, when the device repeatedly gets out of synch, the device may be recalibrated.
Device with Repositioning View Port FIG. 11 is a schematic illustration drug administration tracking adjunct device with an indicator displacing view port in accordance with some embodiments of the current invention. Optionally, a view port of an adjunct device may include a light reflecting and/or refracting element to change the viewing position and/or angle of the dose indicator of the injector. For example a view port may include a pair of mirrors 1185a and 1185b that act like a periscope so that a dosage indicator 1142 may be viewed from a translated viewing location 1111 and/or view angle.

In some embodiments, from at least one vantage point one or more components of the adjunct device may block viewing of an indicator of the injector. For example an optical imaging sensor 1102b and/or light source 1147b and/or display 1114 may block view of a dosage indicator 1142 of the injector from a vantage point 1186. For example, imaging sensor may send image data to a processor 1106 that is used to read (for example using optical character recognition OCR) the dosage on indicator 1142. Optionally a viewport is supplied (for example a periscopic assembly including mirrors 1185a, 1185b translates a viewing location 1111 to a position that is not blocked. In some embodiments, the translation of the viewing of viewing location 1111 is with passive elements (e.g. mirrors 1185a, 1185b). Thus, the user actually sees indicator 1142 of the injector even if there is a malfunction of the adjunct device (for example a failure of a power supply 1148 and or display 1114 and/or the device misestimates the current dosage). Thus the viewport supplies a redundant and/or independent verification of the dosage of the injection in case of malfunction of the adjunct device. Optionally Display 1114 is located in a position that can be seen simultaneously with viewing location 1111. For example, by seeing both, a user may be able to verify that indicator 1142 and display 1114 show the same dosage for an injection.

In some embodiments, an adjunct device includes a vibration sensor. For example a two axis accelerometer located near the dosage selector 1144 of the injector. Alternatively or additionally an adjunct device may include an optical sensor 1102a and associated light source 1147a. For example, optical detector 1102a may be able to detect movements and/or direction of movement of lines on a dial of a dosage selector 1144 for example to distinguish increasing and/or decreasing of a dosage. In some embodiments an adjunct device may include a vibration sensor without optical sensors and/or with only one optical sensor (for example either a imaging sensor 1102b or a movement sensor 1102c)
Device with View Port Indentation FIGS. 12A-15 are perspective illustrations of drug administration tracking adjunct devices having a view port indentation, a dosage estimate adjustor and a discharge verification button in accordance with some embodiments of the current invention.

In some embodiments, an adjunct device (for example device 1201a) may include a delivery verification button 1235c. For example, when a user pushes button 1235c device 1201a saves a time (for example a displayed time 1210 displayed to the user on a device display 1214) and/or an estimated dosage (for example a displayed dosage 1219 displayed to the user on a device display 1214). Alternatively or additionally a dosage and/or a time of delivery may be stored automatically and/or without user verification. Optionally, displayed time 1210 is the time of last detected drug discharge. Alternatively or additionally, displayed time 1210 is the current time. Optionally, dosage 1219 is the estimated dosage of the last drug delivery. Alternatively or additionally, the estimated dosage is an estimate of the current dosage setting of a drug delivery device (for example the dosage currently displayed on dosage indicator 442 of insulin pen injector 440). Optionally the estimated dose may be a dosage counter 1218 value currently displayed to the user on a display 1214. For example, as explained in previous embodiments, the displayed dosage counter 1218 value may depend on the state of the adjunct device and/or the injector Some embodiments may include a user interface for adjusting an estimated dosage (for example buttons 1235a and/or 1235b). For example, a button 1235a may increment dosage counter 1218 of the adjunct device and/or a button 1235b may decrement the dosage counter 1218.

In some embodiments, a user control may have different functions depending on a state of the adjunct device. For example an injection verification button 1235c may be enabled when the device detects drug delivery. Optionally when the user presses verification button while it is enabled, the device stores the time and quantity of the previous discharge. Additionally or alternatively, after storing a time and dosage, discharge verification button 1235c may be disabled until a subsequent discharge is detected. Alternatively or additionally verification button 1235c may be disabled after certain error conditions. For example verification button may be disabled if it is not triggered before a predetermined time delay after discharge has been detected (such an error may be referred to as a time out error) and/or when following a drug discharge, a dosage setting is changed before storing discharge data (such an error may be referred to as an action out of sequence error). Alternatively or additionally, at certain times, triggering button 1235c may open a menu and/or verify a user choice in a menu.

In some embodiments, an adjustment control 1235a and/or 1235b may be enabled when the adjunct device detects a dosage adjustment and/or may be disabled when the adjunct device detects a drug delivery. Alternatively or additionally, when the adjunct device is in a waiting state after delivery, buttons 1235a and/or 1235b may be used to page through a menu and/or a history of dosages and/or to adjust a previous stored time and/or dosage.

In some embodiments, a warning may be communicated to the user on certain conditions. For example a warning may be displayed if verification button 1235c is triggered while it is in a disabled state. For example a warning may be displayed when verification button 1235c is not triggered by the user after a drug discharge has been detected, for example, when verification button 1235c is disabled due to a time out error and/or an action out of sequence error. Optionally adjunct device may store warning conditions, for example, the device may store the type of warning, the time of the warning and/or the estimated dosage at the time of the warning.

In some embodiments, adjunct device 1201a may include a viewport 1211a indentation (for example to say that viewport 1211a may include a distal indentation in the proximal edge of adjunct device 1201a). For example, the proximal edge of device 1201a is located proximally to the distal edge of dosage indicator 442. Optionally a portion of the proximal edge of device 1201a includes an indentation (e.g. port 1211a) sized and shaped to allow a user to see dosage indicator 442 while device 1201a is mounted to injector 440. For example, the proximal edge of device 1201a does not reach the proximal edge of dosage display

Figure 12A:
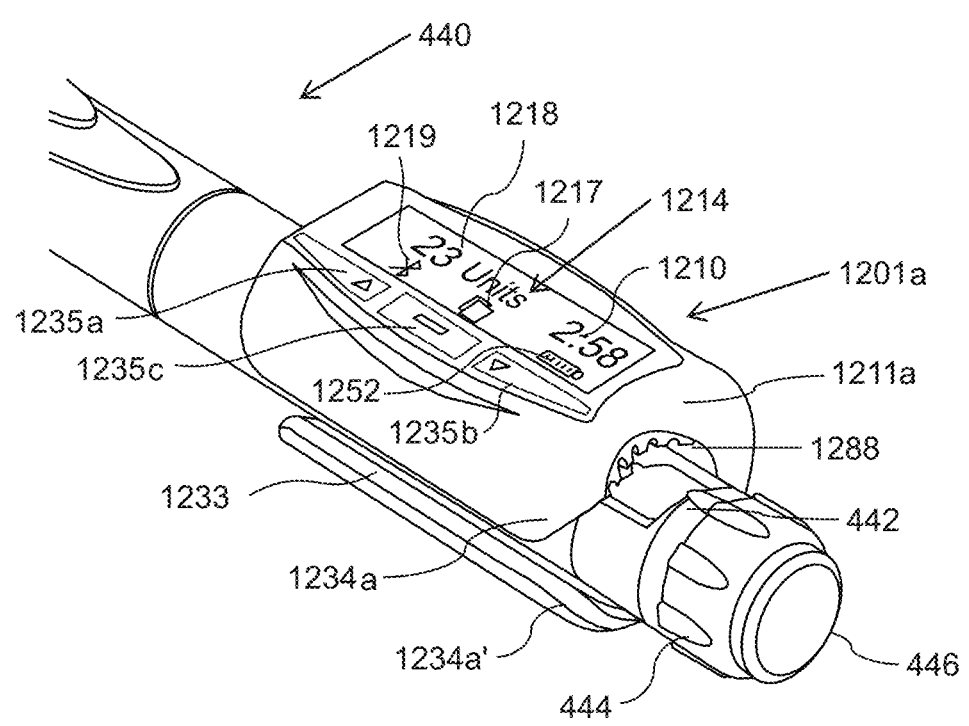
FIGS. 12A and 12B are perspective illustrations of a drug administration tracking adjunct device including a view port indentation, a dosage estimate adjustor and a discharge verification button mounted on an injector in accordance with some embodiments of the current invention.
Figure 12B:
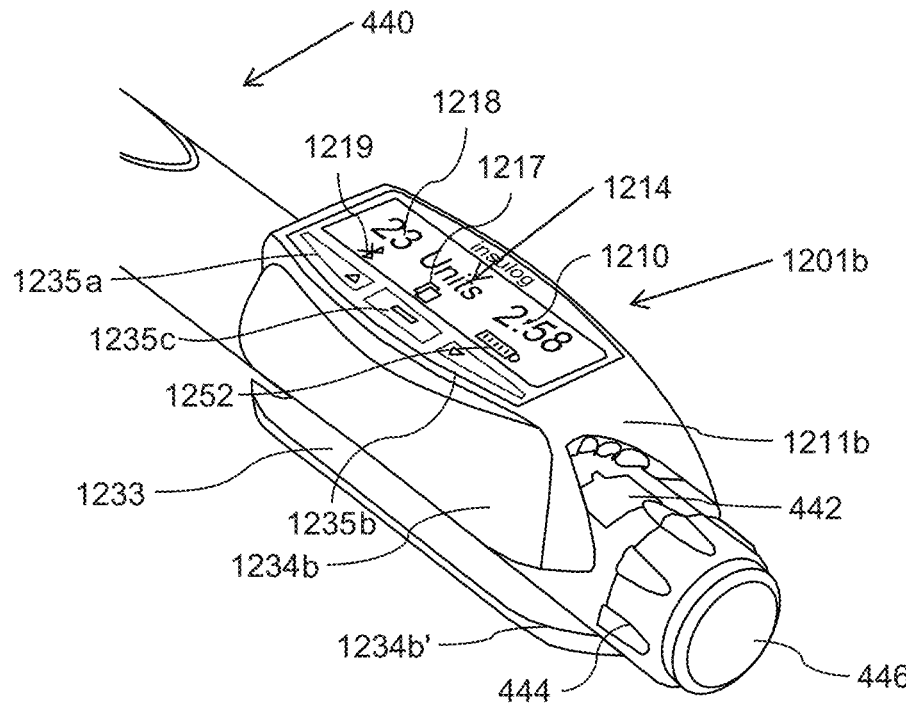

442. For example, view port 1211a partially surrounds dosage indicator 442. For example, view port 1211a partially surrounds dosage indicator 442 from three sides thereof. Alternatively or additionally, the proximal edge of a device 1201b (for example as illustrated in FIG. 12B) reaches and/or is proximal to the proximal edge of dosage display 442. For example, view port 1211b completely surrounds view port 411. For example, view port 1211b surrounds dosage indicator 442 from three sides thereof. Alternatively or additionally, (for example as illustrated in FIGS. 4A, 4B and 5) view port 411 may surround dosage indicator 442 from all sides thereof.

In some embodiments, the proximal edge of the adjunct device may reach within 0.5 mm of a distal edge of a dosage selector 444 and/or between 0.5 to 1 mm and/or between 1 to 3 mm and/or between 3 to 6 mm and/or between 6 to 12 mm of the distal edge of a dosage selector 444.

In some embodiments a housing of an adjunct device and/or a portion of the housing may have the form of an open ring and/or broken annulus. Alternatively or additionally the housing may have the form of a complete ring and/or annulus. The ring optionally surrounds a channel 1237. For example, devices 401a, 401b and 501 have a complete ring form and/or adjunct devices 1201a and/or 1201b have an open ring form. For example, an open ring may have a front section 1234a and/or a rear section 1234a' and/or a slit 1233.

In some embodiments, an adjunct device may grip a drug delivery device from opposite sides thereof. For example, injector 440 may be squeezed between front section 1234a and rear section 1234a'. Optionally, adjunct device 2101a may include padding 1288 in the space between the drug delivery device and the adjunct device. For example device 1201a includes padding 1288 between front section 1234a and the dorsal outer wall of injector 440. Optionally padding 1288 is elastically deformable (for example by compression between the outer wall of injector 440 and a contact surface of device 1201a [for example the inner annular surface of device section 1234a]). Optionally padding 1288 may be comprised of at least 90% and/or between 50 to 90% of an elastomeric polymer. In some embodiments the contact surface may be padded and/or coated with a non-slip coating. Optionally, padding 1288 deforms to fit different shaped delivery devices. For example, deformation of padding 1288 may facilitate a single adjunct device to fit more than one type of delivery device. Optionally, the inner and/or out surface of an annular adjunct device may be circular or non-circular. Alternatively or additionally, the housing of an adjunct device may be malleable enough to attach and/or deform to fit different delivery devices.

FIG. 12B illustrates an adjunct device 1201b in accordance with an embodiment of the current invention. Optionally, the proximal edge of a front section 1234b and a rear section 1234b' reach beyond the proximal edge of dosage indicator 442. A view port 1211b optionally completely surrounds dosage indicator 442. In some embodiments a view port may surround for example between 20 to 50% of the periphery of a dosage indicator and/or between 50 to 75% and/or between 75 to 100%.

Figure 13:
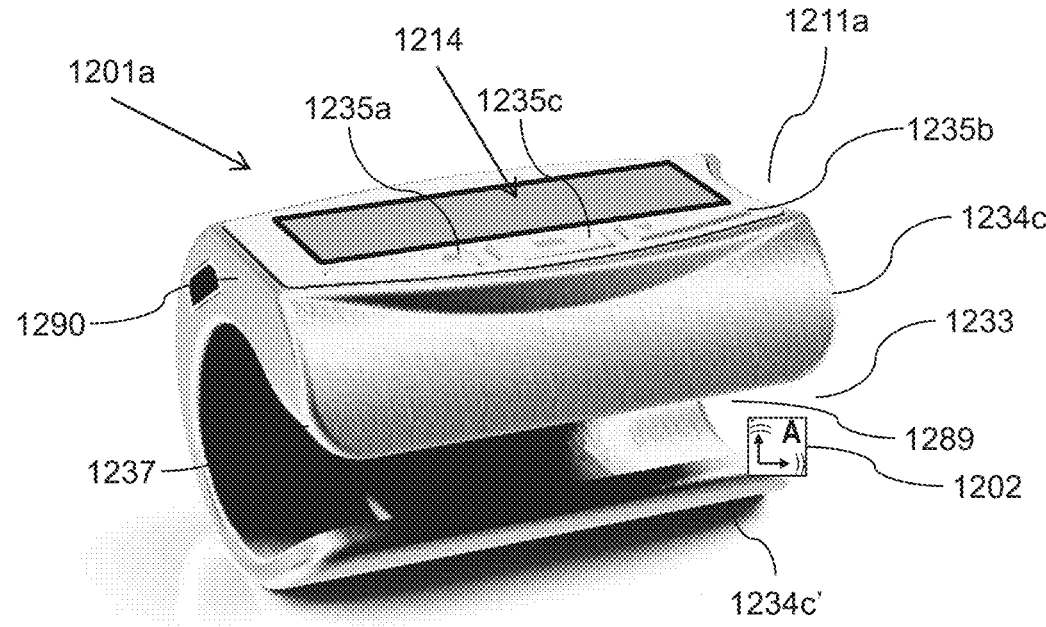
FIG. 13 illustrates a perspective view of a drug administration tracking adjunct device including a view port indentation, a dosage estimate adjustor and a discharge verification button in accordance with an embodiment of the present invention.
Figure 13:
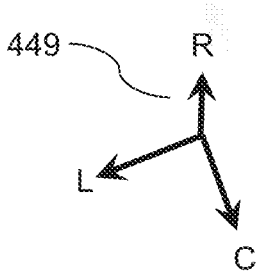

FIG. 13 illustrates a perspective view of device 1201a in accordance with an embodiment of the present invention. In some embodiments, a device may have the form of an open ring. The space surrounded by the ring optionally forms a channel fitting a drug delivery device. The housing of the adjunct device is optionally flexible such that it expands to fit around the drug delivery device and/or clamps onto and/or squeezes a delivery device inserted into the channel and/or deforms to fit the delivery device.

In some embodiments the adjunct device will include a plug in port. For example device 1201*a* includes a mini-USB port 1290. Port 1290 is optionally used for charging device 1201*a*. Alternatively or additionally, port 1290 may be used for communication with an external device, for example a personal computing device. Alternatively or additionally, a port may include a standard connector and/or a cylindrical connector.

In some embodiments the adjunct device may include a motion sensor and/or a vibration sensor. For example a motion sensor 1202 may be mounted inside the annulus of the adjunct device. Optionally, motion sensor includes an accelerometer and/or a gyro. For example the accelerometer 1202 may measure acceleration and/or rotation along and/or around one, two or three axes.

Figure 14:
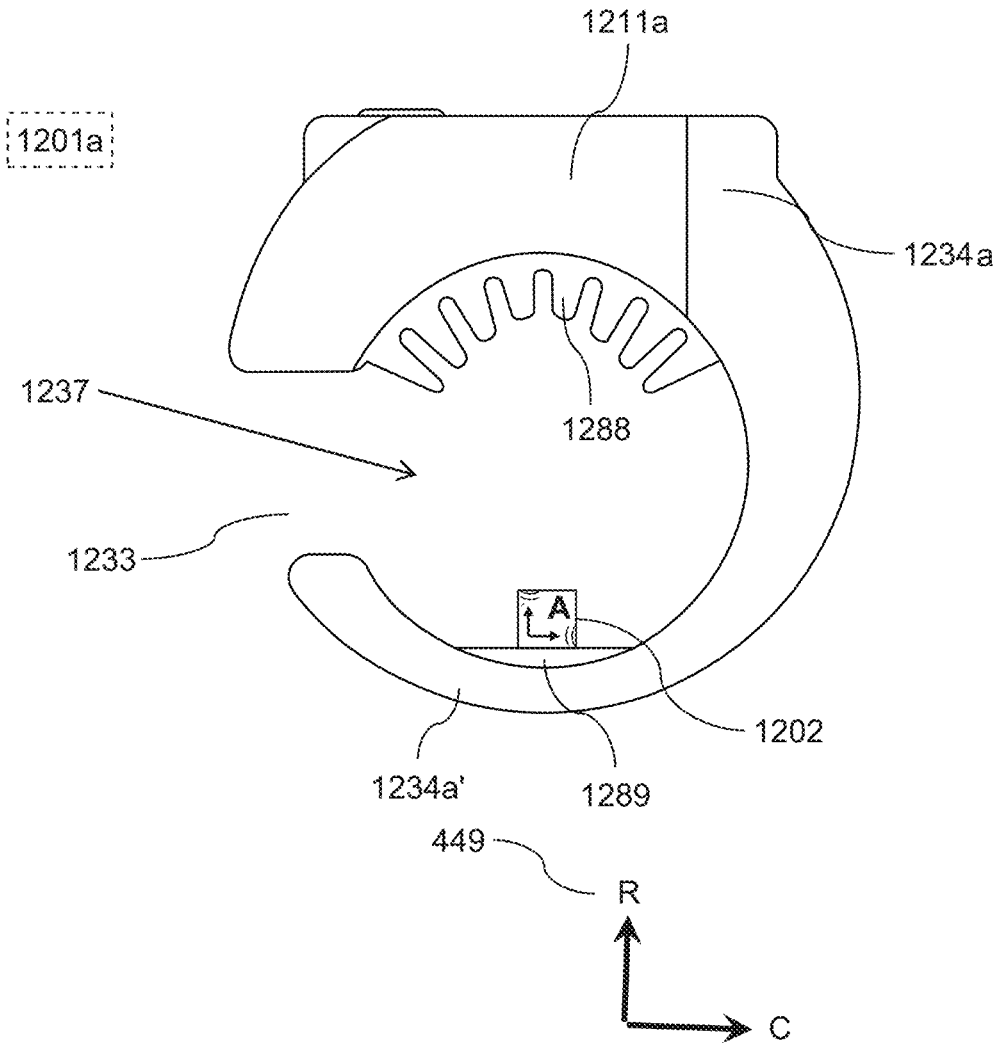
FIG. 14 illustrates a proximal end view of a drug administration tracking adjunct device in accordance with an embodiment of the present invention.

FIG. 14 illustrates a proximal end view of device 1201*a* in accordance with an embodiment of the present invention. In some embodiments the device may have a hard shell. The shell optionally has the form of an open and/or closed ring. Optionally a drug delivery device may fit into the space surrounded by the ring. For example, the inside surface of the ring and/or a portion thereof may form a contact surface with a drug delivery device. Optionally, a portion of the surface of contact between the device and the injector may include a padding. Optionally, a portion of the surface of contact may be hard and/or fit precisely to a drug delivery device, for example to fix the position of the adjunct device on the delivery device. Optionally the shell and/or the padding may be elastically deformable. For example, when a drug delivery device is inserted into the ring, the shell and/or the padding may be deformed and/or may compress onto the delivery device, grasp the delivery device and/or retain the delivery device and/or conform to the delivery device.

In some embodiment, one section of the adjunct device deforms and/or presses a delivery device against another section. Optionally, when a drug delivery device is inserted into channel 1237, channel 1237 elastically expands. For example, when a drug delivery device is inserted into channel 1237, rear section 1234*a*' elastically deforms away for front section 1234*a* (e.g. ventrally, rearward and/or downward in FIG. 14). Optionally, while the delivery device is inside channel 1237, elastic recoil forces rear section 1234*a*' towards front section 1234 (e.g. dorsally, forward and/or upward in FIG. 13). Alternatively or additionally, when the delivery device is inside channel 1237, the drug delivery device is pushed against padding 1288, compressing the padding. For example the recoil force of rear section 1234*a*' and/or elastic recoil of compressed padding 1288 clamp the delivery device inside adjunct device 1201*a*.

In some embodiments, a portion of the surface of contact between an adjunct device and a drug delivery device is hard (for example harder than a padded portion). For example the inside surface of rear portion 1234*a* is hard.

In some embodiments, a sensor 1202 is mounted to the surface of contact of the adjunct device to a drug delivery device. For example, sensor 1202 may be mounted to a hard surface (for example the inner surface of rear portion 1234*a*'). For example, mounting to a hard surface may avoid damping effects of padding 1288. Alternatively or additionally, sensor 1202 may be held against the delivery device by padding 1288. For example, padding 1288 may press sensor 1202 against a housing of the delivery device. Alternatively or additionally, a probe may connect sensor 1202 to the delivery device. For example, adjunct device 1201*a* may retain the probe in contact with the delivery device.

In some embodiments, a surface of contact of an adjunct device to a drug delivery device may include a fitting. For example, a fitting 1289 fits a rear surface of a drug delivery device. Optionally fitting 1289 may be configured to hold sensor in a particular orientation and/or with a particular force to the drug delivery device. Optionally sensor 1289 is held close to a dosage selector of the delivery device. In some embodiments, a mount for a sensor, for example fitting 1289, may be located opposite a portion of the adjunct device (for example the proximal edge of front portion 1234*a*). Alternatively or additionally, a mount for a sensor may protrude towards the dosage selector. For example, rear section 1234*a*' and/or fitting 1289 may protrude proximally beyond the proximal edge of front section 1234*a* towards dosage selector 444.

In some embodiments, a padding may have a rough surface. For example, the inner surface of padding 1288 has protrusions. The protrusions are optionally be angled to give the padding an anisotropic friction coefficient with the delivery device.

In some embodiments, may include a thinner layer of padding 1288 and/or may not have a layer of padding 1288. Optionally, lessening the padding may cause the device 1201*a* to have a smaller width and/or profile. Optionally housing 1234*a*, 1234*a*' includes plastic and/or nylon. For example a nylon housing 1234*a*, 1234*a*' may be more flexible than a plastic housing. In some embodiments, the profile of device 1201*a* may be reduced, for example by moving the electronics (for example the processor and/or the power source) to a one location and display 1214 to a separate location.

Figure 15:
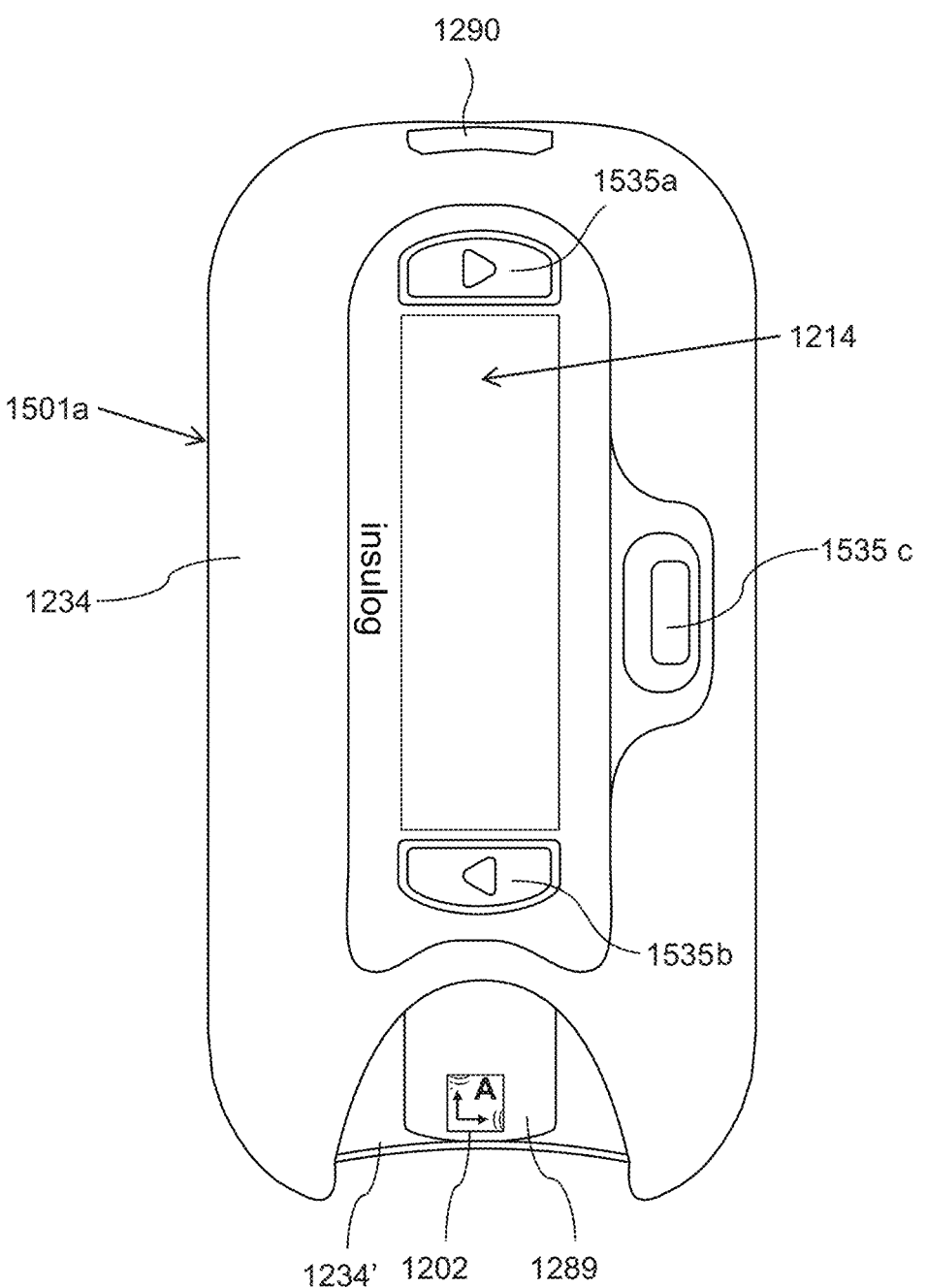
FIG. 15 illustrates an adjunct device having, a dosage estimate adjustor and a discharge verification button as three staggered buttons in accordance with an embodiment of the current invention.

FIG. 15 illustrates an adjunct device 1501 having three separate buttons 1535*a*, 1535*b* and 1535*c* in accordance with an embodiment of the current invention. For example, buttons 1535*a*, 1535*b* and 1535*c* may be separated into more than one row. Optionally separated buttons 1535*a*, 1535*b* and 1535*c* makes it easy for a user having limited dexterity to depress a selected button without interference from other buttons. For example, adjustment buttons 1535*a* and 1535*b* (e.g. for incrementing and/or decrementing an estimate dosage respectively) may be mounted on either side of a display 1214. For example, a verification button 1535*c* may be mounted above or below display 1214.

Figure 16:
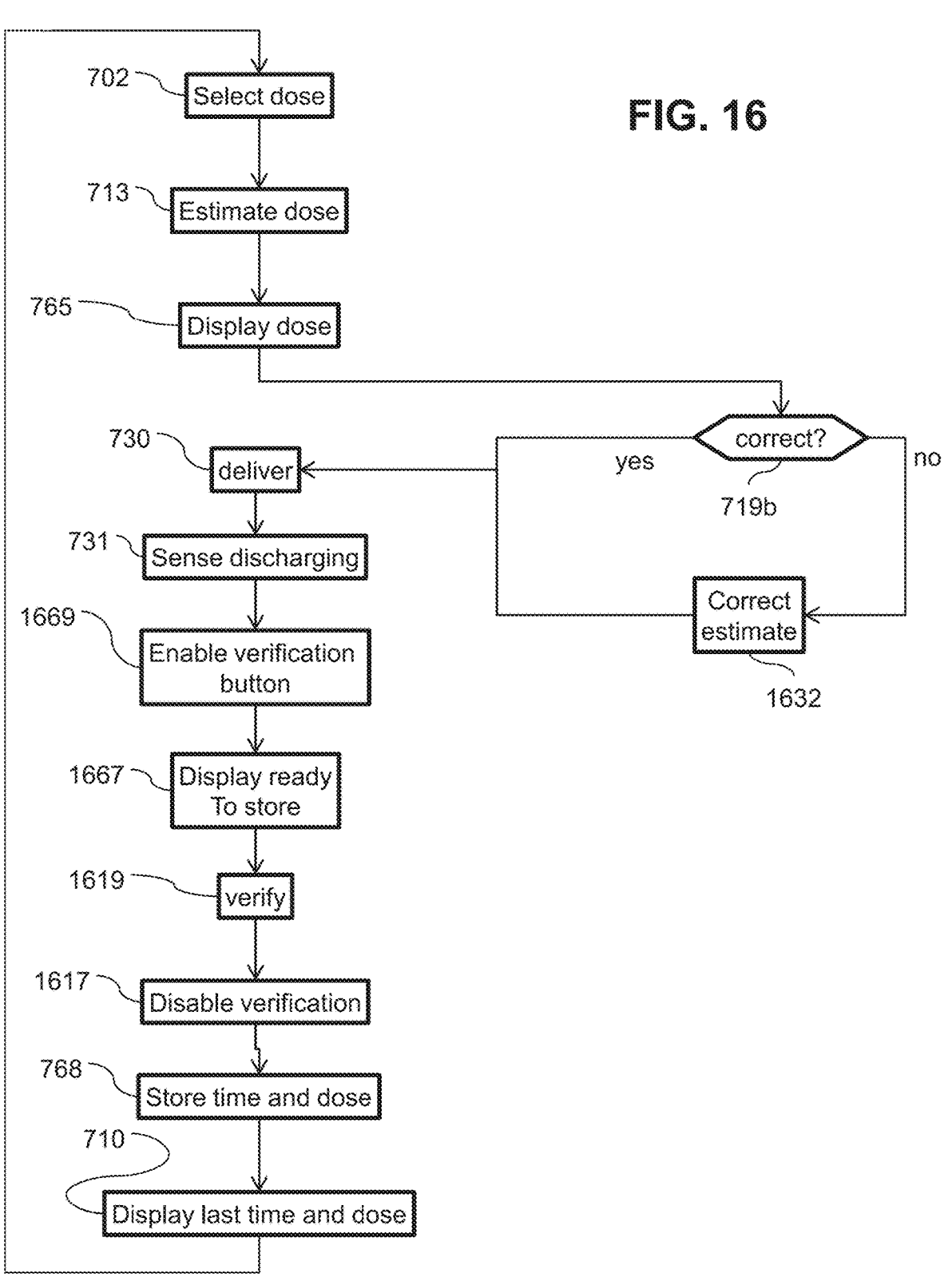
FIG. 16 is a flow chart illustration of delivering a drug with a drug delivery device and recording delivery with an adjunct device in accordance with some embodiments of the present invention.

FIG. 16 is a flow chart illustration of delivering a drug with a drug delivery device and of recording delivery with an adjunct device in accordance with some embodiments of the present invention. In some embodiments, an adjunct device may record a drug delivery and/or dosage dependant on a positive action of the user of the device. For example, a dosage and/or time of delivery may be recorded only when a user pushes a verification button. Optionally, the verification button may be enabled and/or disabled according to the detected state of the delivery device. Alternatively, a detected dosage and/or time of detected delivery may be recorded as unverified when an action is detected and not verified.

In some embodiments, a user may select 702 a dosage of an injection for example using a dosage selector of a drug delivery device. Optionally, the adjunct device detects the action of the user and/or estimates 713 the selected dosage. The adjunct device optionally displays 765 the estimated 713 dose on a display. Optionally the user then checks if the displayed dosage is correct 719*b*. For example, the user may compare the displayed dose of the adjunct device to a dose displayed on a dosage indicator of the drug delivery device. If the estimated dose is not correct 719*b*, then the user optionally corrects 1632 the estimated dose. For example, the estimated dose may be corrected with a user interface (for example using a dose incrementing button and/or a dose decrementing button). When the estimated dose of adjunct device is correct 719*b*, then the user optionally delivers 730 the dose with the delivery device.

In some embodiments, injection verification may be enabled 1669 when the device detects 731 that delivery has occurred (for example a verification button, for example button 1235*c*, may be enabled). Optionally, the user is notified 1667 when verification switches from a disabled to an enabled 1669 state and/or while verification is in enabled 1669 state, (for example by an audio alarm and/or by a light and/or by a symbol on display 1214 or by a notification on a computing device (e.g. the user's cell phone)). For example the notification may tell the user that the adjunct device is awaiting verification of delivery.

In some embodiments, when the user verifies 1619 delivery, the estimated dosage and/or time of delivery is stored 768. For example when a verification button is triggered while in an enabled state estimated values may be stored on a local memory of the adjunct device and/or sent to a personal computing device and/or another device. In some embodiments, verification may be disabled 1617 when a value is stored 768, for example, to prevent double storing of data, for example if the user accidently pushes a verification button twice. Alternatively or additionally, verification may be disabled upon an error condition, for example after a certain time delay after detecting an injection without verification and/or when a dosage setting change is detected but discharge is not detected.

In some embodiments, if the user triggers verification (for example by depressing a verification button) while verification is disabled, a dosage and/or time may not to be stored. In some embodiments, a provisional dose and/or time may be stored when delivery is detected without verification and/or when verification occurs in a disabled state. Optionally an indicator may be stored along with the time and/or dosage. For example the indicator may indicate whether the stored time and/or dosage was detected by the device, verified by the user and/or both detected and verified.

Device with Manual Verification

FIGS. 19A-22 are illustrations and methods of using an adjunct device used for monitoring a drug delivery device, in accordance with some embodiments of the present invention. In some embodiments, after detecting a dosage set in the drug delivery device, for example an injector, a user is requested to verify that the dosage presented by the adjunct device is identical to the dosage counter embedded in the injector. Alternatively or additionally, a user is requested to actively approve storing the usage data detected by the adjunct device, i.e. dosage count and time. In some embodiments, upon detection of a discrepancy, a user is prompted to correct a misreading of the adjunct device by manually increasing or decreasing the dosage displayed, optionally using a rocker switch.

Figures 19A, 19B:
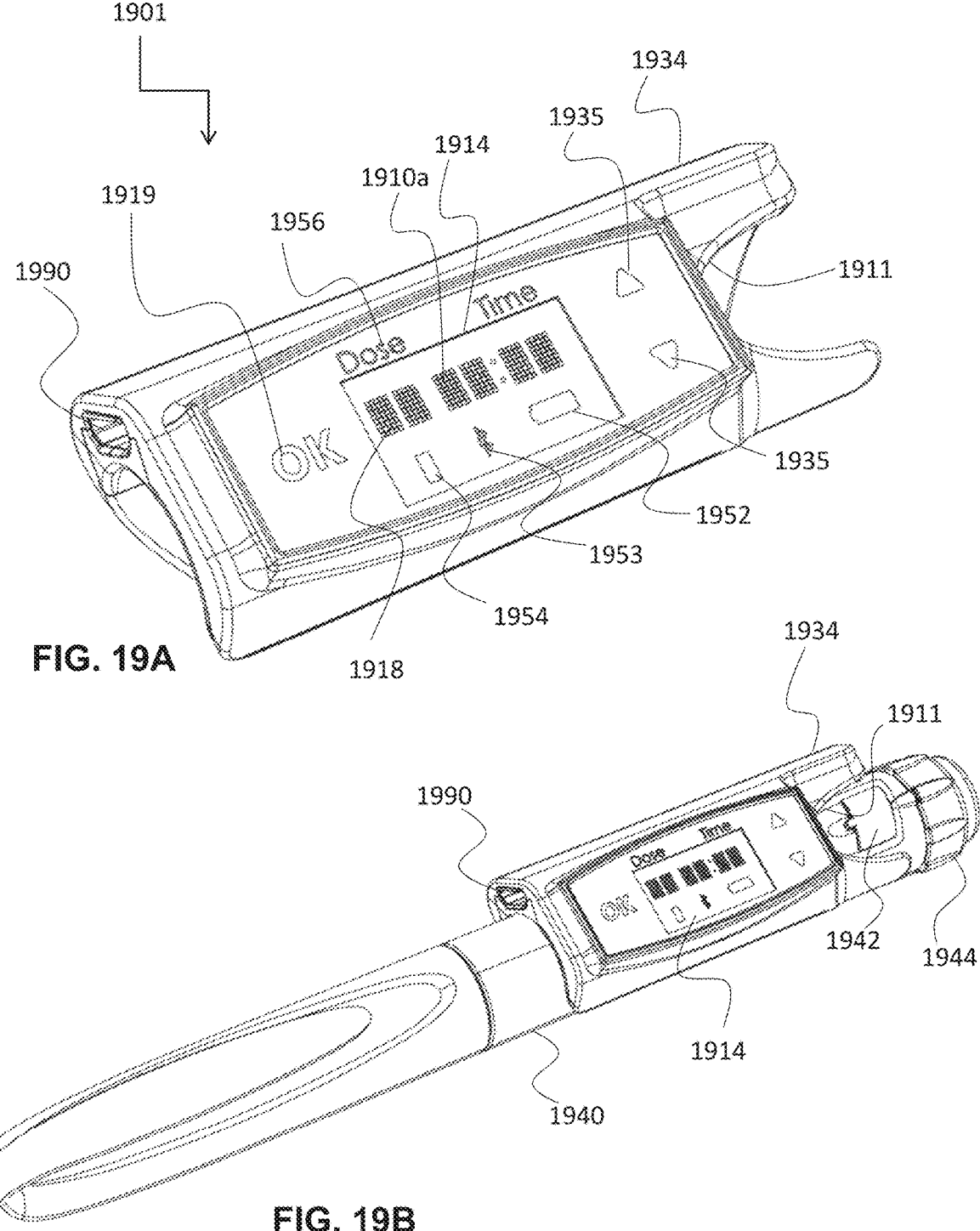
Figure 19C:
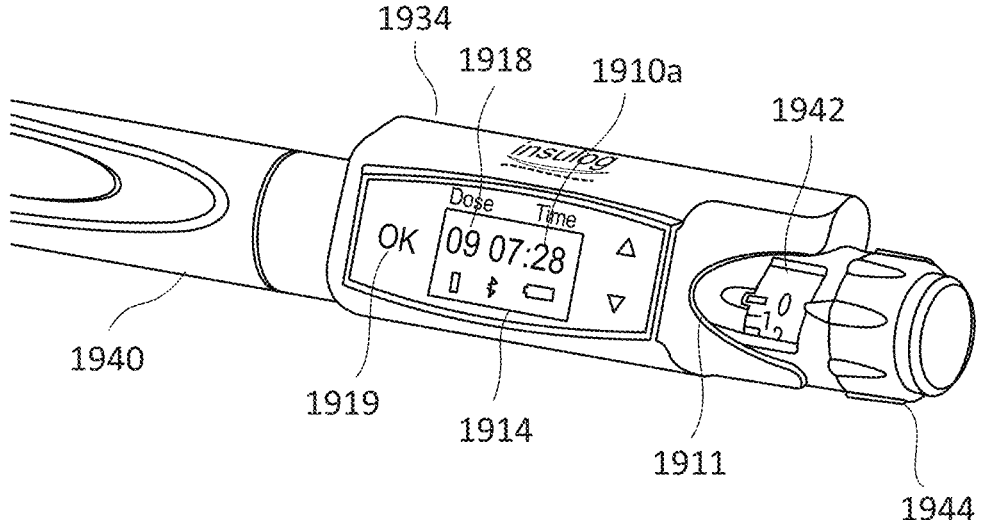

FIGS. 19A-19C illustrate a perspective view of an adjunct device for mounting on and/or monitoring the operation of a drug delivery device, e.g. an injector, in accordance with some embodiments of the invention. In some embodiments, the adjunct device is sized and shaped to be mounted over an injecting pen. Optionally the adjunct device detects and/or monitors usage specifications of the pen. In some embodiments, detected specifications are communicated to a storage means, optionally to a smart phone device. In some embodiments, data is sent when a user actively approves storing the detected usage specifications. Optionally verification may include operating a dedicated verification switch, for example a button embedded in the user interface of the device.

In some embodiments, a system includes an injector and/or an adjunct device. In some embodiments, the adjunct device includes one or more sensors. The adjunct device optionally includes a processor operationally connected to the sensors for receiving sensor output and/or determining injector status and/or activity from sensor output and/or receiving user input, such as an active user confirmation. Optionally the adjunct device is mounted onto the injector in a manner that allows normal use of the injector. For example the adjunct device may allow user access to some and/or all controls and/or indicators of the injector.

FIG. 19A illustrates an embodiment of an adjunct device 1901 in accordance with an embodiment of the current invention. Optionally device 1901 has a manual verification module. In some embodiments, the adjunct device has display 1914, optionally an LCD. In some embodiments, the display is for graphically presenting a user interface 1956, optionally comprising captions or user instructions. For example, the user interface contains a dosage counter 1918 and/or a time section 1910*a*. Alternatively or additionally, user interface 1956 comprises user indicators, for example battery power indicator 1952 and/or wireless communication operation indicator 1953 and/or data waiting to be uploaded 1954. For example, adjunct device 1901 comprises a memory for recording usage parameters, such as for example, dosage counts and/or injection timings. Optionally, when data is recorded but is not yet uploaded to an external computing device it an indication such as indicator 1954 is presented. Alternatively or additionally, indicators such as 1952 and/or 1953 and/or 1954 are presented to a user by having a light indicator, or alternatively or additionally, by a notification and/or massage sent to a computational device, e.g. a smart phone.

Optionally, user interface 1956 also comprises a rocker switch 1935 for manually increasing and/or decreasing the dose count displayed in the dosage counter 1918. Alternatively or additionally, a manual verification button, for example OK button 1919, is provided for a user to actively approve that the value displayed on dosage counter 1918 is correct.

In some embodiments, adjunct device 1901 includes a plug in port 1990, for example a mini-USB port. For example, the adjunct device may be charged and/or data may be transferred and/or software updates may be downloaded. Optionally, uploading is performed after a manual approval by a user, for example, after a user pushes verification button 1919. Alternatively, data is automatically uploaded to and the device waits for approval before recording the data in a database. Alternatively, data is automatically uploaded and stored (for example when the adjunct device detects that a drug has been discharged. Alternatively or additionally, manual verification is required for wired communication. Alternatively or additionally, uploading and/or downloading are automatic when the unit is connected to a cradle and/or charged and/or connected via a wired connection to a computing device. Optionally, port 1990 is positioned such that it causes minimal interference with a drug delivery device, for example by being positioned oppositely to view port 1911 which allows viewing access to functional parts of the injector being used with the device 1901.

Reference is now made to FIG. 19B illustrating adjunct device 1901 mounted on injector pen 1940. In some embodiments, adjunct device 1901 comprises a body 1934 sized and shaped to be mounted over a drug delivery device, for example injector 1940. In some embodiments, body 1934 includes a view port 1911. Optionally, view port 1911 is positioned over and/or allows viewing of features displayed by injector 1940. For example, view port 1911 includes a window through which of pen dosage indicator 1942 is visible. Adjunct device 1901 optionally allows convenient access to a dosage selector 1944 of injector 1940. For example, when mounted on pen 1940 the device 1901 does not interfere with use of selector 1944. In some embodiments, display 1914 is oriented such that a user can view both the injector pen display 1944 and the adjunct device display 1914, optionally simultaneously. Optionally, orientation of the adjunct device is guided by the presence of the view port, optionally having an outline which fits with a geometrical outline of display 1942 of injector 1940.

Reference is now made to FIG. 19C exemplifying an adjunct device 1901 mounted over a drug delivery device in the form of an injector pen 1940, according to some embodiments of the current invention. In some embodiments, adjunct device 1901 is mounted on an injector pen 1940 such that the pen dosage indicator 1942 is viewable by a user, optionally through view port 1911. Optionally, view port 1911 is wide enough to allow at least viewing of the dosage count provided by the injector pen 1940. In some embodiments, adjunct device 1901 comprises display 1914, optionally having dosage count 1918 and/or time section 1910a, optionally viewable in substantially the same plane as dosage indicator 1942. Optionally, action is not taken, for example data is not stored and/or not transferred, until a user confirms the action. For example, data may be stored and/or transferred after the user confirms an agreement between dosage counter 1918 and dosage indicator 1942, optionally by pushing the OK button 1919. Alternatively or additionally, data may be stored and/or transferred after the user a corrects a discrepancy between dosage counter 1918 and dosage indicator 1942 for example by adjusting the dosage counter 1918. Adjusting dosage counter optionally includes manually by pushing rocker switch 1935 up or down buttons. Alternatively or additionally, a warning may be issued and/or stored if an injection is detected but data is not stored. Alternatively or additionally, data may be flagged as unconfirmed until user verification. In some embodiments, adjunct device is programmed to send out usage information only after an active approval of the user, for example after pushing verification button 1919.

Figures 20A, 20B, 20C:
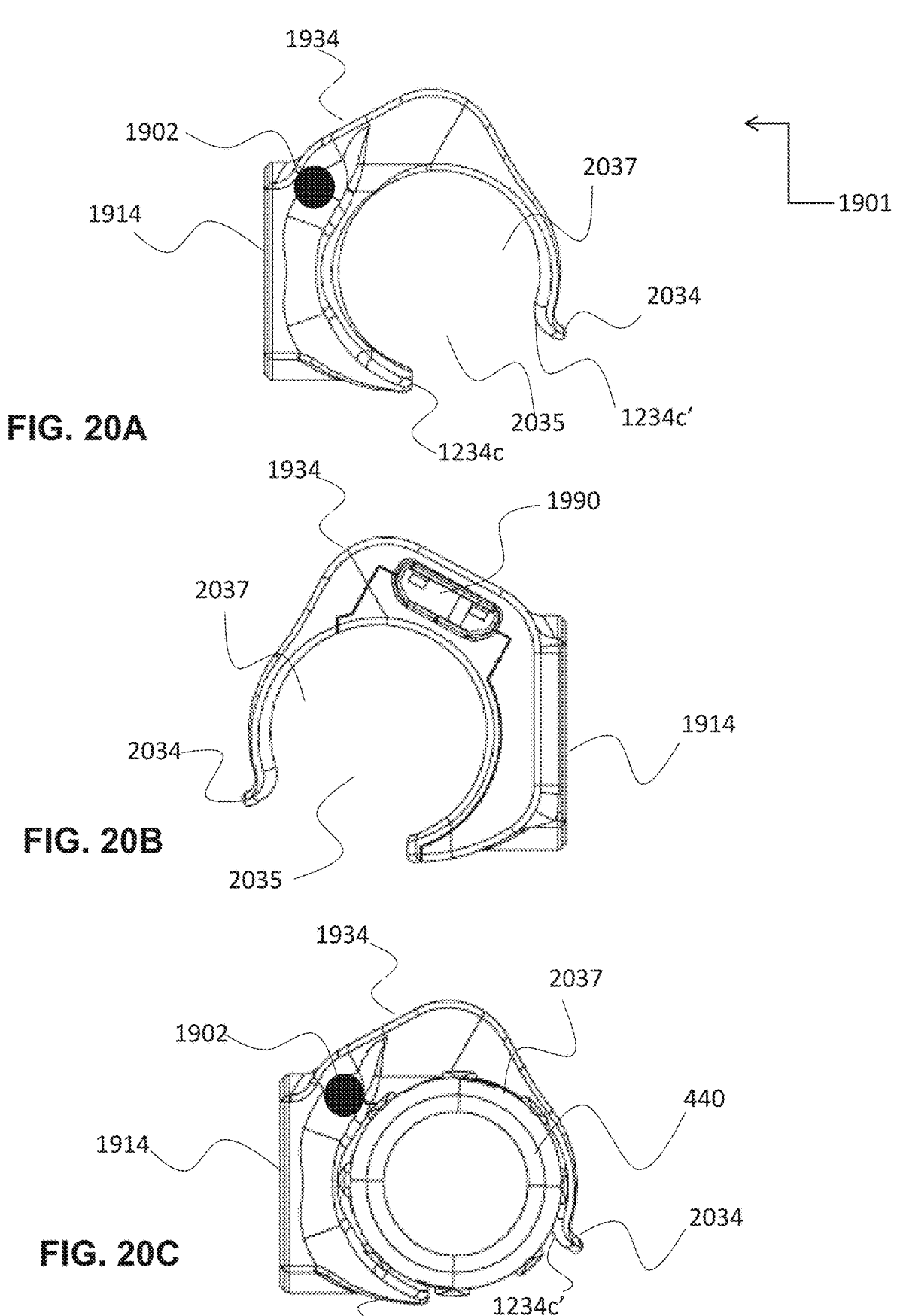

Reference is now made to FIGS. 20A-20C, illustrating side views of adjunct device 1901, used for monitoring a drug delivery device, for example an injector pen. In some embodiments, an adjunct device may include one or more sensors 1902 and/or sensor arrays, optionally a 1D accelerometer and/or 2D accelerometer and/or a 3D accelerometer and/or a gyro. In some embodiments, both an accelerometer and a gyro are located within body 1934, optionally in a single place, and/or optionally in proximity to an adjunct to selector 1944 and/or device display 1914, and/or optionally opposite to an opening into channel 2037.

In some embodiments, sensor 1902 is positioned closer to front section 1234c. Alternatively or additionally, sensor 1902 is positioned closer to rear section 1234c'. Alternatively, sensor 1902 is positioned symmetrically with respect to front section 1234c and rear section 1234c'.

In some embodiments, adjunct device 1901 is shaped substantially as a horseshoe and/or an open circle, defining an opening, optionally the opening is a slit uniform in width for example as illustrated as channel 2037. In some embodiments, adjunct device 1901 is mounted onto an injection pen 1940 through channel 2037. In some embodiments, an adjunct device is sized to enclose and/or grasp pen 1940 around at least 180° of a circumference of the pen's circumference. Alternatively, an adjunct device is sized to enclose and/or grasp pen 1940 around at least 200° of a circumference of the pen's circumference. Alternatively, an adjunct device is sized to enclose and/or grasp pen 1940 around at least 240° of a circumference of the pen's circumference. Alternatively, an adjunct device is sized to enclose and/or grasp pen 1940 around at least 270° of a circumference of the pen's circumference. Alternatively, an adjunct device is sized to enclose and/or grasp pen 1940 around at least 300° of a circumference of the pen's circumference.

Optionally, the pen is pushed into adjunct device through channel 2037 and clicks into place. Optionally the pen is inserted into the channel in between front section 1234c and rear section 1234c'. In some embodiments, a force is needed to push the injector into the inner portion of the adjunct device, optionally exerting a force in the range of 0.5-1 N, or 1-2 N, or 2-4 N or 4-8 N or any force smaller, larger or intermediate. In some embodiments, at least one of front and rear sections, 1234c and 1234c', comprises a flex, or a bent, 2034 optionally curved towards the outer surface of adjunct device 1901. Optionally, at least part of front section 1234c and/or rear section 1234c' is elastic, optionally enough to be relatively easy to open, optionally elastically returning to an initial position. For example, when directing injector 1940 into channel 2037, flex(es) 2034 in front section 1234c and/or rear section 1234c' are shaped to assist with opening channel opening 1235 to receive the pen and then close, optionally elastically, once the pen is in place.

In some embodiments, the smaller the width of channel 2037, the more elastic are front section 1234c and/or rear section 1234c', potentially allowing temporary opening of channel 2035 enabling insertion of an injector pen which is wider than a width of channel 2035. In some embodiments, channel 2035 is further opened by exerting a force in the range of 0.5-1 N, or 1-2 N, or 2-4 N or 4-8 N or any force smaller, larger or intermediate.

In some embodiments, the diameter of a circle completing the horseshoe shape of the adjunct device is configured to be slightly smaller than an injector diameter, optionally between 0.5 mm and 3 mm. Optionally, an adjunct device is configured to be elastic enough to allow pushing of the injector into the a more constraint circumference. In some embodiments, a force is exerted on the adjunct device when it is mounted onto a slightly bigger pen, optionally the force is in the range of 0.5-1 N, or 1-2 N, or 2-4 N or 4-8 N or any force smaller, larger or intermediate.

In some embodiments, body 1934 comprises channel opening 1235. Optionally, channel opening 1235 is shaped and sized to grasp an object, optionally cylindrical, having a width of a range between 5 mm and 10 mm, and/or between 10 mm and 1 cm, and/or between 1 cm and 3 cm, and/or any range being smaller, larger or intermediate. In some embodiments, channel opening 1235 is configured to be slightly smaller than a width of a designated injector in order to enclose the pen in place. Optionally, slightly smaller refers to a range between 1% and 10% smaller width or a range between 10% and 20% smaller. In some embodiments, channel opening 1235 is positioned such that channel 1237 encloses a partial circumference of the injector. Optionally, injector pen is enclosed by said body at about 60% of its circumference. Alternatively, injector pen is enclosed by said body at about 80% of its circumference. Alternatively, injector pen is enclosed by said body at about 70% of its circumference. Alternatively, injector pen is enclosed by said body at about 90% of its circumference.

In some embodiments, channel 2037 is sized and shaped for accommodating a variety of injectors. For example, channel 2037 is fit to accommodate Sanofi® Solostar® and/or Eli Lili® Kwikpen® and/or Novo Nordisk® Flexpen® and/or Flextouch. Alternatively, channel 2037 is sized and/or shaped to fit a single brand of an injector. In some embodiments, channel 2037 is shaped as a square or rectangular-like. Alternatively or additionally, channel 2037 is optionally large enough and/or flexible enough to accommodate a pen with a polygonal shape and/or having bulges and/or protrusions and/or angled portions for example the Quikpen®.

Optionally, sensor 1902 comprises a pressure sensor. In some embodiments, sensing the pressure a specific injector exerts on the adjunct device corresponds to the injector's brand, optionally an adjunct device automatically recognizes the injector's brand once it is clicked into place. In some embodiments, an adjunct device comprises a memory module which is preloaded with pre-calibrated data pertaining to each brand of injector. In some embodiments, if an injector is not recognized, a warning is displayed, or the user is prompted to manually select a device, for example by presenting a menu, either in display 1914, or in a communicating computer device, such as e.g. a smart phone. Alternatively or additionally, if an injector pen is not recognized, a user is prompted to calibrate the device before use, such as described for example in FIGS. 9A-9B of the current application. Alternatively or additionally, a user device may be employed to recognize a pen type. For example, a user may take a picture of the pen and/or adjunct device with a personal computing device and/or a processor (for example of the adjunct device and/or the user device) may analyze the picture to determine the type of pen and/or whether the adjunct device is properly mounted.

Figure 21A:
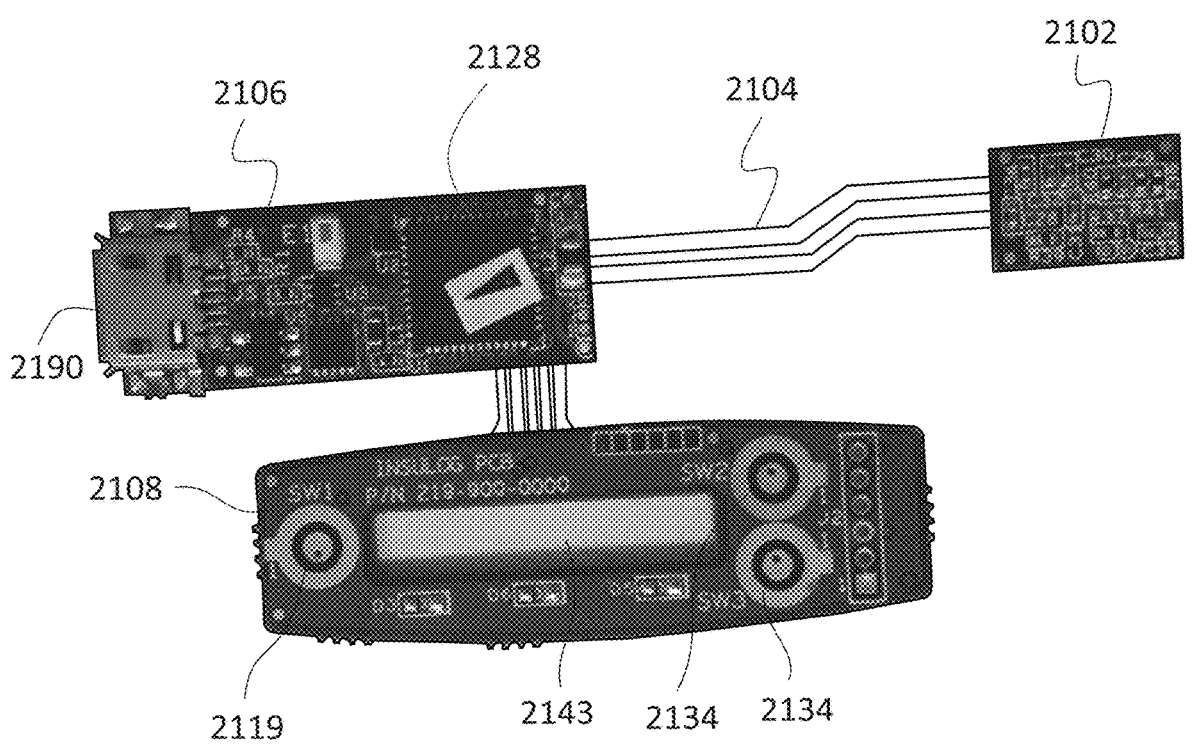
FIGS. 21A and 21B show an exemplary circuitry configuration embedded in an adjunct device used for monitoring a drug delivery device in accordance with some embodiments of the present invention, in which FIG. 21A exemplifies an embodiment of a circuitry configuration and FIG. 21B exemplifies the circuitry configuration of FIG. 21B as embedded in an adjunct device housing in accordance with some embodiments of the present invention.
Figure 21B:
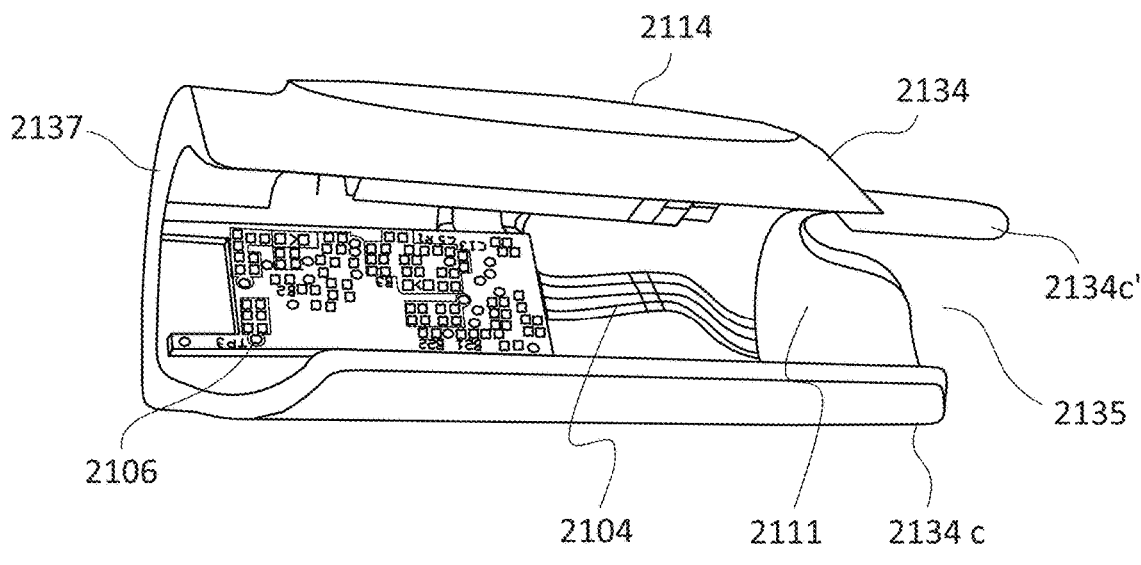

FIGS. 21A-21B exemplified a circuitry configuration of adjunct device 1901, in accordance with some embodiments of the present invention. FIG. 21A shows circuitry components and their configuration as spread outside of adjunct device 1901 accordance with some embodiments of the present invention. FIG. 21B shows the circuitry of FIG. 21A fitted into an exemplary casing of adjunct device 1901, in accordance with some embodiments of the present invention.

In some embodiments, a processor 2106 is provided having instructions for monitoring a drug delivery device. For example, processor 2106 may use output of a sensor 2102 to monitor dosage adjusting of the injector. Sensor 2102, optionally includes an accelerometer and/or gyro. In some embodiments, both an accelerometer, optionally a 3D, and a gyro are positioned in the same location. In some embodiments, sensor 2102 communicates with processor 2106 through arm 2104, optionally a relatively flexible arm. A potential advantage of a separate sensor unit is a greater freedom in positioning, potentially leading to accuracy in positioning which may provide sufficient sensing of the injector operation. A potential advantage of a separate sensor unit is that the sensor may vibrate more freely when it is not connected to a large mass object like a battery and/or PCB and/or a CPU. For example, sensor 2102 is optionally placed in closer proximity to the pen's dosage dial than the CPU, battery and/or PCB. Placing the sensor near the dial, potentially increases the power and quality of detection of vibration caused in the dial feature of the pen. In some embodiments, processor 2106 communicates with user interface circuitry 2108. Optionally, user interface circuitry is sized and shaped to be accommodated in adjunct device casing such that the device display 1914 is aligned with the display mount 2143.

Optionally, user interface 2108 comprises user buttons, for example optionally rocker switch 2134 and/or a manual approval button 2119. In some embodiments, processor 2106 transmits data relating to the adjustment and/or operation of an injector pen only after a user pushes approval button 2119. Optionally, processor 2106 comprises wireless port 2128, such as for example a Bluetooth. Alternatively or additionally, processor 2106 comprises a plug in port 2190 for wired communication, optionally used for charging and/or communication.

FIG. 21B exemplifies adjunct device casing in accordance with some embodiments of the current invention. Exemplified is an optional positioning of sensor 2102 in between front section 2134c and rear section 2134c', optionally in proximity to front section 2134c, alternatively or additionally in proximity to display port 2114. In some embodiments, casing 2134 is made of a flexible material, for example Acrylonitrile Butadiene Styrene (ABS). Alternatively or additionally, a material made of other polymers is used.

In some embodiments, casing 2134 comprises an inner cover 2111. Optionally, inner cover 2111 is provided to embedding circuitry components, such as for example sensor 2102. A potential advantage of having an inner cover is that it is likely to hold components in place, and/or protect sensitive components, and/or increase contact with an injector pen in areas where mechanical contact is required, such as for example in establishing a mechanical contact between sensor 2102 and an injector pen, which is optionally pushed into casing 2134 through opening 2135.

Figure 22:
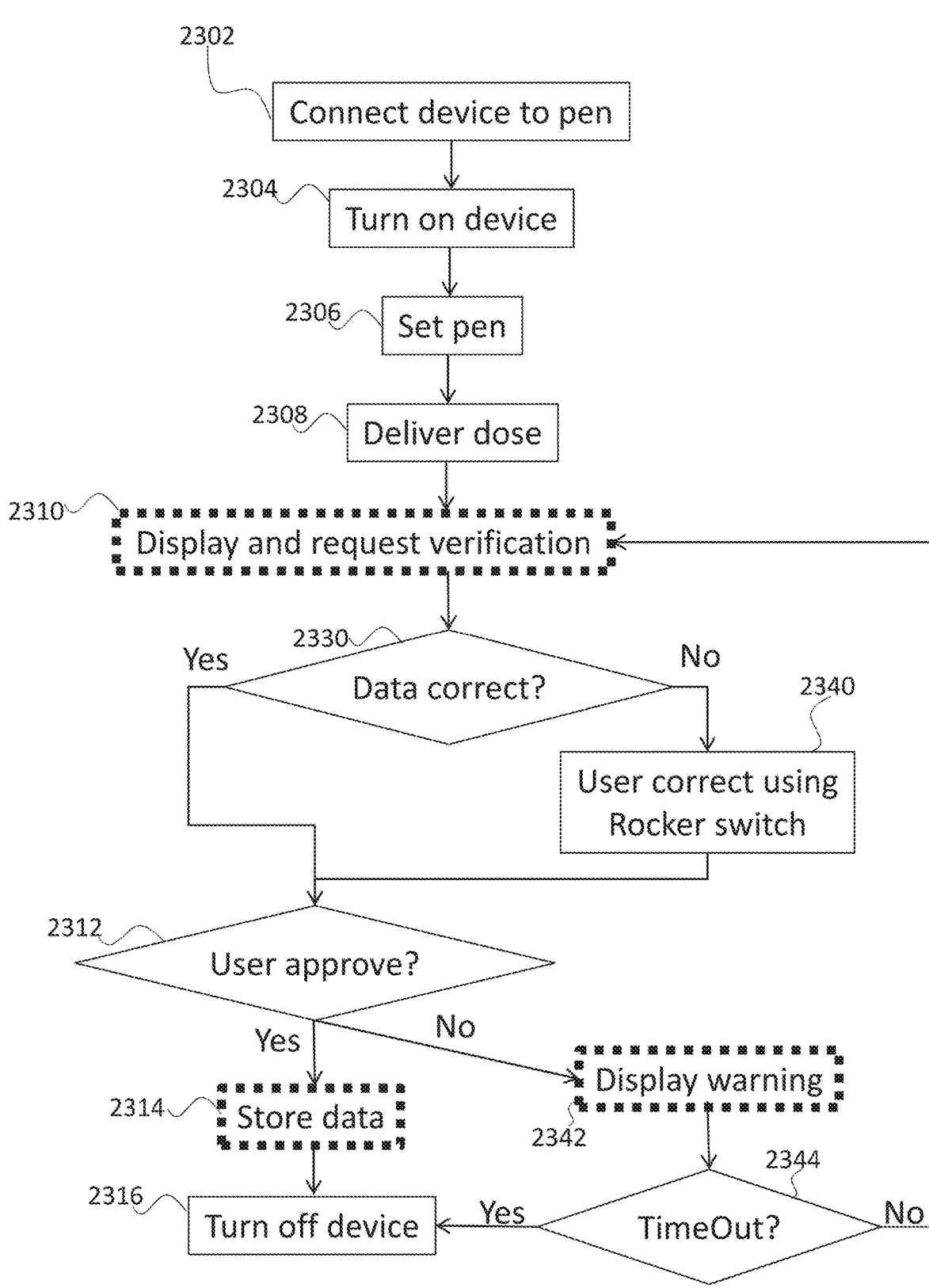
FIG. 22 is a flow chart illustration of methods to confirm and monitor the reporting of a state of an injector in accordance with some embodiments of the current invention.

FIG. 22 is a flow chart illustration of delivering a drug with a drug delivery device and an adjunct device, in accordance with some embodiments of the present invention. For example, delivery may be recorded with an adjunct device. Recorded data may be confirmed by the user before storing recorded data. In FIG. 22, continuous lines represent user actions, while dashed lines represent actions being executed by the adjunct device. In some embodiments, an adjunct device records a drug delivery and/or dosage dependent on a positive action of the user of the device. For example, a dosage and/or time of delivery may be recorded only when a user pushes a verification button. Optionally, the verification button may be enabled and/or disabled according to the detected state of the delivery device. Alternatively, a detected dosage and/or time of detected delivery may be recorded as unverified when an action is detected and not verified.

In some embodiments, a user connects 2302 an adjunct device 1901 to a drug delivery device, for example an injector pen. In some embodiments, an adjunct device is configured to recognize being pushed over an injector and clicked into place, optionally turning device on. Alternatively, a user turns the device on 2304 once the device is in place.

In some embodiments, a user selects 2306 a dosage of an injection for example using a dosage selector of a pen injector, and optionally proceeds to inject the selected dosage 2308. Optionally, the adjunct device detects the action of the user and/or estimates the selected dosage. The adjunct device optionally displays and prompts user verification 2310 on a display. Optionally the user then checks if the displayed dosage is correct and/or matches the dosage selector of the injector pen 2330. For example, the user may compare the displayed dose of the adjunct device to a dose displayed on a dosage indicator of the drug delivery device. If the estimated dose is not correct, then the user optionally corrects 2340 the estimated dose. For example, the estimated dose may be corrected with a user interface (for example using a dose incrementing button and/or a dose decrementing button and/or a rocker switch).

In some embodiments, the user delivers 2308 the dose with the delivery device. For example the user may deliver 2308 the dose after correcting and/or verifying the estimated dose of the adjunct device. Optionally, once adjunct device requests verification 2310, it will not proceed without an active user approval 2312, such as for example pushing a verification button. In some embodiments, after a preset time period without user verification, the device will display warning 2342. Optionally, preset time is 10-20 seconds, or 20-30 seconds, or 1 minute, or any time range smaller, larger or intermediate. Optionally, after displaying warning 2342 for a preset time, the device will request verification 2310 once more. Alternatively or additionally, a timeout 2344 is determined and device turns off and/or goes to sleep 2316. In some embodiments, request verification 2310 and/or warning 2342 are displayed on an external computing device, such as e.g. a user's phone.

Optionally, after user has approved a correct dosage counting by the device 2312, the device proceeds to storing the data 2314. In some embodiments, the device automatically sends usage data such as dosage count and/or delivery time to an external device, optionally a smart phone. Optionally, for example when a user having a disability and/or limited ability operates the device, the usage data is sent to a caregiver physician or a family member. Optionally, usage data will be sent together with an indication that the data has been actively approved by the user. Alternatively or additionally, an alert and/or notification is sent to a caregiver when too much is injected, and/or injections are missed, and/or injections are too close or far apart, and/or when device is not communicating for a predefined time period. Optionally, a caregiver can send back an alert and/or notification to a computing device of the user.

In some embodiments, users having vision disabilities take a picture of the adjunct device and send it to a caregiver, optionally in order to get assistance in reading the device display. Alternatively or additionally, a picture may be uploaded to a computational device having image analysis software configured for identifying a match or mismatch between the adjunct device and the injector.

In some embodiments, users can share usage data, in numerical data or as a picture, between other users, for example, through a social network, for example dedicated to diabetic patients.

In some embodiments, injection verification is enabled 2310 only when the device detects that delivery has occurred 2308 (for example a verification button is enabled). Optionally, the user is notified when verification switches from a disabled to an enabled state and/or while verification is in enabled state, (for example by an audio alarm and/or by a light and/or by a symbol on display or by a notification on a computing device (e.g. the user's cell phone)). For example the notification may tell the user that the adjunct device is awaiting verification of delivery.

In some embodiments, an adjunct device may be turned on automatically following sensing of vibration, optionally of mounting over an injector pen and/or adjusting an injector pen. Optionally, if adjunct device detects an extended time period from past operation, a warning is provided (for example by an audio alarm and/or by a light and/or by a symbol on display or by a notification on a computing device (e.g. the user's cell phone)). In some embodiments, dosage and/or timing of injections may be manually configured and stored through the adjunct device, such as for example, when an injector pen is used without monitoring of the adjunct device.

In some embodiments, estimated values are stored on a local memory of the adjunct device and/or sent to a personal computing device and/or another device, optionally sent to a physician and/or a family member. In some embodiments, verification is disabled when a value is stored, for example, to prevent double storing of data, for example if the user accidently pushes a verification button twice. Alternatively or additionally, verification is disabled upon an error condition, for example after a certain time delay after detecting an injection without verification and/or when a dosage setting change is detected but discharge is not detected.

It is expected that during the life of a patent maturing from this application many relevant technologies and/or materials will be developed and the scope of the terms are intended to include all such new technologies and materials a priori.

As used herein the terms "about", "approximately" and "substantially" refer to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

EXAMPLES

Reference is now made to the following examples, which together with the above descriptions illustrate some embodiments of the invention in a non limiting fashion.

Figure 17:
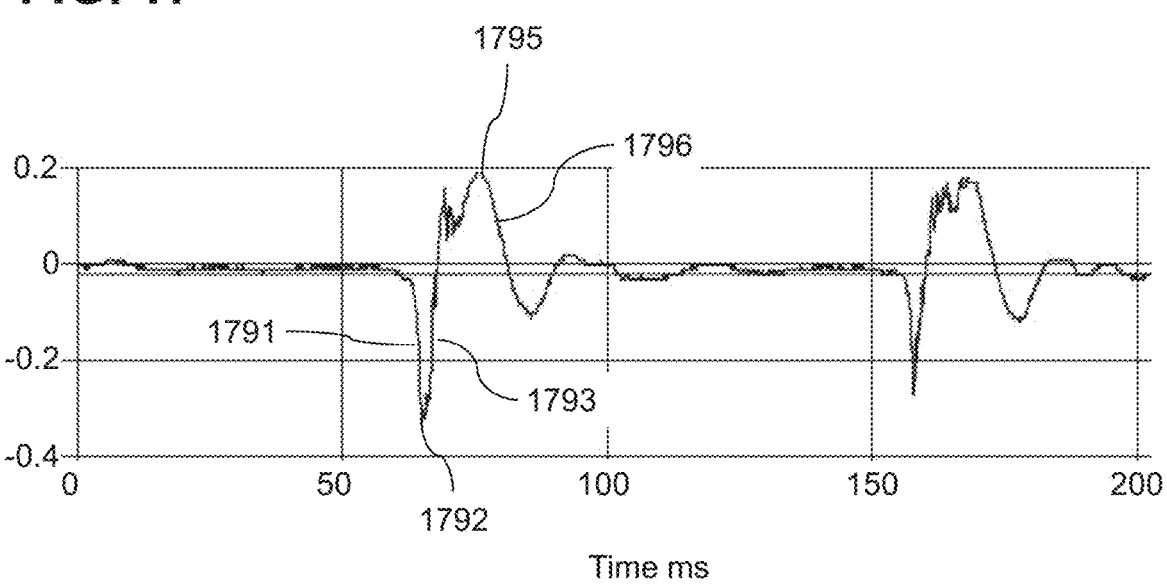
FIGS. 17 and 18 illustrate measured signals along a circumferential axis by a movement sensor mounted on an insulin injector pen during incrementing and decrementing a dosage respectively.
Figure 18:
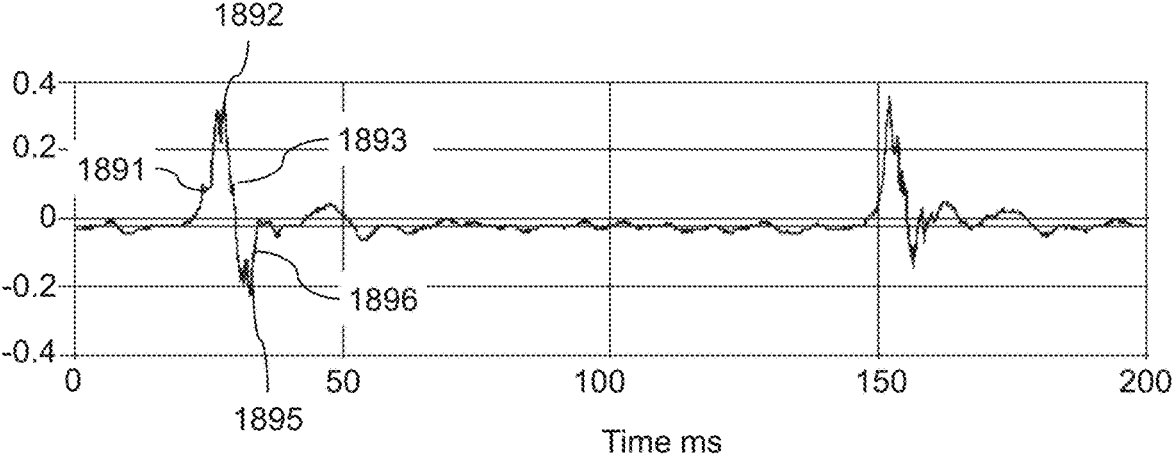

FIGS. 17 and 18 illustrate examples of sensor output from a circumferential axis of a movement sensor mounted on an insulin injector pen. An Analog Device ADXL327 tilt sensing movement sensor was mounted on the ventral side of an Apidara® SoloSTAR® insulin injector pen near the proximal end thereof. Movement was measured during incrementing and decrementing of a dosage of the pen. The movement sensor is described in the Analog Devices ASXL327 specification sheet Rev. 0 published in 2009 by and available from Analog Devices, Inc. One Technology Way, PO. Box 9106 Norwood, MA 02062-9106. The sample rate was 10000/second.

FIG. 17 illustrates movements caused by incrementing a dosage. The abscissa is time and the ordinate axis is sensor output. A first increment of dosage occurs a 600 ms and a second incrementing of the dose occurs as 1550 ms.

FIG. 18 illustrates movements caused by decrementing a dosage. The abscissa is time and the ordinate is sensor output. A first decrement of dosage occurs a 250 ms and a second incrementing of the dose occurs as 1450 ms.

The applicant has found that a motion detector can be used to detect and/or differentiate increasing and decreasing a dosage on in injector pen. In some embodiments, the signal for incrementing a dosage is differentiated from the signal for incrementing a dosage by the direction of the pulse. For example the circumferential signal for incrementing is in the opposite direction from the signal for decrementing. For example, the signal for incrementing initially rises and then falls whereas the signal for decrementing initially falls and then rises.

In some embodiments, the signal for incrementing a dosage is differentiated from the signal for incrementing a dosage according to the direction of the pulse. For example the circumferential signal for incrementing is in the opposite direction from the signal for decrementing. For example, in FIG. 17 and an initial peak 1792 for incrementing is downward and the subsequent recovery peak 1795 is upward. Just the opposite in FIG. 18 for decrementing a dosage an initial peak 1892 for decrementing is upward and the subsequent recovery peak 1795 is downward.

In some embodiments, the signal for incrementing a dosage is differentiated from the signal for decrementing a dosage according to the direction of the pulse. For example the circumferential signal for incrementing is in the opposite direction from the signal for decrementing. For example, in FIG. 17 and an initial peak 1792 for incrementing is downward and the subsequent recovery peak 1795 is upward. Just the opposite in FIG. 18 for decrementing a dosage, an initial peak 1892 for decrementing is upward and the subsequent recovery peak 1795 is downward.

In some embodiments, the signal for incrementing a dosage is differentiated from the signal for incrementing a dosage according to the pulse width. For example the pulse width of the initial pulse 1792 is shorter for incrementing than the width of the initial pulse 1892 for decrementing. For example the pulse width of the subsequent recovery pulse 1795 is longer for incrementing than the width of the recovery pulse 1895 for decrementing the dosage. For example incrementing can be differentiated by decrementing by comparing the ratio of lengths of the initial pulse (e.g. (the incrementing initial pulse 1792 width)/(the incrementing recovery pulse 1795 width)) is less than (the decrementing initial pulse 1892 width)/(the decrementing recovery pulse 1895 width)). Thus when the ratio of initial to recovery pulse is less than a threshold, the pulse may be identified as a dosage increment and/or when the ratio of initial to recovery pulse is greater than a threshold, the pulse may be identified as a dosage increment.

In some embodiments incrementing may be differentiated from decrementing based on a slope and/or ratio of slopes. For example, the initial slope 1791 for incrementing may be sharper than the initial slope 1891 for decrementing. For example, the initial fall off slope 1793 for incrementing may be sharper than the initial fall off slope 1892 for decrementing. For example, the recovery fall off slope 1796 for incrementing may be shallower than the recovery fall off slope 1891 for decrementing. For example the ratio of the initial slope to the recovery fall off slope may be used to differentiate between incrementing and decrementing a dosage. For example if the absolute value of the slope ratio 1791/1796 is above a threshold the signal is identified as incrementing a dose and/or if the absolute value of the slope ratio 1891/1896 is below the threshold the signal is identified as incrementing a dose.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for calibrating a dosage tracking device releasably connected to a pen injector, comprising:
   sensing a delivered dosage from the pen injector;
   reading a selected dosage from the dosage tracking device while releasably connected to the pen injector; and
   comparing the delivered dosage from the pen injector and the selected dosage from the dosage tracking device, and if there is not agreement between the delivered dosage from the pen injector and the selected dosage from the dosage tracking device, then adjusting dosage output of the dosage tracking device according to the delivered dosage from the pen injector.

2. The method of claim 1, further comprising comprising wirelessly transmitting the delivered dosage and the selected dosage from the dosage tracking device to a mobile phone.

3. The method of claim 1, further comprising sensing a releasable connection of the dosage tracking device to a first pen injector and sensing a releasable connection of the dosage tracking device to a second pen injector.

4. The method of claim 3, wherein the dosage tracking device includes a quick release mechanism for releasably connecting the dosage tracking device to the first pen injector and for releasably connecting the dosage tracking device to the second pen injector.

5. The method of claim 1, further comprising:

measuring circumferential acceleration of the pen injector when the dosage tracking device is releasably connected to the pen injector using a sensor included in the dosage tracking device;

distinguishing a click of a dosage adjuster included in the pen injector; and adjusting dosage output of the dosage tracking device according to the measuring circumferential acceleration and the click of the dosage adjuster.

6. The method of claim 1, further comprising zeroing an injection dosage of the pen injector and zeroing a dosage counter of the dosage tracking device.

7. A method for calibrating a dosage tracking device releasably connected to one pen injector of multiple pen injectors, comprising:

releasably connecting the dosage tracking device to a first pen injector;

sensing a first delivered dosage from the first pen injector; reading a first selected dosage from the dosage tracking device while the dosage tracking device is releasably connected to the first pen injector;

comparing the first delivered dosage from the first pen injector and the first selected dosage from the dosage tracking device, and if there is not agreement between the first delivered dosage from the first pen injector and the first selected dosage from the dosage tracking device, then adjusting dosage output of the dosage tracking device according to the first delivered dosage from the first pen injector;

releasably connecting the dosage tracking device to a second pen injector;

sensing a second delivered dosage from the second pen injector; reading a second selected dosage from the dosage tracking device while the dosage tracking device is releasably connected to the second pen injector; and comparing the second delivered dosage from the second pen injector and the second selected dosage from the dosage tracking device, and if there is not agreement between the second delivered dosage from the second pen injector and the second selected dosage from the dosage tracking device, then adjusting dosage output of the dosage tracking device according to the second delivered dosage from the second pen injector.

8. The method of claim 7, further comprising wirelessly transmitting the first delivered dosage and the first selected dosage from the dosage tracking device to a mobile phone, and providing an instruction using the mobile phone to adjust the dosage output of the dosage tracking device.

9. The method of claim 7, further comprising sensing releasable connection of the dosage tracking device to the first pen injector and sensing releasable connection of the dosage tracking device to the second pen injector using a sensor used to detect the first delivered dosage and to detect the second delivered dosage.

10. The method of claim 7, wherein the dosage tracking device includes a quick release mechanism for releasably connecting the dosage tracking device to the first pen injector and for releasably connecting the dosage tracking device to the second pen injector.

11. The method of claim 7, further comprising precalibrating the dosage tracking device to the first pen injector using a sensor and a processor configured to recognize the first pen injector.

12. The method of claim 11, wherein the sensor is a vibration sensor and the processor is configured to distinguish a characteristic sound of the first pen injector.

13. A method for calibrating a dosage tracking device releasably connected to a pen injector, the method comprising:

measuring a delivered dosage from the pen injector using one or more sensors on the dosage tracking device while the dosage tracking device releasably connected to the pen injector;

reading a desired dosage using at least one sensor of the one or more sensors on the dosage tracking device releasably connected to the pen injector;

comparing the delivered dosage from the pen injector and the desired dosage from the dosage tracking device;

if there is agreement between the delivered dosage from the pen injector and the desired dosage from the dosage tracking device, then indicating a dosage as the delivered dosage; and if there is not agreement between the delivered dosage from the pen injector and the desired dosage from the dosage tracking device, then adjusting dosage output of the dosage tracking device according to the delivered dosage from the pen injector.

14. The method of claim 13, further comprising a verification button mounted on a housing and configured for identifying a user action indicative of injection; wherein the verification button is enabled and disabled by a processor.

15. The method of claim 13, wherein the one or more sensors includes an active vibration sensor to measure activity in the pen injector.

16. The method of claim 15, further comprising: detecting a pulse using the active vibration sensor; and when the pulse lasts more than a threshold time pulse width, then adjusting of the dosage tracking device in a first manner, and when the pulse lasts less than the threshold time pulse width, then adjusting of the dosage tracking device in a second manner.

\* \* \* \* \*